US012343132B2

(12) United States Patent
Benjamini et al.

(10) Patent No.: US 12,343,132 B2
(45) Date of Patent: Jul. 1, 2025

(54) MULTIDIMENSIONAL MRI SIGNATURE FOR SPECIFIC DETECTION OF TRAUMATIC BRAIN INJURY IN VIVO

(71) Applicants: The United States of America, as represented by the Secretary, Department of Health and Human Services, Bethesda, MD (US); The Henry M. Jackson Foundation for the Advancement of Military Medicine, Inc., Bethesda, MD (US)

(72) Inventors: Dan Haim Benjamini, Bethesda, MD (US); Peter J. Basser, Bethesda, MD (US); Diego Iacono, Bethesda, MD (US)

(73) Assignees: The United States of America, as represented by the Secretary, Department of Health and Human Services, Bethesda, MD (US); The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 0 days.

(21) Appl. No.: 18/019,725

(22) PCT Filed: Jul. 14, 2021

(86) PCT No.: PCT/US2021/041663
§ 371 (c)(1),
(2) Date: Feb. 3, 2023

(87) PCT Pub. No.: WO2022/031414
PCT Pub. Date: Feb. 10, 2022

(65) Prior Publication Data
US 2023/0355126 A1 Nov. 9, 2023

Related U.S. Application Data

(60) Provisional application No. 63/061,105, filed on Aug. 4, 2020.

(51) Int. Cl.
*A61B 5/055* (2006.01)
*G01R 33/483* (2006.01)
*G01R 33/50* (2006.01)

(52) U.S. Cl.
CPC ............ *A61B 5/055* (2013.01); *G01R 33/483* (2013.01); *G01R 33/50* (2013.01); *A61B 2576/00* (2013.01)

(58) Field of Classification Search
CPC ......................... G01R 33/483–50; A61B 5/055
See application file for complete search history.

(56) References Cited

U.S. PATENT DOCUMENTS

2018/0329006 A1 * 11/2018 Haldar ................ G01R 33/543
2019/0178964 A1   6/2019 Basser et al.

FOREIGN PATENT DOCUMENTS

WO   WO 2018/031942 A1   2/2018
WO   WO 20180187764 A1  10/2018

OTHER PUBLICATIONS

Adams et al., "Diffuse axonal injury due to nonmissile head injury in humans: An analysis of 45 cases," *Ann. Neurol.* 12: 557-563 (1982).

(Continued)

*Primary Examiner* — Carolyn A Pehlke
(74) *Attorney, Agent, or Firm* — Leydig, Voit & Mayer, Ltd.

(57) ABSTRACT

Multidimensional MRI-based methods permit identification and categorization of brain specimens to identify sub-voxel tissue components that are specific to traumatic axon injury or other lesions. Lower dimensional MR spectral data is (Continued)

acquired and processed to provide multidimensional MR data of higher dimensions. One or more spectral ranges are selected that define signatures for brain injury and evaluation of the multidimensional MR data in these ranges is used to locate voxels associated with brain injury. For example, partial one dimensional data sets such as T1, T2, and mean diffusion coefficient (MD) data sets can be combined to provide two dimensional data sets such as T1-T2, MD-T2, and MD-T1 data sets. Using the spectral signatures, a specimen image can be produced showing areas of lesser or greater injury.

17 Claims, 57 Drawing Sheets

(56) References Cited

OTHER PUBLICATIONS

Avram et al., "Efficient experimental designs for isotropic generalized diffusion tensor MRI (IGDTI)," *Magn. Res. Med.* 79:180-194 (2018).
Bai et al., "Efficient 2D MRI relaxometry using compressed sensing," J. Magn. Reson., 255:88-99 (Jun. 2015).
Benjamini and Basser, "Use of marginal distributions constrained optimization (MADCO) for accelerated 2D MRI relaxometry and diffusometry," J. Magn. Reson. 271: 40-45 (Oct. 2016).
Benjamini et al., "Magnetic resonance microdynamic imaging reveals distinct tissue microenvironments," NeuroImage, 163: 183-196 (Sep. 2017) Author Manuscript.
Benjamini et al., "Joint distribution of axonal length and diameter quantifies beading in traumatic brain injury," Proc. Intl. Mag. Reson. Med., 3584: 1-3 (Apr. 2019).
Benjamini et al., "Multidimensional correlation MRI," *NMR in Biomed*, 33(12): 1-17, e4226 (Jan. 2020).
Kim et al., "Diffusion-relaxation correlation spectroscopic imaging: A multidimensional approach for probing microstructure," *Mag. Reson. Med.*, 78: 2236-2293 (Mar. 2017).
Pas et al., "Retaining information from multidimensional correlation MRI using a spectral regions of interest generator," *Sci. Rep.* 10(3246): 1-10 (2020).
European Patent Office, International Search Report and Written Opinion of the International Searching Authority issued in PCT/US2021/041663, dated Nov. 5, 2021, 11 pages.
The International Bureau of WIPO, International Preliminary Report on Patentability issued in PCT/US2021/*041663, dated Feb. 16, 2023, 8 pages.
Benjamini et al., "Diffuse axonal injury has a characteristic multidimensional MRI signature in the human brain," Brain 144: 800-816 (2021).
Benjamini et al., "Diffuse axonal injury has a specific multidimensional MRI signature in traumatically injured corpus callosum," Conference: International Society for Magnetic Resonance in Medicine (ISMRM) 2021, virtual. May 2021, 5 pages.
Fukuzaki et al., "The ability of line scan diffusion imaging method comparison with echo planner diffusion imaging," *International Society for Magnetic Resonance in Medicine*, abstract, p. 1833 (1999).
Pierpaoli et al., "Polyvinylpyrrolidone (PVP) water solutions as isotropic phantoms for diffusion MRI studies," *Proc Intl Mag Reson Med*, 17:1414 (2009).

\* cited by examiner

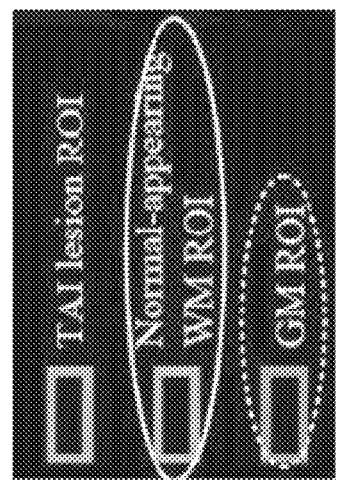
FIG. 16C
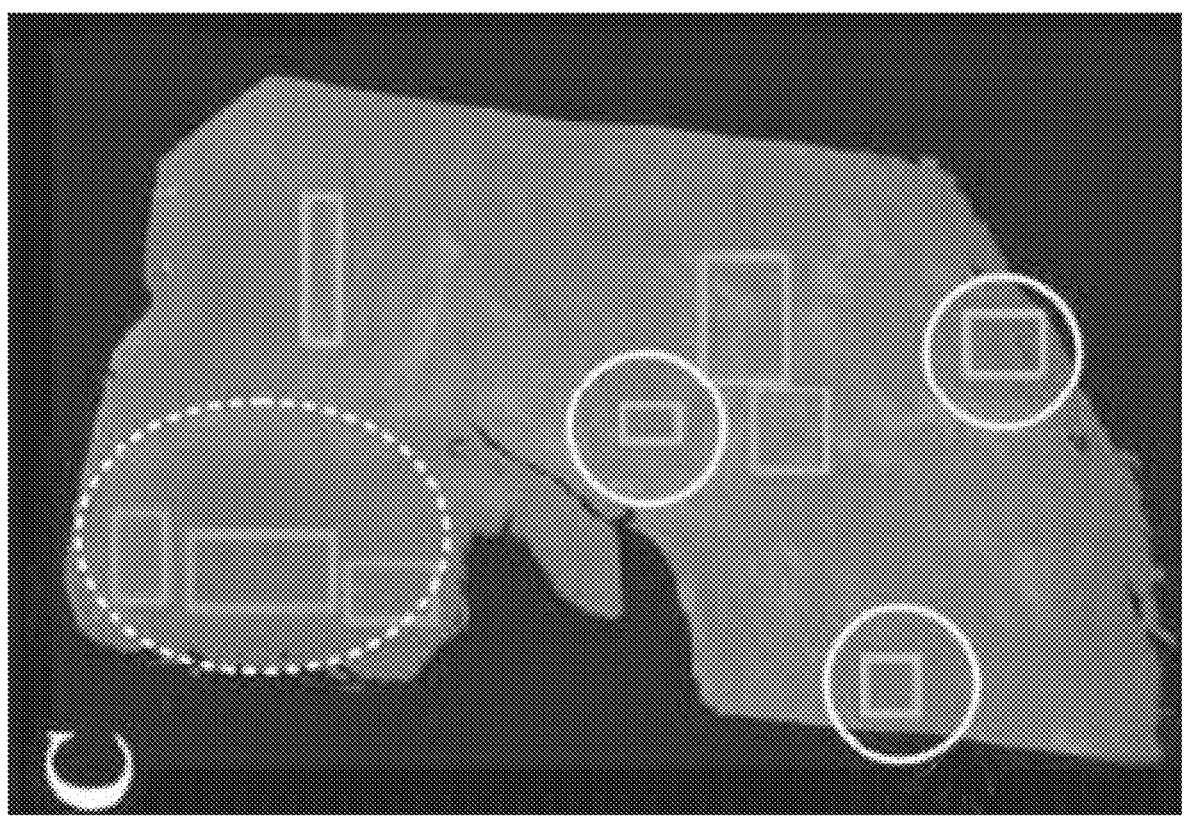

Main demographic and histopathological findings in TAI patients and controls

| Case # | Age | Sex | Cause of Death | Post-mortem Interval (h) | Survival time | Relevant Medical History |
|---|---|---|---|---|---|---|
| 1 | 70 | M | Possible fall/MVA | <12 | 3 d | Alcohol abuse, depression, diabetes mellitus |
| 2 | 60 | M | MVA | <12 | 26 d | N/A |
| 3 | 33 | M | MVA | 30 | N/A | Cholecystectomy, anxiety |
| 4 | 49 | M | Fall | <12 | 16 h | N/A |
| 5 | 23 | F | Possible MVA | <12 | 5 d | N/A |
| 6 | 36 | M | Suicide | <12 | >1 yr | Anxiety, paranoia, depression, psychosis |
| 7 | 58 | M | Cirrhosis | <12 | >1 yr | Alcohol abuse, drug abuse, fall |
| 8 | 32 | M | Possible suicide | 12 | >1 yr | MVA, severe headache, cholecystectomy, hypertension |
| 9 | 52 | M | Cardiac arrest | 19 | N/A | N/A |
| 10 | 44 | M | Cardiac arrest | 22 | N/A | N/A |
| 11 | 54 | M | Cardiac arrest | 29 | N/A | N/A |

FIG. 17A

Main demographic and histopathological findings in TAI patients and controls

| Clinical Diagnosis | DAI Grade | Microscopically confirmed TAI in CC, APP-positive | |
|---|---|---|---|
| | | Extent | Severity, Left/Right (+; ++; +++) |
| Fatal | II | Bilateral | +++/+ |
| Fatal | II | Bilateral | +/+ |
| Fatal | I | Bilateral | +/+ |
| Fatal | III | Bilateral | +/+ |
| Fatal | II | Unilateral (right) | 0/+ |
| Nonfatal | I | Unilateral (right) | N/A/++ |
| Nonfatal | II | Unilateral (left) | +/0 |
| Nonfatal | I | Unilateral (right) | 0/+ |
| Control | N/A | Absent | 0/ N/A |
| Control | N/A | Absent | 0/0 |
| Control | N/A | Absent | 0/0 |

FIG. 17B

| Variable | Control, m=3 | Nonfatal TBI, m=3 | Fatal TBI, m=5 |
|---|---|---|---|
| Median age, years (IQR) | 52.0 (46.4, 53.6) | 360.0 (32.5, 51.4) | 49.0 (34.1, 59.9) |
| Median brain weight, gr (IQR) | 1294 (1268, 1623) | 1469 (1361, 1572) | 1540 (1512, 1642) |
| Mean post-mortem interval, hours (SD) | 23.4 (4.9) | 12.0 (0.0) | 15.3 (7.6) |
| DAI grade, II | N/A | 1 (33%) | 3 (60%) |
| APP-based TAI severity (in more severe side), + | N/A | 2 (66%) | 4 (80%) |
| APP-based TAI extent, bilateral | N/A | 0 (0%) | 4 (80%) |

[a]Mann-Whitney U-test; [b]unpaired two-tailed Student's t-test; [c]Fisher exact test

FIG. 17C

| Control vs. Nonfatal TBI | | Control vs. Fatal TBI | | Fatal TBI vs. Nonfatal TBI | |
|---|---|---|---|---|---|
| P | | P | | P | |
| 0.700 | | 1.000 | | 0.786[a] | |
| 0.700 | | 0.571 | | 0.393[a] | |
| 0.057 | | 0.121 | | 0.386[b] | |
| N/A | | N/A | | 0.220[b] | |
| N/A | | N/A | | 0.588[b] | |
| N/A | | N/A | | 0.1429[c] | |

[a]Mann-Whitney U-test; [b]unpaired two-tailed Student's t-test; [c]Fisher exact test

FIG. 17D

Comparisons of voxel-averaged, multidimensional sROI-averaged MRI parameters, and pathological measures among control VM and TAI tissue blocks.

| Case # | % area APP | Voxel-averaged | sROI | Voxel-averaged |
|---|---|---|---|---|
| 1 | 21.63 (4.38) *** | 331.33 (36.10) ** | 213.32 (18.82) *** | 48.72 (7.17) + |
| 2 | 15.67 (2.59) *** | 278.82 (10.29) *** | 193.41 (6.19) *** | 37.32 (2.69) * |
| 3 | 29.85 (11.56) *** | 318.18 (26.74) *** | 211.44 (13.36) *** | 33.80 (3.00) *** |
| 4 | 52.69 (11.74) *** | 268.76 (4.49) *** | 202.82 (7.26) *** | 35.25 (0.67) *** |
| 5 | 19.91 (10.1) ** | 248.61 (19.35) *** | 248.54 (31.83) * | 36.77 (2.76) ** |
| 6 | 13.42 (3.39) *** | 400.67 (7.52) + | 301.00 (3.15) + | 44.01 (0.79) + |
| 7 | 13.21 (2.08) *** | 387.39 (7.76) + | 276.08 (4.54) + | 44.73 (1.24) * |
| 8 | 28.9 (8.12) *** | 349.26 (2.51) ** | 242.21 (1.78) ** | 37.13 (1.17) *** |
| 9 | 1.10 (0.76) | 378.78 (7.65) | 258.56 (5.50) | 42.37 (0.25) |
| 10 | 0.53 (0.13) | 464.81 (6.54) | 330.6 (3.15) | 40.77 (0.76) |
| 11 | 0.15 (0.12) | 450.76 (4.94) | 336.65 (1.25) | 43.81 (0.75) |

+ - not significant; *p<0.05; p<0.01; *p<.001; (unpaired two-tailed Student's t-test, compared with mean control values.)

FIG. 18A

Comparisons of voxel-averaged, multidimensional sROI-averaged MRI parameters, and pathological measures among control VM and TAI tissue blocks.

| sROI | Voxel-averaged | sROI | FA |
|---|---|---|---|
| 19.66 (0.45) *** | 0.19 (0.01) + | 0.06 (0.01) *** | 0.22 (0.05) + |
| 22.82 (2.75) * | 0.26 (0.09)* | 0.07 (0.01) + | 0.11 (0.02) * |
| 19.25 (1.16) *** | 0.18 (0.02) + | 0.07 (0.02) + | 0.32 (0.05) + |
| 19.63 (0.76) *** | 0.24 (0.01) ** | 0.08 (0.01) + | 0.27 (0.01) + |
| 27.09 (1.95) + | 0.24 (0.03) * | 0.06 (0.01) ** | 0.14 (0.03) * |
| 27.96 (0.15) + | 0.20 (0.02) + | 0.09 (0.01) * | 0.33 (0.06) + |
| 23.97 (0.69) * | 0.20 (0.01) + | 0.10 (0.01) *** | 0.41 (0.04) + |
| 25.27 (0.84) + | 0.20 (0.01) + | 0.05 (0.01) *** | 0.50 (0.01) * |
| 26.01 (2.14) | 0.15 (0.02) | 0.08 (0.01) | 0.21 (0.04) |
| 27.56 (0.89) | 0.21 (0.01) | 0.08 (0.01) | 0.41 (0.08) |
| 29.11 (0.58) | 0.17 (0.01) | 0.07 (0.01) | 0.36 (0.05) |

+ – not significant; *$p<0.05$; $p<0.01$; *$p<.001$; (unpaired two-tailed Student's t-test, compared with mean control values.)

FIG. 18B

Comparisons of MRI parameters and pathological measures among healthy control WM, mild TAI (mTAI), and severe TAI (sTAI) tissue blocks.

| Variable | Healthy Control WM n=24 mean (SE) | mTAI n=12 mean (SE) | sTAI n=20 mean (SE) | mTAI vs Healthy Control WM Estimated mean difference (95% CI) | $p$ / $p_{FDR}$ | sTAI vs Healthy Control WM Estimated mean difference (95% CI) | $p$ / $p_{FDR}$ |
|---|---|---|---|---|---|---|---|
| T1-T2 SC, x100 | 1.29 (0.29) | 4.09 (0.97) | 4.70 (1.03) | 2.80 (0.81, 4.78) | 0.007 / 0.024 | 3.41 (1.31, 5.51) | 0.002 / 0.007 |
| ⟨D⟩-T1 SC, x100 | 1.28 (0.59) | 0.41 (0.20) | 2.20 (0.64) | -0.87 (-2.09, 0.35) | 0.167 / 0.318 | 0.92 (-0.79, 2.63) | 0.294 / 0.483 |
| ⟨D⟩-T2 SC, x100 | 0.38 (0.17) | 1.14 (0.24) | 2.84 (0.65) | 0.76 (0.18, 1.34) | 0.013 / 0.035 | 2.46 (1.14, 3.78) | <0.001 / 0.002 |
| FA | 0.33 (0.06) | 0.35 (0.09) | 0.25 (0.04) | 0.02 (-0.19, 0.23) | 0.861 / 0.907 | -0.08 (-0.22, 0.06) | 0.266 / 0.483 |
| ADC [um²/ms] | 0.17 (0.01) | 0.21 (0.01) | 0.22 (0.02) | 0.04 (0.01, 0.07) | 0.020 / 0.044 | 0.05 (-0.01, 0.09) | 0.023 / 0.048 |
| T1 [ms] | 430.78 (21.60) | 328.42 (33.91) | 319.55 (20.94) | -102.36 (-181.16, -23.56) | 0.012 / 0.035 | -111.23 (-170.19, -52.27) | <0.001 / 0.002 |
| T2 [ms] | 42.01 (1.40) | 39.54 (2.67) | 39.82 (2.53) | -2.47 (-8.38, 3.44) | 0.415 / 0.577 | -2.19 (-7.86, 3.48) | 0.450 / 0.600 |
| % area APP | 0.37 (1.41) | 20.67 (3.71) | 26.65 (6.35) | 20.30 (12.52, 28.08) | <0.001 / <0.001 | 26.28 (13.53, 39.03) | <0.001 / <0.001 |

FIG. 18C

Comparisons of MRI parameters and pathological measures among normal-appearing sTAI and mTAI and mTAI WM, mild TAI (mTAI), and severe TAI (sTAI) tissue blocks.

| Variable | Normal-appearing mTAI WM n=12 mean (SE) | mTAI n=12 mean (SE) | Normal-appearing sTAI WM n=20 mean (SE) | sTAI n=20 mean (SE) | mTAI vs Normal-appearing mTAI WM Estimated mean difference (95% CI) | $P$ $P_{FDR}$ |
|---|---|---|---|---|---|---|
| T1-T2 SC, x100 | 1.09 (0.39) | 4.09 (0.97) | 0.67 (0.29) | 4.70 (1.03) | 3.00 (0.95, 5.05) | >0.001 0.003 |
| <D>-T1 SC, x100 | 0.56 (0.29) | 0.41 (0.20) | 0.46 (0.19) | 2.20 (0.64) | -0.15 (-0.84, 0.54) | 0.708 0.809 |
| <D>-T2 SC, x100 | 0.22 (0.24) | 1.14 (0.24) | 0.19 (0.19) | 2.84 (0.65) | 0.92 (0.25, 1.58) | 0.009 0.028 |
| FA | 0.37 (0.04) | 0.35 (0.09) | 0.27 (0.03) | 0.25 (0.04) | -0.02 (-0.21, 0.17) | 0.827 0.894 |
| ADC [um²/ms] | 0.21 (0.01) | 0.21 (0.01) | 0.19 (0.01) | 0.22 (0.02) | 0.00 (-0.03, 0.03) | 0.623 0.755 |
| T1 [ms] | 328.42 (33.91) | 328.42 (33.91) | 337.30 (22.64) | 319.55 (20.94) | -8.59 (-98.87, 81.69) | 0.530 0.684 |
| T2 [ms] | 42.86 (1.93) | 39.54 (2.67) | 43.60 (2.86) | 39.82 (2.53) | -4.06 (-11.73, 3.61) | 0.108 0.215 |
| % area APP | 0.40 (1.99) | 20.67 (3.71) | 0.97 (1.54) | 26.65 (6.35) | 20.27 (12.02, 28.52) | <0.001 <0.001 |

FIG. 18D

Comparisons of MRI parameters and pathological measures among normal-appearing sTAI and mTAI and mTAI WM, mild TAI (mTAI), and severe TAI (sTAI) tissue blocks.

| | sTAI vs Normal-appearing sTAI WM | | sTAI vs mTAI | |
|---|---|---|---|---|
| | Estimated mean difference (95% CI) | P / P_FDR | Estimated mean difference (95% CI) | P / P_FDR |
| | 4.03 (1.93, 6.13) | >0.001 / 0.001 | 0.74 (1.93, 3.41) | 0.586 / 0.670 |
| | 1.74 (0.43, 3.05) | 0.018 / 0.042 | 1.57 (0.24, 2.90) | 0.017 / 0.052 |
| | 2.65 (1.32, 3.98) | >0.001 / >0.001 | 1.72 (0.36, 3.08) | 0.014 / 0.048 |
| | -0.02 (-0.12, 0.08) | 0.612 / 0.755 | 0.00 (-0.18, 0.18) | 0.979 / 0.979 |
| | 0.03 (-0.01, 0.07) | 0.290 / 0.483 | -0.01 (-0.05, 0.03) | 0.322 / 0.483 |
| | -17.75 (-78.19, 42.69) | 0.373 / 0.553 | -6.67 (-73.04, 59.70) | 0.770 / 0.803 |
| | -3.04 (-9.27, 3.20) | 0.369 / 0.553 | 2.94 (-3.72, 9.60) | 0.382 / 0.539 |
| | 25.68 (12.87, 38.49) | <0.001 / 0.001 | 5.96 (-8.45, 20.37) | 0.419 / 0.559 |

FIG. 18E

| Variable | Control WM n=24 mean (SE) | mTAI vs. Control WM | | sTAI vs. Control WM | |
|---|---|---|---|---|---|
| | | Estimated mean difference (95% CI) | $P_{FDR}$ | Estimated mean difference (95% CI) | $P_{FDR}$ |
| T1-T2 SC, x100 | 0.78 (0.24) | 3.31 (1.35, 5.27) | 0.001 0.005 | 3.92 (1.85, 5.99) | <0.001 <0.001 |
| \<D>-T1 SC, x100 | 0.52 (0.14) | -0.11 (-0.57, 0.32) | 0.644 0.736 | 1.68 (0.40, 2.96) | 0.011 0.023 |
| \<D>-T2 SC, x100 | 0.21 (0.17) | 0.93 (0.35, 1.51) | 0.002 0.005 | 2.63 (1.31, 3.95) | <0.001 <0.001 |
| Adjusted FA | 1.00 (0.05) | -0.06 (-0.53, 0.40) | 0.790 0.790 | -0.04 (-0.36, 0.27) | 0.789 0.789 |
| Adjusted MD | 1.00 (0.05) | 0.04 (-0.12, 0.20) | 0.628 0.718 | 0.13 (-0.10, 0.36) | 0.254 0.406 |
| Adjusted T1 | 1.00 (0.02) | -0.03 (-0.10, 0.04) | 0.448 0.717 | -0.04 (-0.17, 0.09) | 0.519 0.593 |
| Adjusted T2 | 1.00 (0.03) | -0.09 (-0.19, 0.01) | 0.077 0.155 | -0.06 (-0.23, 0.11) | 0.492 0.593 |
| % area APP | 0.18 (1.41) | 20.49 (12.71, 28.27) | <0.001 <0.001 | 26.46 (13.71, 39.22) | <0.001 <0.001 |

Spectral component (SC); Fractional anisotropy (FA); mean diffusivity (MD)

FIG. 19A

| | Normal-appearing WM in mTAI vs. Control WM | | Normal-appearing WM in sTAI vs. Control WM | |
|---|---|---|---|---|
| Estimated mean difference (95% CI) | Estimated mean difference (95% CI) | $P_{FDR}$ | Estimated mean difference (95% CI) | $P_{FDR}$ |
| | 0.31 (-0.59, 1.21) | 0.502 / 1.000 | 0.11 (-0.85, 0.63) | 0.502 / 1.000 |
| | 0.04 (-0.59, 0.67) | 0.887 / 1.000 | -0.06 (-0.52, 0.40) | 0.887 / 1.000 |
| | 0.01 (-0.57, 0.59) | .958 / 1.000 | -0.02 (-0.52, 0.48) | 0.958 / 1.000 |
| | 0.00 (-0.15, 0.15) | 1.000 / 1.000 | 0.00 (-0.13, 0.13) | 1.000 / 1.000 |
| | 0.00 (-0.16, 0.16) | 1.000 / 1.000 | 0.00 (-0.13, 0.13) | 1.000 / 1.000 |
| | 0.00 (-0.07, 0.07) | 1.000 / 1.000 | 0.00 (-0.06, 0.06) | 1.000 / 1.000 |
| | 0.00 (-0.10, 0.10) | 1.000 / 1.000 | 0.00 (-0.09, 0.09) | 1.000 / 1.000 |
| | 0.22 (-4.56, 5.00) | 0.929 / 1.000 | 0.79 (-3.30, 4.87) | 0.929 / 1.000 |

Spectral component (SC); Fractional anisotropy (FA); mean diffusivity (MD)

FIG. 19B

MULTIDIMENSIONAL MRI SIGNATURE FOR SPECIFIC DETECTION OF TRAUMATIC BRAIN INJURY IN VIVO

STATEMENT OF GOVERNMENT SUPPORT

This invention was made with Government support under project number Z01 #: 1 ZIA HD008971 01 by the National Institutes of Health, Eunice Kennedy Shriver National Institute of Child Health and Human Development (NICHD). The United States Government has certain rights in the invention.

CROSS-REFERENCE TO RELATED APPLICATIONS

This application is a U.S. National Phase of International Application No. PCT/US2021/041663, filed on Jul. 14, 2021, which claims priority to U.S. Provisional Application 63,061,105, filed Aug. 4, 2020, each of which is incorporated herein by reference in their entireties.

FIELD OF THE DISCLOSURE

The disclosure pertains to magnetic resonance methods for detected injury, particularly traumatic brain injury.

BACKGROUND

Traumatic brain injury (TBI) represents a major medical, social and economic concern across countries due to its association with death—especially among the younger populations—and long-term disabilities. Among the various pathological brain lesions (e.g. intracerebral bleedings, necrotic-ischemic lesions, tissue avulsion) produced by impacting mechanical forces, diffuse axonal injury (DAI) has been one of the brain lesions typically associated with a traumatic event. While DAI is frequently observed in TBI, it is not necessarily linked with TBI exposure and as discussed, herein, the term "traumatic axonal injury (TAI)" is used, which is a specific form of DAI consequent to TBI.

TAI is defined as the pathologic accumulation of different possible proteins inside the axonal spaces caused by the physical distortions of axons and their cytoskeleton structures due to a cranial-facial mechanical loading sudden impact. TAI is most frequently neuroanatomically localized along the different portions of the Corpus Callosum (CC), especially at level of its more anterior portion. The preferential localization of TAI in the CC is due to both the physical localization of this anatomical structure as well as to the abundance of myelinated axons projecting across all cerebral cortical regions. While TAI identification and quantification methods investigations are very important topics for current in-vivo magnetic resonance imaging (MRI) studies, there are unfortunately few neuroimaging-pathological correlation studies that have had the chance to verify pathologic nature, histological distribution and level of severity of brain lesions detected by MRI images after an acute TBI exposure, including TAI.

Computed tomography (CT) and conventional MRI cannot adequately depict brain injury at the neuronal level because their spatial sensitivity is usually above 400 μm. This technical limitation is of special relevance in cases of mild TBI (mTBI), where, among other consequences, sparse clusters of neurons and connected axons are possibly affected and that are dislocated far apart across different parts of the brain as well as inside the same neuroanatomical regions (e.g., CC). Diffusion MRI (dMRI) is a technique that provides higher spatial sensitivity for changes that are in the order of the tissue environment (below 100 μm) by using water mobility as a probe of tissue microstructure. The most established dMRI framework, diffusion tensor imaging (DTI) provides the macroscopic orientationally averaged diffusivity and diffusion anisotropy of water in tissues, mean diffusivity (MD) and the fractional anisotropy (FA), respectively. Since its first use to investigate DAI in mTBI, DTI had been established as a sensitive tool for detecting the subtle tissue alterations following these types of injury and FA had stood out as a sensitive metric for mTBI detection. Unfortunately, while there is no dispute regarding DTI's sensitivity, conflicting observations of both decreases and increases of the FA in mTBI groups compared with controls have been reported, which indicate DTI's inherent lack of specificity towards mTBI.

However, an additional, more fundamental impediment of all MRI approaches that have been used to detect and assess mTBI to date is that they provide information averaged over the entire voxel. Voxel-averaged scalar images can only provide macroscopic information with respect to the voxel size (typically on the order of 1 $mm^3$), limited by MRI's relatively low spatial resolution. In most cases in the brain, an individual voxel will contain multiple chemical and physical microenvironments, attributable to water in axons, neurons, glia, myelin, and in cerebrospinal fluid (CSF). In the case of mild TAI (mTAI), the injured axons would occupy only a very small volume of a given voxel and would most likely remain undetectable using voxel-averaged MRI approaches. As a result, the inability to separate normal and pathological tissue within a voxel is the most likely cause of the non-specificity of conventional MRI methods, including DTI, towards mTBI. For at least these reasons, improved approaches are needed.

SUMMARY OF THE DISCLOSURE

The disclosure pertains to noninvasive methods of assessing nervous system injury, particularly traumatic brain injury (TBI), including mild TBI. A unique TAI multidimensional spectral signature can be measured and used to generate TAI biomarker images that closely follow APP histopathology: APP-positive areas scale with multidimensional TAI biomarker intensity and negative APP corresponds to reduced or complete lack of MRI signal. This specificity of the multidimensional TAI biomarkers permits so-called "noninvasive histology." One or more T1-T2-MD ranges can be identified and specifically linked to TAI microscopic tissue alterations. Because T1, T2, and diffusion dynamics can be different in fixed tissue compared with living systems, different T1-T2-MD ranges can be selected for fixed and living tissues.

Disclosed herein are multidimensional MRI-based methods that permit identification and categorization of CC specimens to identify sub-voxel tissue components that are specific to TAI lesions. Other specimens can be evaluated similarly, and CC is selected as an important practical example. In typical examples, multidimensional MR data is acquired and processed using the MADCO framework in which partial multidimensional spectral data is acquired and processed to provide complete multidimensional data. For example, partial two dimensional data sets such as T1-T2, MD-T2, and MD-T1 data sets can be combined to provide a complete three dimensional data set. Partial data sets of a lower dimension are combined to produce a complete data set of a higher dimension. While MADCO is not required, the MADCO approach permits substantial reductions in data acquisition time and can enable in vivo data acquisition.

Methods comprise selecting a portion of at least one multi-dimensional magnetic resonance (MR) spectrum associated with a specimen and retrieving a spectral signature. Based on the selected portion and the spectral signature, at least one specimen location is characterized. In some examples at least a first data value is assigned to the at least one specimen location based on the categorization. Typically, the first data value is assigned based on a combination of spectral values in the selected portion of at the least one multi-dimensional MR spectrum and a weight included in the spectral signature. In some cases, the at least one specimen location corresponds to a plurality of voxels and each of the plurality of voxels is categorized and the plurality of voxels corresponds to at least a portion of a specimen image. Typically, a categorized image is formed and displayed based on the specimen image and the categorization. In some examples, the multi-dimensional MRI spectrum associated with the specimen is based on partial multi-dimensional MRI spectra of lower dimension. In a representative application, the specimen includes a portion of a brain and the categorization is based on an indication of brain injury. In typical examples, the selected portion of the multi-dimensional MRI spectrum is a T1-T2 spectrum and the locations associated with each of the voxels based are characterized based on a combination of spectral values in the selected portion of at the least one multi-dimensional MR spectrum and image is displayed based on the categorization. In further examples, the selected portion of the multi-dimensional MRI spectrum is a T1-MD, a T2-MD spectrum, a T1-T2-MD spectrum or a spectrum based on any combination of $D_{iso}$, $D_\Delta$, $\theta$-$\phi$, $T_1$, $T_2$, and FA.

Methods comprise identifying a reference portion of a multidimensional MR spectrum associated with brain injury and receiving a corresponding multidimensional MR spectrum of a sample. A spectral signature associated with the reference portion is retrieved from a library, and the sample is characterized based on a comparison of the identified portion and a corresponding portion of the multidimensional MR spectrum of the sample. In some examples, the multidimensional MR spectra are one or more of T1-T2, T1-MD, T2-MD, or T1-T2-MD or any combination of T1-T2-MD, $D_{iso}$, $D_\Delta$, ($\theta$, $\phi$) spectra. In some examples, the comparison is based on combinations of spectral values in the reference portion of a multidimensional MR spectrum and the multi-dimensional MR spectrum of the sample. In specific examples, the reference portion of the multidimensional MR spectrum is defined by a T1 range, a T2 range, and an MD range. In one examples, the T1 range is about 90 ms to 350 ms, the T2 range is about 6 to 40 ms, and the MD range is about 0.004 to 0.150 μm²/ms.

Systems comprise an MRI apparatus operable to obtain partial MR spectra for a plurality of voxels for a specimen associated with brain injury. A memory stores at least a reference multidimensional MR spectral range. A processor is coupled to the MRI apparatus and operable to (1) produce a multidimensional spectrum associated with the specimen in at least the reference multidimensional spectral range, (2) assess brain injury based on portions of the multidimensional spectrum in the reference multidimensional spectral range using a weight based on spectral magnitudes in the reference multidimensional spectral range, and (3) produce a specimen injury displaying the assessment of brain injury. In one example, the reference multidimensional MR spectral range is defined by T1, T2, and MD ranges.

In some alternatives, a memory stores least one MR spectral signature associated with a corresponding multidimensional MR spectral range and a processor is coupled to an MRI apparatus and operable to assess brain injury based on the MR spectral signature and a correspond MR spectrum of a specimen. Typically a specimen image is displayed showing indications of brain injury.

The foregoing and other features and advantages of the disclosure will become more apparent from the following detailed description which proceeds with reference to the accompanying figures.

BRIEF DESCRIPTION OF THE FIGURES

FIG. TA illustrates a representative method of using multidimensional spectral data to identify sample characteristics.

As shown in FIGS. 12A-12C, respectively, the (A) T1-T2, (B) MD-T1, and (C) MD-T2 TAI SCs were then calculated in each voxel for each dataset and compared using Bland-Altman plots. High agreement between the two repeated acquisitions was observed for T1-T2, MD-T1, and MD-T2. Central lines in each figure correspond to a zero bias line and a mean difference line. Voxel values are shown with dots.

FIGS. 16A-16D show representative deconvolved histological images of various cases.

FIGS. 17A-17D are tables containing main demographic and histopathological findings.

FIGS. 18A-18E include tables of comparisons of MRI parameters.

FIGS. 19A-19B are tables of additional comparisons of MRI parameters and pathological measures.

DETAILED DESCRIPTION OF SEVERAL EMBODIMENTS

Figure 1A:
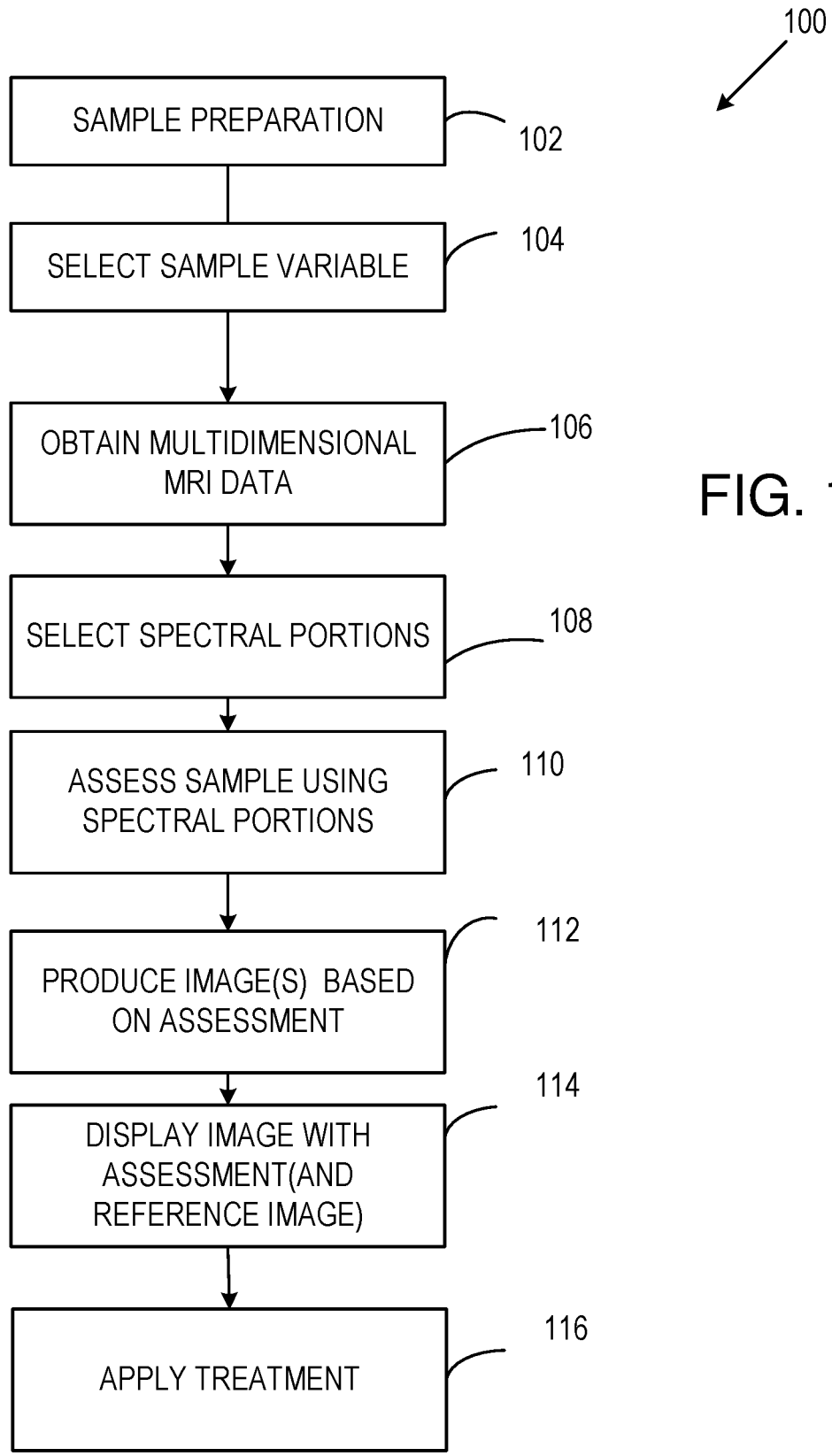
FIG. 1B illustrates a representative method of using T1-T2-MD spectrum to assess injury such as brain injury.
FIG. 1C illustrates selection of a portion of T1-T2-MD spectra (a signature or signature portion) for use in assessing injury.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation. For example, the methods disclosure herein can be based on differences between healthy and traumatized neurons such as mechanical failures that result in transport disruption that leads to accumulation of APP and other proteins, which causes local axonal swelling. As known T1 and T2 relaxation enhancers, proteins accumulate and affect the surrounding water by shortening their observed T1 and T2 values. However, the disclosed approaches are not limited to such a model of injury.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatus' are referred to as "lowest", "best", "minimum," or the like. It will be appreciated that such descriptions are intended to indicate that a selection among many used functional alternatives can be made, and such selections need not be better, smaller, or otherwise preferable to other selections. Examples are described with reference to directions indicated as "above," "below," "upper," "lower," and the like. These terms are used for convenient description, but do not imply any particular spatial orientation. In some practical examples, images of specimens are provided that include data associated with a plurality of voxels, but smaller portions such as portions corresponding to single voxels can be evaluated. As used herein, "image" refers to a visual display presented for viewing as well as associated image data in any form such as a data file in jpeg, tiff, bitmap or other format.

For convenience, some abbreviations used are listed below:
traumatic brain injury (TBI)
diffuse axonal injury (DAI)
traumatic axonal injury (TAI), a specific form of DAI consequent to TBI
mild TAI (mTAI)
severe TAI (sTAI)
magnetic resonance imaging (MRI)
computed tomography (CT)
diffusion MRI (dMRI)
diffusion tensor imaging (DTI)
fractional anisotropy (FA)
magnetic resonance imaging (MRI)
region of interest (ROI)
spectral region of interest (sROI)
spectral component (SC)
white matter (WM)
corpus callosum (CC)
mean diffusivity (MD)
amyloid precursor protein (APP)

Application of the disclosed methods and apparatus is discussed in detail below with reference to particular samples and specific measurement and analysis approaches. These are representative approaches to provide to further illustration, and are not intended to limit the disclosure to these approaches.

Upon identification and in some cases, classification of TBI as discussed below, one or more therapies can be applied. Representative examples include administration of the autophagy inhibitor 3-methyladenine, memantine, amantadine, levetiracetam, hemigramicidin nitroxides, glibenclamide, statins, methylphenidate, progesterone in combination with vitamin D, or others.

As used herein, the term "multidimensional spectra" and the like refer to multiple independent data values associated with one or more image pixels or voxels. For example, MR signal attenuations can be used to determined data values associated with T1, T2, MD, FA, or other specimen characteristics. Thus, for example, for a voxel V, data can be expressed as V(T1, T2, . . . ). Multidimensional approaches can encode several MR contrasts (such as T1, T2, and diffusion) and deliver a multidimensional distribution (spectrum) of those parameters within each voxel, thus providing: (1) a distribution instead of a mean, allowing identification of multiple components within a voxel, and (2) separation and identification of different components based on the multiple parameters. These multidimensional approaches can be used to assess specimens based on multiple portions of these spectra as described below. Portions of such spectra or one or more data values based on spectral values in the portions that are suitable for sample characterization can be referred to as "signatures." Typically, values within spectral parameter ranges define such spectral portions and are referred to in some cases as reference portions. Examples are described with reference to T1, T2, and MD, but other combinations of these or other spectral parameters can be used.

Multidimensional Spectral Specimen Characterization

A general approach is illustrated in FIG. 1A. Referring to FIG. 1A, a method 100 includes identifying suitable samples and processing the samples at 102, if needed, for MR measurement. At 104, sample variables for investigation are selected, such as T1, T2, T2*, MD, or others. At 106, multidimensional spectra are obtained for at least selected portions of the sample. The multidimensional spectra based on the selected variables can be obtained by varying selected acquisition parameters to suitably cover a multidimensional spectral range. However, such acquisitions can require long acquisition times, and data can be acquired effectively using the MADCO scheme as described in Benjamini and Basser, "Use of marginal distributions constrained optimization (MADCO) for accelerated 2D MRI relaxometry and diffusometry," *J. Magn. Reson.* 271: 40-45 (2016), Benjamini and Basser, "Multidimensional correlation MRI," *NMR Biomed* e4226 (2020), and Basser and Benjamini, U.S. Patent Publication 2019/0178964, all of which are incorporated by reference and referred to herein as "Benjamini." Use of this approach is discussed further in reference to the detailed example below. Generally, with this approach, multidimensional spectra are produced using spectra of lower dimension as constraints. For example, two one-dimensional spectra for sample variables V1 and V2 can be used to produce a two dimensional V1, V2 spectrum. At 108, one or more portions of the two dimensional spectrum are selected to be used in sample assessment. These portions can be referred to as a spectral signature or signatures. At 110, one or more portions of the sample are characterized based on the selected spectral portions. For example, one or more spectral magnitudes or a sum of all spectral magnitudes within the selected spectral portion can be used for some or all sample voxels. In this way, any sample portion can be assigned one or more numerical values based on the characterization. Spectral values greater than a threshold can be used, and spectral values can be scaled linearly, logarithmically, or otherwise. At 112, a sample image with characterization can be produced using the assigned numerical values. At 114, the sample image can be displayed with or without a reference sample image. The reference image can be any image that permits association of the characterization with structures in the specimen. Finally, at 116, for in vivo applications, a treatment can be specified.

Figure 1B:
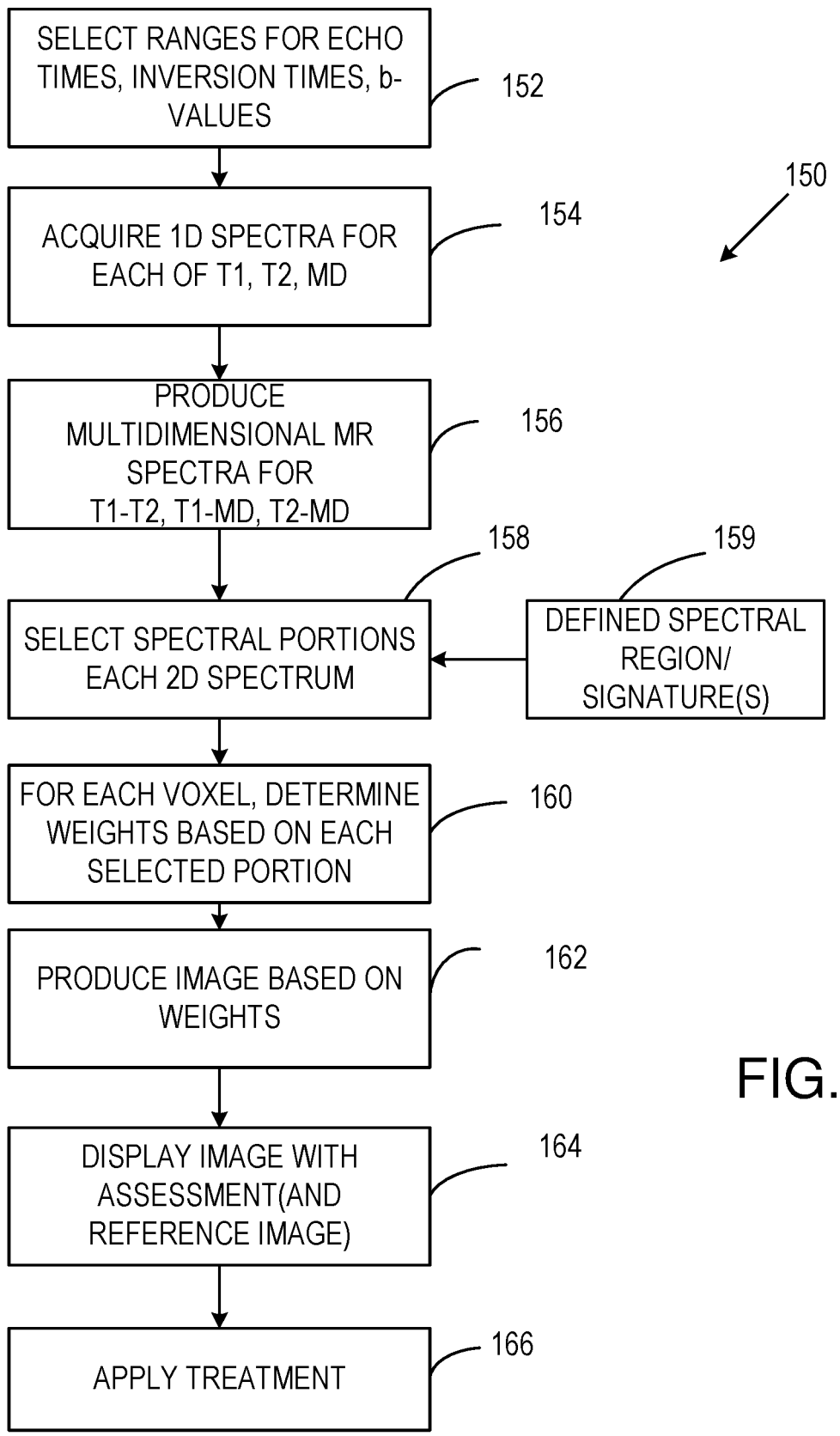
Figure 1C:
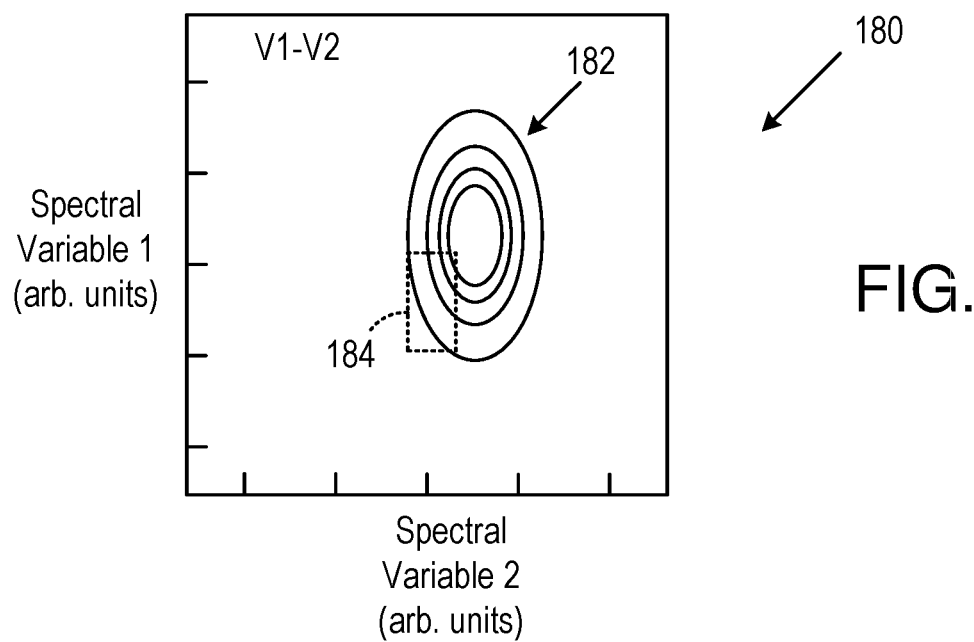

A particular example of the general approach of FIG. 1A can be described with reference to FIG. 1B which pertains to a method 150 based on T1, T2, and MD. Referring to FIG. 1B, at 152, suitable ranges for T1, T2, and MD are selected to provide measurements over a range at which samples can exhibit any changes or properties of interest. At 154, 1D spectra are obtained for each of T1, T2, and MD over all voxels of interest and at 156, 2D spectra are produced for each voxel for T1-T2, T1-MD, and T2-MD using the MADCO or other approach. At 158, portions of each (or some) of the 2D spectra are selected as pertinent to sample properties of interest. For example, referring to FIG. 1C, a 2D spectrum 180 for arbitrary variables V1, V2 (such as T1, T2 or T1, MD or T2, MD) is shown as a series of contours 182 corresponding to spectral magnitudes. A window 184 is identified for use in sample characterization. In some cases, spectral data is displayed with color values, but generally predetermined spectral windows can be used, and a spectrum is not displayed unless spectral windows are to be selected, modified, or evaluated. Returning to FIG. 1B, at 160, one or more weights are calculated for each voxel by summing spectral magnitudes within the window. The sums can be normalized so that values for all voxels are in a range of zero to one or other range. Sums for identified windows for each of the three 2D spectra can be summed as well, and normalized, if desired, or each voxel can be assigned three values, one associated with each of the 2D spectra or a single value based on a combination of the three values. At 162, a corresponding image (or images) is produced based on the characterizing sums which can be displayed at 164 with or without a reference image. At 166, a treatment can be selected and applied based on the image for in vivo applications.

Representative MR Measurement Apparatus

Figure 2:
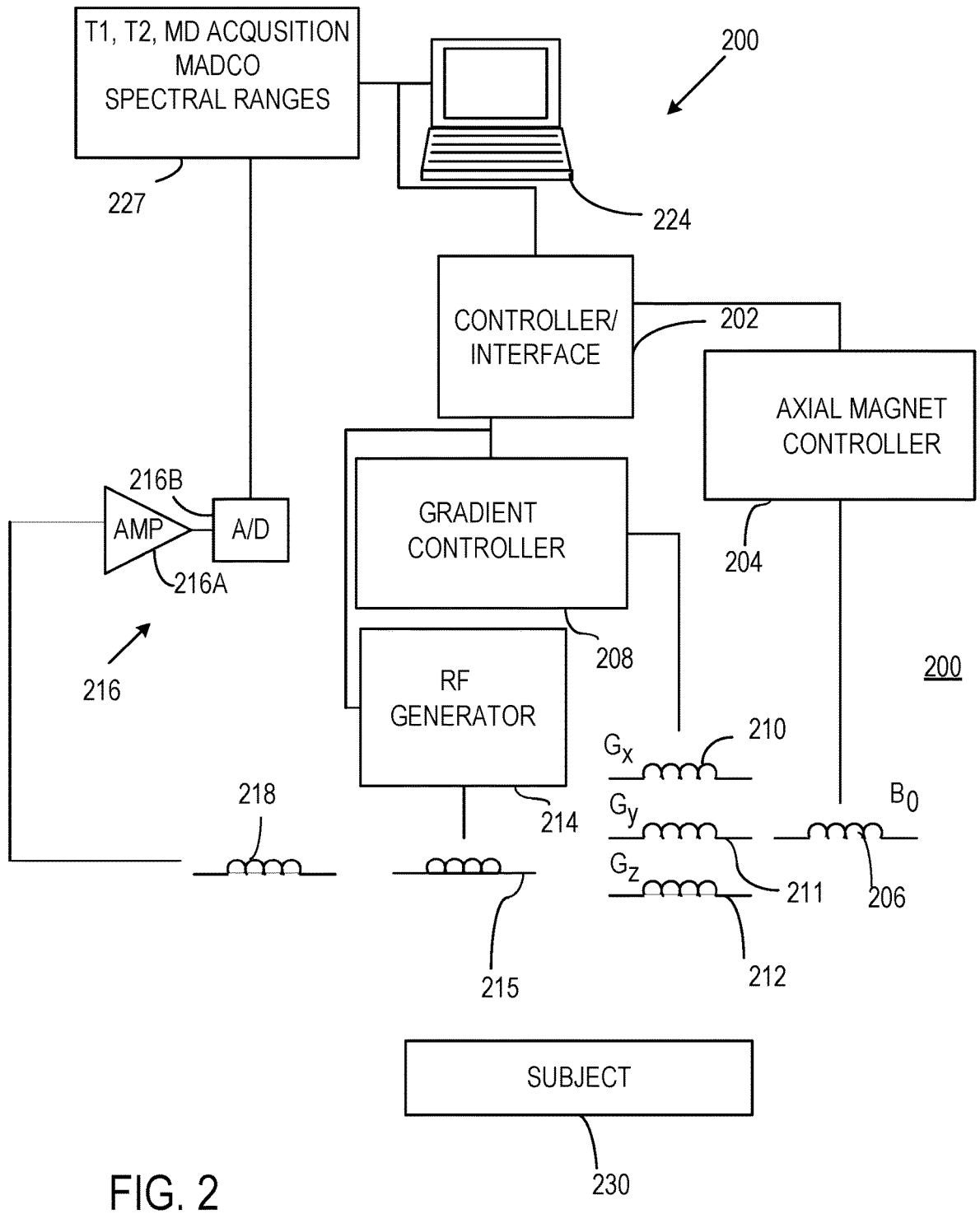
FIG. 2 illustrates a representative MR apparatus that can be used to obtain spectral data.

MR measurements as disclosed can be obtained using an MRI apparatus 200 as illustrated in FIG. 2. The apparatus 200 includes a controller/interface 202 that can be configured to apply selected magnetic fields such as constant or pulsed field gradients to a subject 230 or other specimen. An axial magnet controller 204 is in communication with an axial magnet 206 that is generally configured to produce a substantially constant magnetic field $B_0$. A gradient controller 208 is configured to apply a constant or time-varying magnetic field gradient in one or more selected directions or in a set of directions such as shown above using magnet coils 210-212 to produce respective magnetic field gradient vector components $G_x$, $G_y$, $G_z$ or combinations thereof to produce the gradients $G_1$, $G_2$ that are associated with b-matrices. An RF generator 214 is configured to deliver one or more RF pulses to a specimen using a transmitter coil 215. An RF receiver 216 is in communication with a receiver coil 218 and is configured to detect or measure net magnetization of spins. Typically, the RF receiver includes an amplifier 216A and an analog-to-digital convertor 216B that detect and digitize received signals to obtain MR signals. Slice selection gradients can be applied with the same hardware used to apply the diffusion gradients. The gradient controller 208 can be configured to produce pulses or other gradient fields along one or more axes as needed for a particular spectra.

For imaging, specimens are divided into volume elements (voxels) and MR signals for a plurality of gradient directions are acquired as discussed above, but signals can be acquired for one or only a few specimen voxels. In typical examples, signals are obtained for some or all voxels of interest. A computer 224 or other processing system such as a personal computer, a workstation, a personal digital assistant, laptop computer, smart phone, or a networked computer can be provided for acquisition, control and/or analysis of specimen data. The computer 224 generally includes a hard disk, a removable storage medium such as a floppy disk or CD-ROM, and other memory such as random access memory (RAM). Data can also be transmitted to and from a network using cloud-based processors and storage. Data could be uploaded to the Cloud or stored elsewhere. Computer-executable instructions for data acquisition or control and spectral computations can be provided on a floppy disk or other storage medium such as a memory 227, or delivered to the computer 224 via a local area network, the Internet, or other network. For example, the memory 227 can store one or more of processor-executable instructions for MADCO procedures, acquisition parameters, spectral signatures, or instructions or data for other procedures. Signal acquisition, instrument control, and signal analysis can be performed with distributed processing. For example, signal acquisition and signal analysis can be performed at different locations. Signal evaluation can be performed remotely from signal acquisition by communicating stored data to a remote processor. In general, control and data acquisition with an MRI apparatus can be provided with a local processor, or via instruction and data transmission via a network.

Example Measurements

Representative Specimens

To verify the disclosed approaches, brain autopsy specimens from two different human brain collections were assessed. Fixed segments of approximately 20×20×10 $mm^3$ of Corpus Callosum (CC) were obtained from four civilian subjects (referred to herein as cases 1, 2, 4, and 5), and seven military subjects (referred to herein as cases 3, 6-11). Next of kin provided written consent for participation and brain donation and Institutional Review Board (URB) approval was obtained prior to the initiation of the study. All experiments were performed in accordance with the relevant guidelines and regulations. A detailed description of demographics for the subjects from whom brain tissue samples were obtained is listed in Tables 1A-1B.

Specimen Preparation MRI Acquisition

Prior to MRI scanning, each brain specimen was transferred to a phosphate-buffered saline (PBS) filled container for 12 days to ensure that any residual fixative was removed from the tissue. The specimen was then placed in a 25-mm tube, and immersed in perfluoropolyether (Fomblin LC/8, Solvay Solexis, Italy), a proton free fluid void of a proton-MRI signal. Specimens were imaged using a 7 T Bruker vertical bore MRI scanner equipped with a microimaging probe and a 25 mm quadrupole RF coil.

Multidimensional data were acquired using a 3D inversion recovery spin-echo diffusion-weighted echo planar imaging (IR-DW-EPI) sequence with a repetition time of 1000 ms, and an isotropic voxel dimension of 300 µm. To encode the multidimensional MR space spanned by T1 and T2 (i.e., T1-T2), by T1 and diffusion (i.e., MD-T1), and by T2 and diffusion (i.e., MD-T2), 56, 223, and 223 images were acquired, respectively, according to a sampling scheme described in Pas et al., "Retaining information from multidimensional correlation MRI using a spectral regions of interest generator," *Sci. Rep.* 10:32462020 (2020) (hereinafter "Pas") which is incorporated herein by reference, with a total acquisition time of about 40 hr.

Acquisition of multidimensional data was done according to the MADCO framework encoding scheme as described in Benjamini and Basser, "Use of marginal distributions constrained optimization (MADCO) for accelerated 2D MRI relaxometry and diffusometry," *J. Magn. Reson.* 271: 40-45 (2016), Benjamini and Basser, "Multidimensional correlation MRI," *NMR Biomed* e4226 (2020), and Basser and Benjamini, U.S. Patent Publication 2019/0178964, all of which are incorporated by reference and referred to herein as "Benjamini." The following three experimental parameters were varied: the inversion time, $\tau_1$, the echo time, $\tau_2$, and the diffusion weighting, b. First, the three 1D distributions of T1, T2, and MD, were estimated, respectively, with the following data acquisition protocols: A 1D T1-weighted data set (b=0, $\tau_2$=11.1 ms) with 20 logarithmically sampled $\tau_1$ values ranging from 12 to 980 ms by using an IR-DWI-EPI sequence; a 1D T2-weighted data set (b=0) with 20 logarithmically sampled $\tau_2$ values ranging from 10.5 to 125 ms by using a DWI-EPI sequence. For diffusion encoding, the isotropic generalized diffusion tensor MRI (IGDTI) acquisition protocol was used to achieve an efficient orientationally averaged DW signal as described in Avram and Basser, PCT Patent Publication WO2018/187764 (hereinafter "Avram"), which is incorporated herein by reference. The following parameters were used: 16 linearly sampled b-values ranging from 2,540 to 14,700 s/mm$^2$ in 3 directions, 14 linearly sampled b-values ranging from 4,140 to 14,700 s/mm$^2$ in 4 directions, and 9 linearly sampled b-values ranging from 8,260 to 14,700 s/mm$^2$ in 6 directions, using the efficient gradient sampling schemes in Table 2 in Avram. Additional diffusion parameters were gradient duration of $\delta=4$ ms and diffusion time of $\Delta=15$ ms.

The three 2D distributions of MD-T1, MD-T2, and T1-T2, were estimated, respectively, with the following data acquisition protocols (in conjunction with the a priori obtained 1D distributions as constraints): A 2D D-T1-weighted data set with 16 sampled combinations of inversion times and values within the above 1D acquisition range; a 2D D-T2-weighted data set with 16 sampled combinations of echo times and b-values within the above 1D acquisition range; and a 2D T1-T2-weighted data set with 16 sampled combinations of inversion and echo times within the above 1D acquisition range. The sample temperature was set at 16.8° C. A standard DTI imaging protocol was applied with the same imaging parameters as the multidimensional data and using 21 diffusion gradient directions and four b-values ranging from 0 to 1400 s/mm$^2$. Lastly, a high-resolution MRI scan with an isotropic voxel dimension of 100 μm was acquired using a fast low angle shot (FLASH) sequence with a flip angle of 49.6° for co-registration of histopathological and MR images.

Verification with Histology and Immunohistochemistry

After MRI scanning, each CC tissue block was transferred for histopathological processing. All tissue blocks from each brain were processed using an automated tissue processor (ASP 6025, Leica Biosystems, Nussloch, Germany). After tissue processing, each tissue block was embedded in paraffin and cut in 5 μm-thick consecutive sections. The first two sections were selected for hematoxylin and eosin (H&E) and Luxol fast blue (LFB), while the remaining sections were selected for immunohistochemistry procedures using a Leica Bond III automated immunostainer with a diaminobenzidine chromogen detection system (DS9800, Leica Biosystems, Buffalo Grove, IL) staining for DAI [anti-amyloid precursor protein (APP)], microglia [anti-ionized calcium-binding adapter molecule 1 (Iba-1)], astrocytes [glial fibrillary acidic protein (GFAP)], and myelin [myelin basic protein (MBP)]. Two sections per antibody were stained at a distance of 300 μm apart from each other, in accordance with the MRI slice thickness.

All stained sections were scanned using an Aperio scanner system (Aperio AT2—High Volume, Digital whole slide scanning scanner, Leica Biosystems, Inc., Richmond, IL) and stored in Biolucida, a hub for 2D and 3D image data (MBF Bioscience, Williston, VT), for further assessment and analyses. A Zeiss Imager A2 (ImagerA2 microscope, Zeiss, Munich, Germany) bright-field microscope with ×40 and ×63 magnification lenses was used to identify and photograph histologic and pathologic details as needed.

Grading of the Injury

It is well recognized that either clinical and pathological aspects of TBI (i.e., closed head injury) are quite heterogeneous. Three separate classifications and gradings were used to evaluate the cases in this study. First, clinical outcome in which cases where a distinction was made based on whether the TBI was fatal or nonfatal. Second, the DAI grading was based on the original system proposed in Adams et al., "Diffuse axonal injury due to nonmissile head injury in humans: An analysis of 45 cases," Ann. Neurol. 12: 557-563 (1982) (hereinafter Adams and incorporated herein by reference) in which grading is based on axonal lesions positive for APP immunochemistry across the entire surface of the CC (APP-positive TAI lesions). The extent of the TAI lesions was also classified as unilateral or bilateral according to their presence in one or both hemispheres. Lastly, the levels of severity for TAI lesions were semi-quantitatively assessed based on their estimated load as occupying <50% (+), about 50% (++) or >50% (+++) of the microscopically examined section surface.

Quantification of Axonal Damage

Figure 3A:
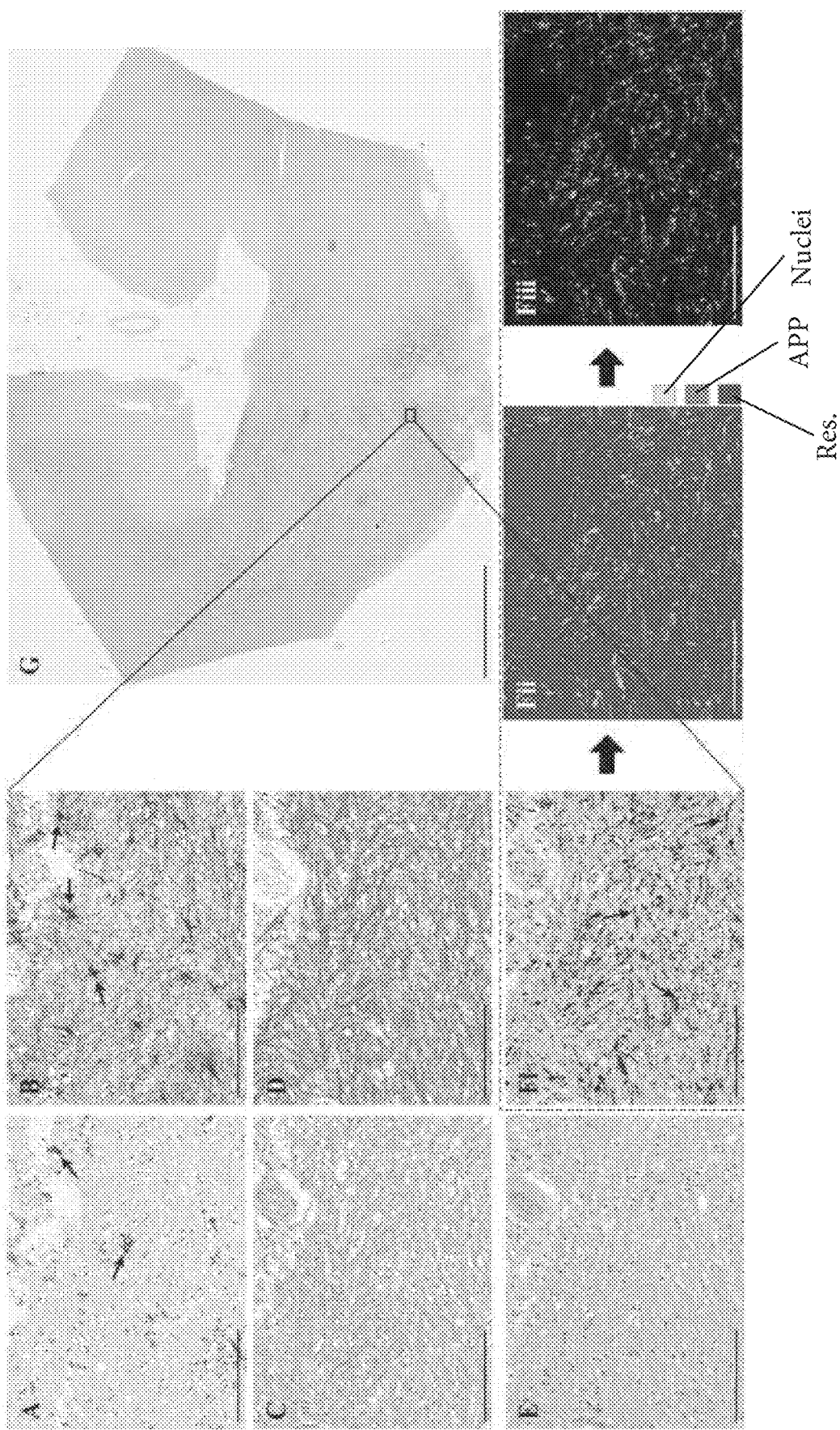
FIGS. 3A-3C detail histological findings from three representative Cases used to confirm the MR-based, multi-spectral approach. Case 1 (A-F), Case 2 (H-M), and Case 4 (O-T). Micrographs from approximately the same regions of (A, H, O) Ibal (microglia), (B, I, P) GFAP (astrocytes), (C, J, Q) Luxol fast blue (myelin), (D, K, R) MBP (myelin), (E, L, S) H&E. (Fi, Mi, Ti) original APP images, (Fii, Mii, Tii) which are deconvolved to obtain the APP density, in (Fiii, Miii, Tiii). Scalebar is 200 μm in all micrographs and 5 mm in the whole-mount corpus collosum APP images in G, N, and U.
Figure 3B:
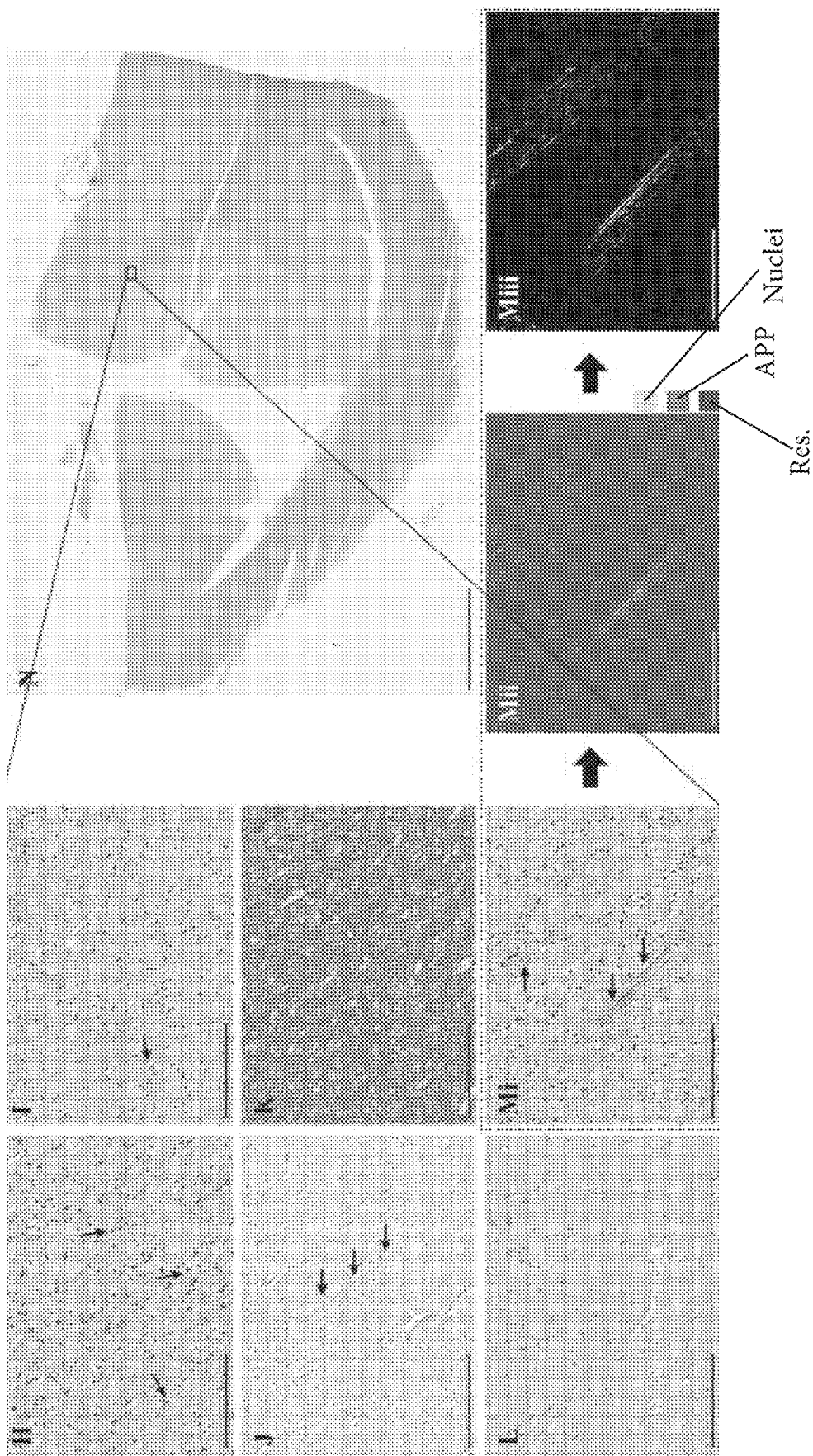
Figure 3C:
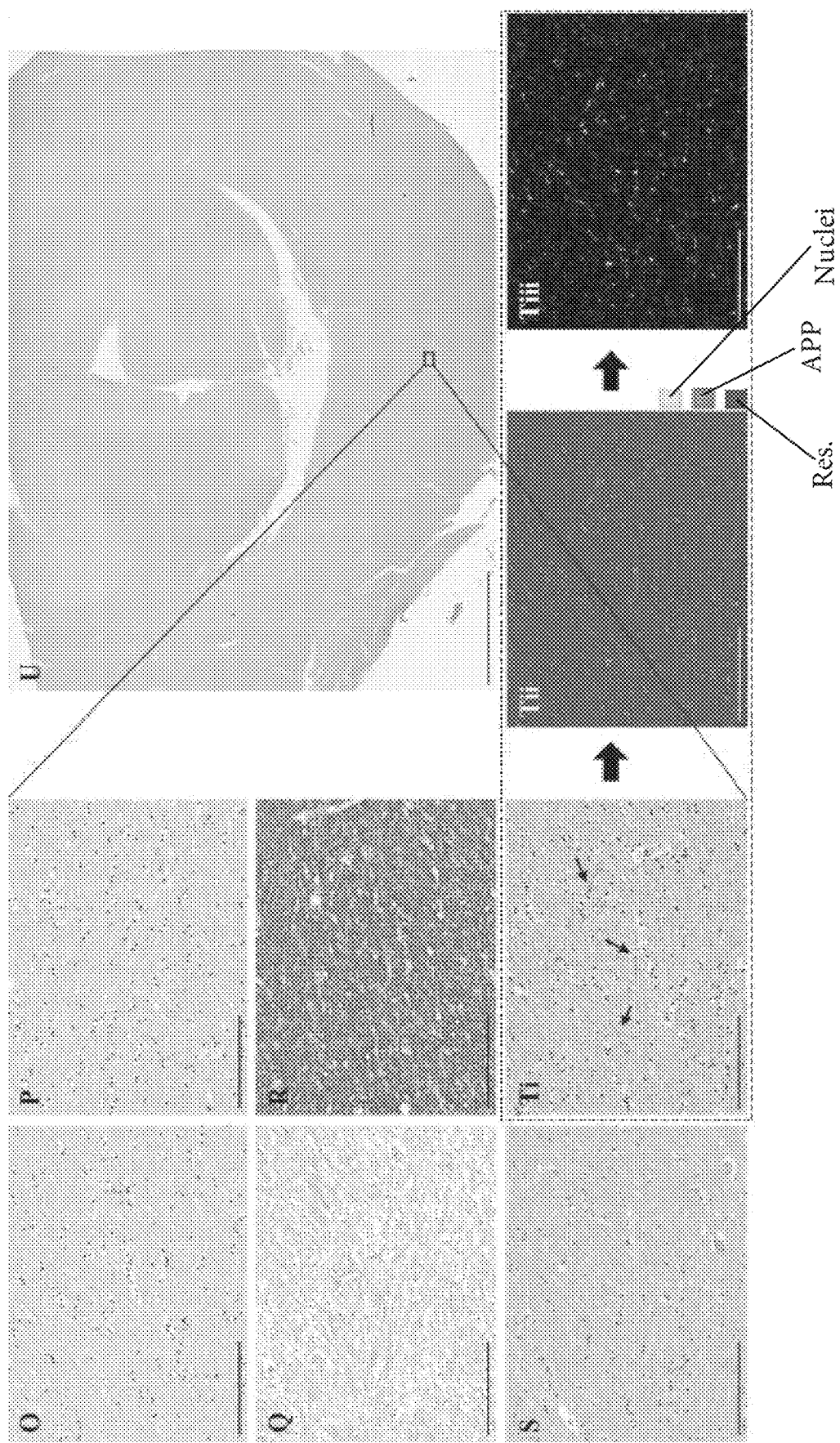

Images of APP stained sections were digitized using an Aperio whole slide scanning scanner system (Leica Biosystems, Richmond, IL) at ×20 magnification. The following steps, all implemented using MATLAB (The Mathworks, Natick, MA), were taken to allow for a quantitative analysis of the APP images. First, the images were transformed into a common, normalized space to enable improved quantitative analysis. Then, the normalized images were deconvolved to unmix the primary (APP) and secondary (H&E) stains, and background to three separate channels. Once an APP-only image was obtained, a final thresholding step was taken to exclude non-specific staining and to allow for a subsequent % area calculation. These steps are shown in FIGS. 3A-3C.

From each tissue section, based on APP staining, CC TAI lesions were identified as WM areas with swollen axonal varicosities, axonal bulbs, or distorted axons. Then, regions of interest (ROI) of normal-appearing WM and TAI lesions were defined. ROIs of normal WM from healthy control cases were defined as well. Additionally, cortical gray matter (GM) ROIs were defined in all sections. Twelve ROIs, covering together on average 81 mm$^2$ of tissue, were identified per tissue section. After extracting the ROIs, APP density was expressed as the percentage of total area within the ROI in the binary deconvolved APP image.

Diffusion Tensor MRI Processing

Diffusion tensor imaging parameters were calculated using in-house MATLAB (The Mathworks, Natick, MA) code.

Voxel-Averaged $T_1$ and $T_2$ Maps Processing

Conventional quantitative relaxation maps were first computed by fitting the signal decay to monoexponential functions. The $T_1$ value was computed by fitting a subset of the multidimensional data that included 20 images with inversion times in the range of 12 ms and 980 ms. The $T_2$ value was computed by fitting a subset of the multidimensional data that included 20 images with echo times in the range of 10.5 ms and 125 ms.

Multidimensional MRI Processing

A constrained, $L_2$ regularized, nonnegative least square optimization can be used to compute the multidimensional distribution in each voxel, as previously described in Benjamini and Pas. This produces three types of distributions in each voxel: T1-T2, MD-T2, and MD-T1. These multidimensional distributions can be considered as spectra and used to generate images of specific spectral components by integrating (summing) over a predefined parameter range (e.g., the rectangular T1-T2 range highlighted in FIGS. 4A-4C). The integral value is a number between 0 and 1, representing a certain spectral component (SC) in a given multidimensional distribution, which can be computed in each voxel to generate an image of that specific SC.

The T1-T2-MD spectra can contain rich information from multiple tissue components such as myelin. Based on the control and TAI cases examined herein, a T1-T2-MD range, (T1=[91.03, 339.32] ms, T2=[6.70, 34.85] ms, and MD= [0.004, 0.146]$\mu m^2$/ms) is identified in which primary spectral information regarding the injury resides. The mean distribution, averaged across all of the image voxels, was used to more accurately identify the TAI region in the spectra and to account for variability between different CC samples. An adaptive threshold can be used to detect the edge of the distribution within the identified T1-T2-MD range. That edge was set as the limit between the normal WM and the TAI lesions. Spectral values in the T1-T2-MD range form a spectral signature.

Histology-MRI Co-Registration

The high-resolution MR images were used as anatomical references to which the histological images were registered to. Areas in the histological images that grossly diverged from the wet tissue state (i.e., the MR images) due to deformation were manually removed, while maintaining the image aspect ratio. Following convergence of 2D affine co-registration of histology and MR images (Image Processing Toolbox, MATLAB, The Mathworks, Natick, MA), a 2D diffeomorphic registration refinement was performed between the APP image slices and MRI volumes. This was done in order to recover true in-plane tissue shape and bridge over residual differences between the modalities. The diffeomorphic registration procedure can be performed using an efficient implementation of the greedy diffeomorphic algorithm provided as an open-source software package. This implementation is optimized for computational speed, foregoing the symmetric registration model and implementing a highly optimized image resampling and metric computation.

Statistical Analysis

Demographic variables and post-mortem interval (i.e., time between death and start of autopsy) were compared between healthy controls, mTBI and sTBI patients (per clinical diagnosis) using Mann-Whitney U-test or unpaired two-tailed Student's t-test. For each TBI case, voxel- and sROI-averaged MRI parameters from TAI tissue blocks were compared with their corresponding values from healthy control WM tissue blocks using the unpaired two-tailed Student's t-test. Linear mixed-effects models were used to compare MRI-derived and histopathological measures among healthy control CC, normal-appearing WM in mTAI CC, normal-appearing WM in sTAI CC, DAI lesions in mTAI CC, and DAI lesions in sTAI CC, accounting for the hierarchical data structure. Random effects were added to model the within-subject correlation among histological samples, even in relation to the tissue type. False discovery rate (FDR) correction was carried out to take the overall number of pairwise contrasts into account.

The potential correlation between all of the conventional voxel-averaged and multidimensional MRI measures and APP density in the different tissue types was investigated using linear regression, with Pearson's correlation coefficient, r, reported. A P-value of 0.05 was considered statistically significant.

Results: TAI Pathology in the Corpus Callosum

Tables 1A-1B summarize the main demographic and histopathological findings observed in each examined CC across all cases included in this disclosure. No significant differences were found for age and post-mortem interval between fatal and nonfatal TBI, and healthy controls. No significant differences were found for APP-based DAI grade, DAI extent and severity between the fatal and nonfatal TBI cases as well.

FIGS. 3A-3C show simultaneous views from three representative TBI cases immunostains for microglia, astrocytes, myelin, and APP, histology stains for myelin and cell nuclei, and the deconvolved APP images along with the obtained APP densities. Levels of myelin density as assessed by both MBP immunohistochemistry and LFB stain did not show any marked loss across all considered regions (e.g., C, D, J, K, Q, R from FIGS. 3A-3C). By contrast, microglia activation and reactivity varied across all cases (e.g., A, H, O from FIGS. 3A-3C). Likewise, astroglial reactivity was variable as well (e.g., B, I, P from FIGS. 3A-3C). Both astroglial and microglial cells reactivities depend on various biological timing factors, most notably, time interval differences between the TBI exposure and autopsy (i.e., survival time), which varied greatly between the fatal and nonfatal TBI groups. Additionally, with the exception of Case 1, HE-based assessment of each CC did not reveal evidence of ischemic-necrotic lesions.

One hundred and thirty-two tissue blocks were analyzed, comprised of 4 APP-positive and 4 normal-appearing WM regions from each TAI case (totals of 32 and 32), 8 WM regions from the healthy control cases (total of 24), and 4 cortical GM regions from all cases (total of 44).

Figure 4A:
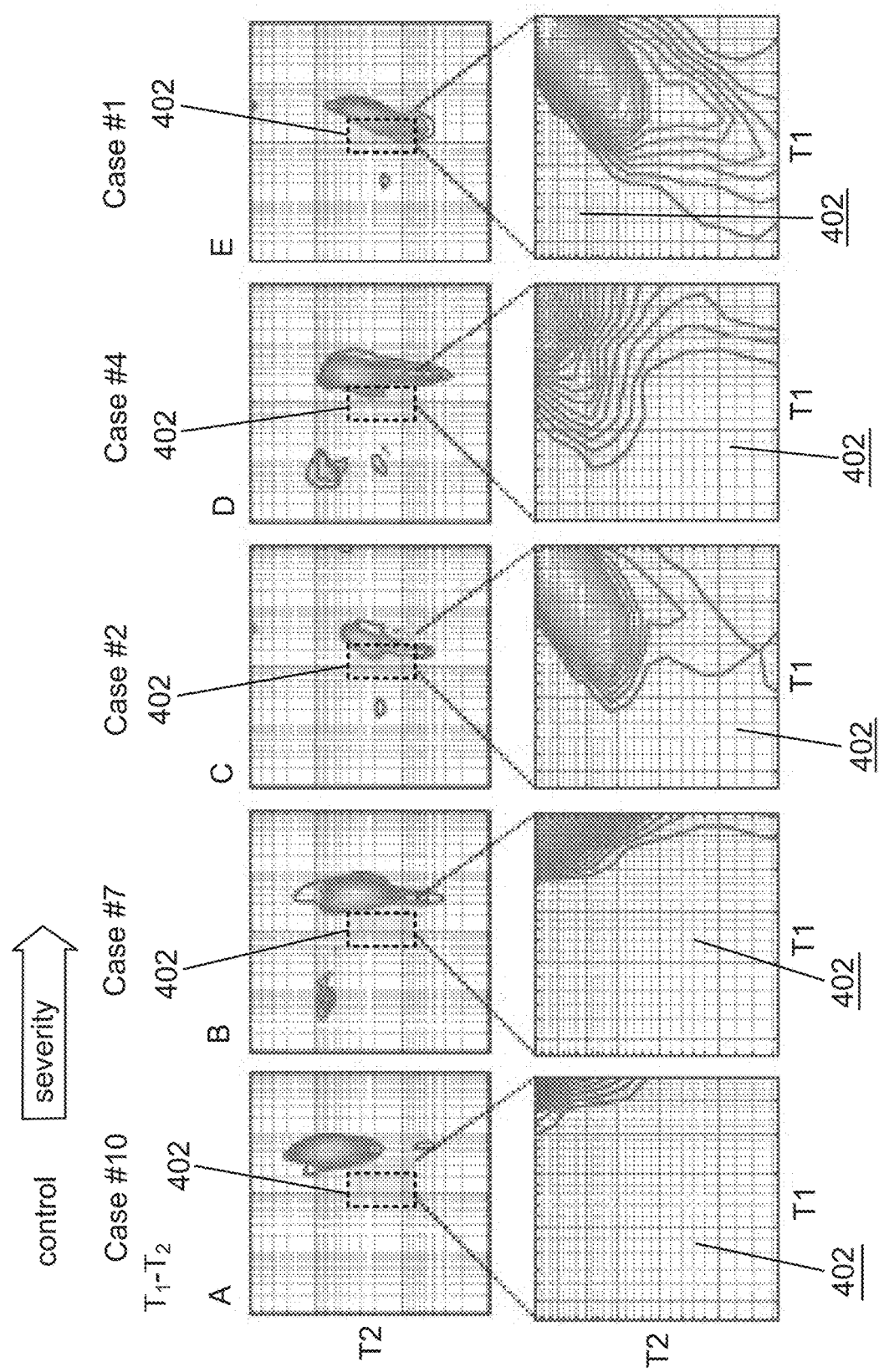
FIGS. 4A-4C show multidimensional spectra of TAI lesions in representative cases with increasing degree of severity (left to right). (A)-(E) T1-T2, (F)-(J) MD-T2, and (K)-(O) MD-T1. The most affected spectral regions of interest (sROI) were identified for each MR parameters couple (e.g., T1-T2), and are highlighted as rectangles defined with dashed lines. Below each distribution, a magnification of the corresponding sROI is shown. The progressive shift towards shorter T1, shorter T2, and slower diffusivity as the severity of the injury increases is evident.
Figure 4B:
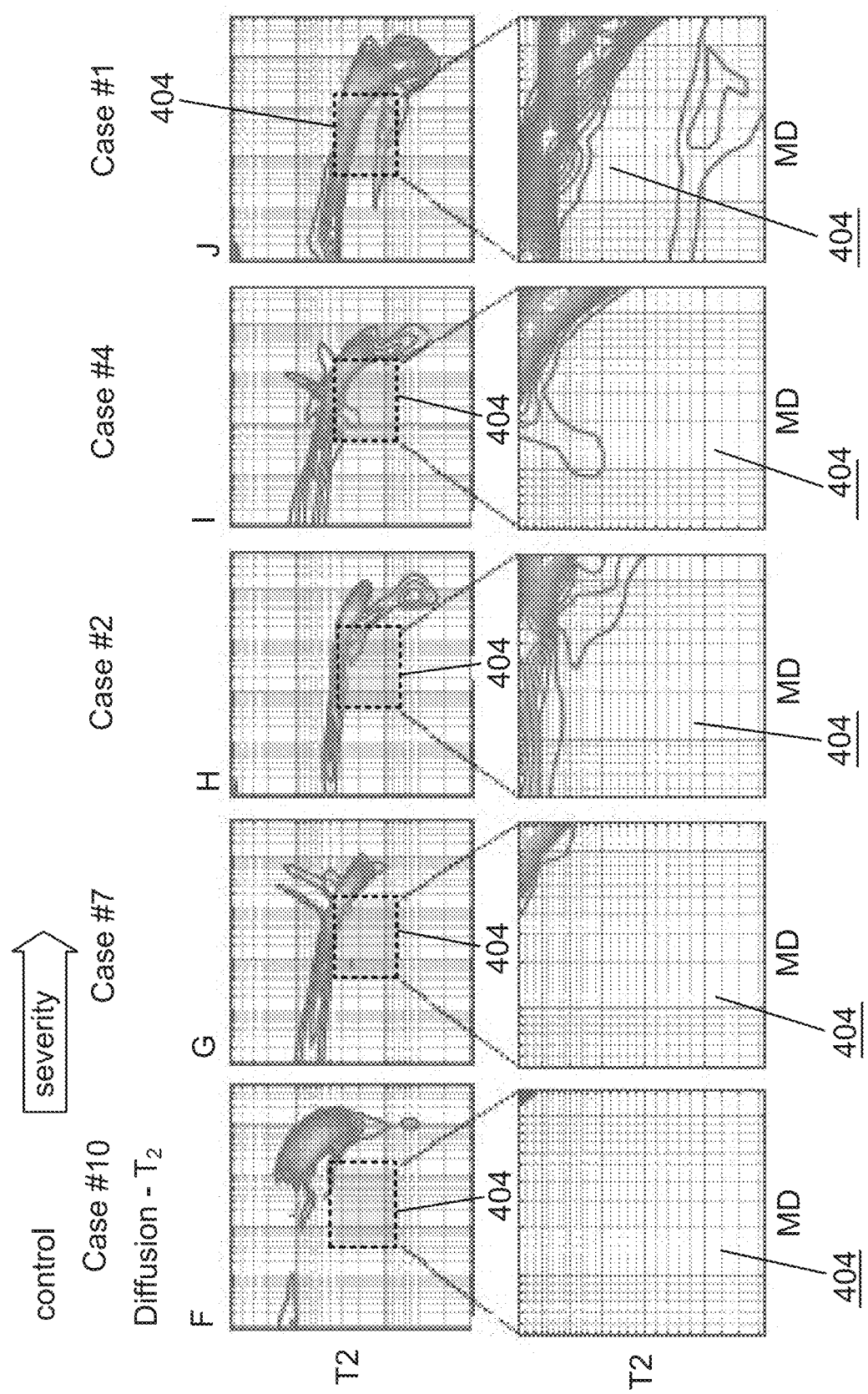
Figure 4C:
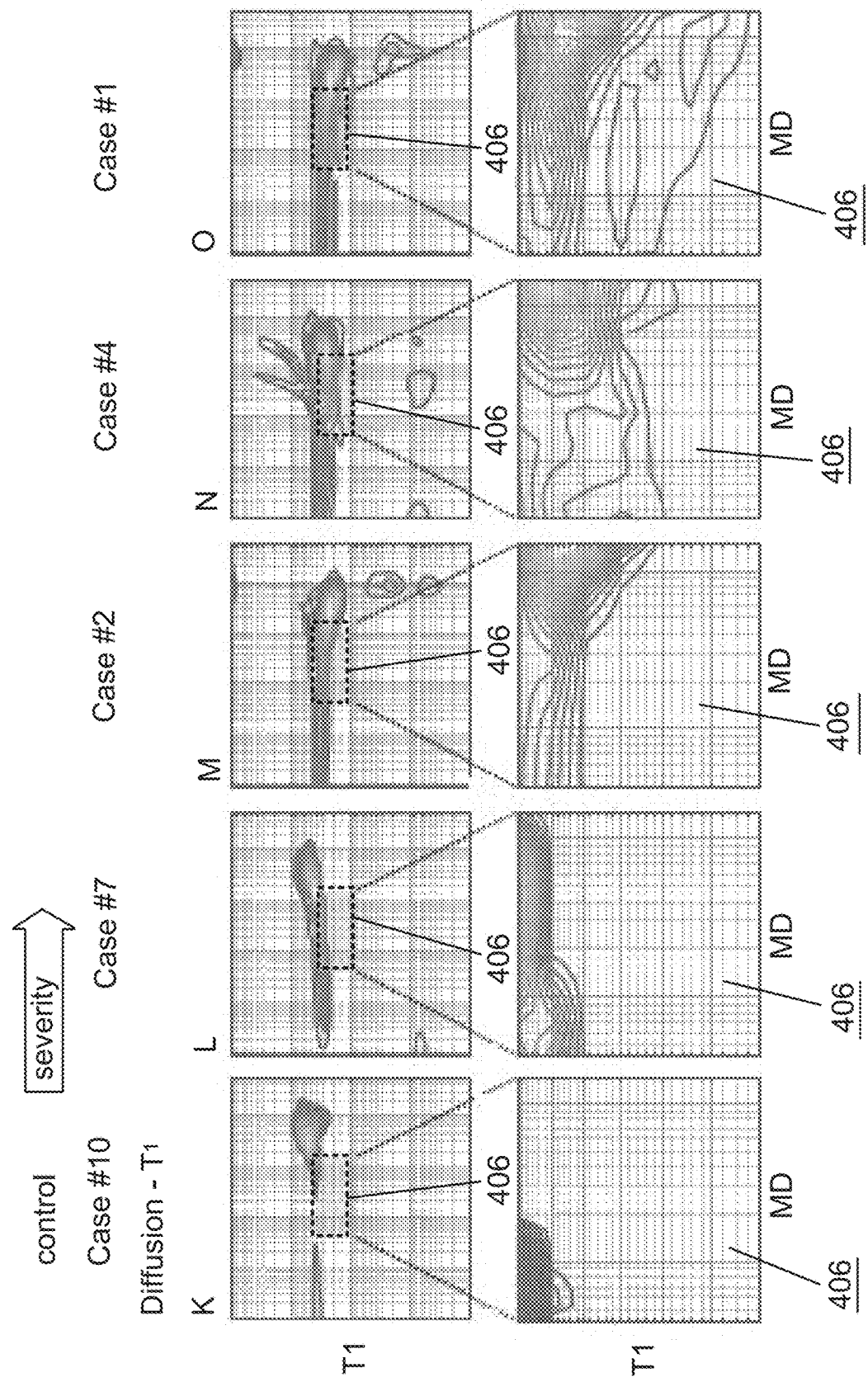

Transverse and Longitudinal Relaxation Times Shorten as a Function of TAI Severity There is a consistent and gradual change in the way in which T1, T2, and MD are distributed as the severity of the TAI increase. FIGS. 4A-4C show five cases with increased injury severity and their respective T1-T2 (A-E), MD-T2 (F-J), and MD-T1 (K-O) distributions from control and TAI regions. The shift in the distributions can be illustrated by examining the most affected T1, T2, and MD ranges, which are highlighted as ranges 402, 404, 406, respectively. A magnification of each of these ranges in the spectra, or spectral region of interest (sROI), is shown below each distribution. Qualitatively, the sROIs show a gradual shortening of T1 and T2 as the severity of the injury is increased (FIGS. 4A-4C, left to right). A shift towards lower MD values is also noticeable, although not as consistent as changes in the relaxation distributions.

To allow a quantitative cases-by-case analysis, mean voxel- and sROI-averaged MRI parameters from the TAI tissue blocks were calculated. Compared with healthy control WM, 6 of 8 tissue blocks evaluated from TAI patients had significantly shorter voxel-averaged T1 values, ⅝ had significantly shorter sROI-averaged T1 values, ⅝ had significantly shorter voxel-averaged T2 values, ⅝ had significantly shorter sROI-averaged T2 values, ⅜ had significantly lower voxel-averaged MD values, ⅝ had significantly lower sROI-averaged MD values, and ⅜ had significantly lower voxel-averaged FA values. In all cases the % area APP was significantly higher in TAI regions, compared with control WM. These values are summarized in Table 2 (see FIGS. 18A and 18B).

Multidimensional and Voxel-Averaged MR Images of TAI

Based on the control and TAI cases a T1-T2-MD range, (T1=[91.03, 339.32] ms, T2=[6.70, 34.85] ms, and MD=[0.004, 0.146]$\mu m^2$/ms) was identified which most can be used to assess injury. Integration according to the spectral signature within this range was performed, resulting in MD-T1, MD-T2, and T1-T2 TAI SC images.

Figure 5A:
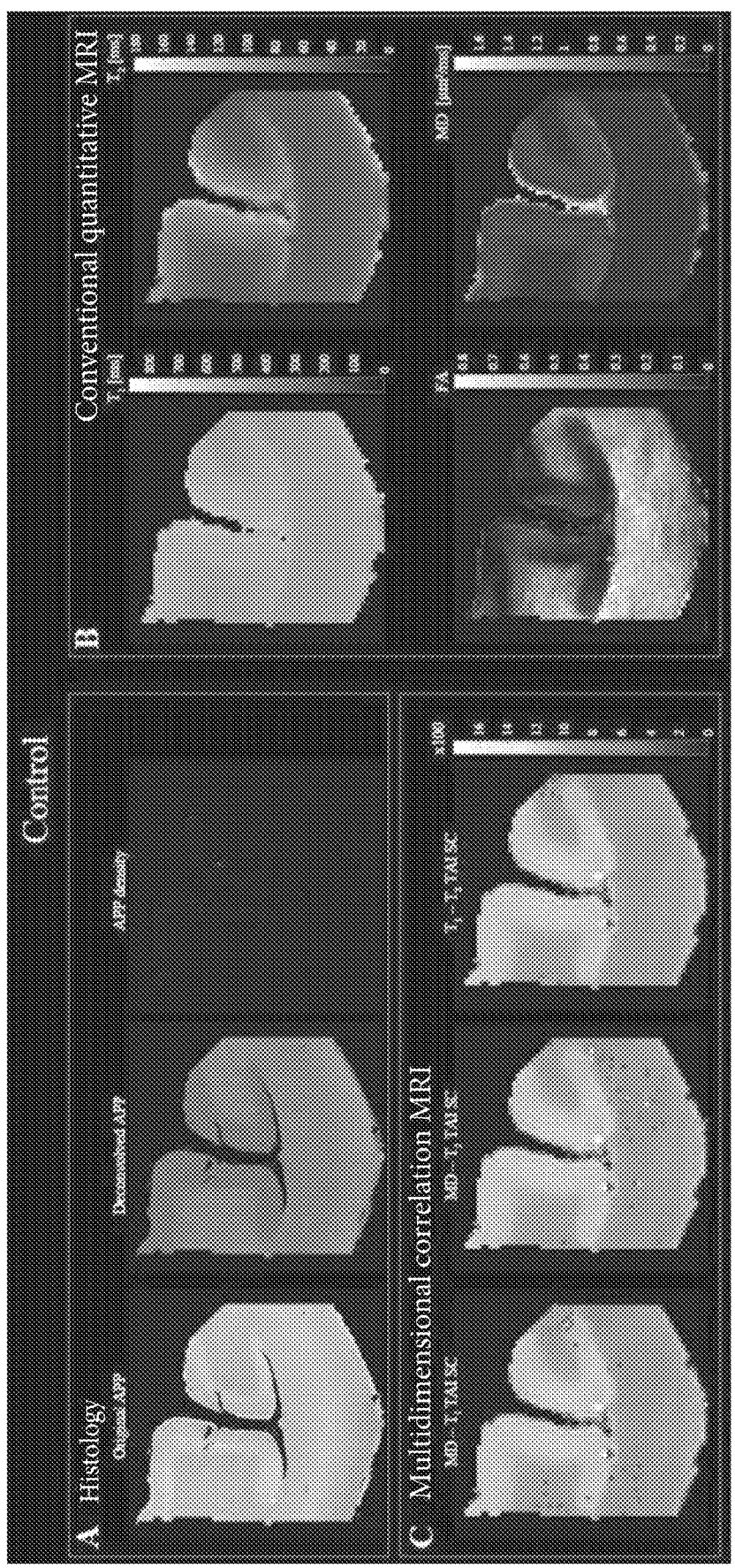
FIGS. 5A-5C show multidimensional and voxel-averaged MR images of TAI. Control brain (Case 10) (A) APP histological images co-registered to MRIs. Deconvolved histological image: red=APP stain. Negligible APP density was detected. (B) Conventional MRI maps of T1, T2, FA and MD do not show visible abnormalities. (C) Multidimensional TAI SC maps overlaid onto proton density images show absent of significant injury. Nonfatal TBI brain (Case 6) (D) APP histological images co-registered to MRIs show visible TAI in the CC. (E) Conventional MRI maps of T1, T2, FA and MD do not show visible abnormalities in the CC. (F) Multidimensional TAI SC maps overlaid onto proton density images show significant injury in WM (in particular, the T1-T2 TAI SC). Fatal TBI brain (Case 2) (G) APP histological images co-registered to MRIs show TAI in regions of WM/GM interface. (H) Conventional MRI maps of T1, T2, FA and MD do not show visible abnormalities in WM/GM interface. (I) Multidimensional TAI SC maps overlaid onto proton density images show significant injury along the WM/GM interface.
Figure 5B:
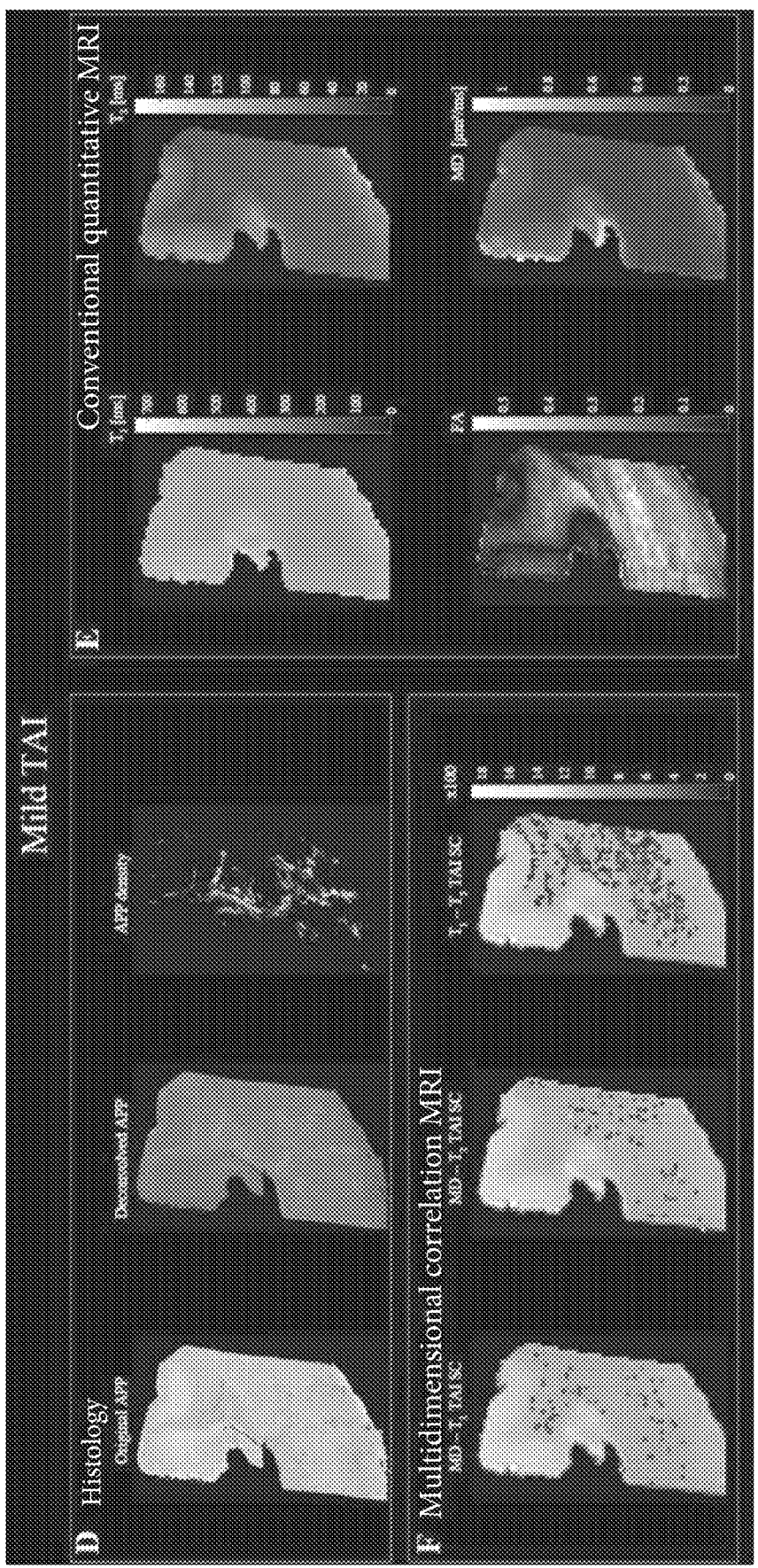
Figure 5C:
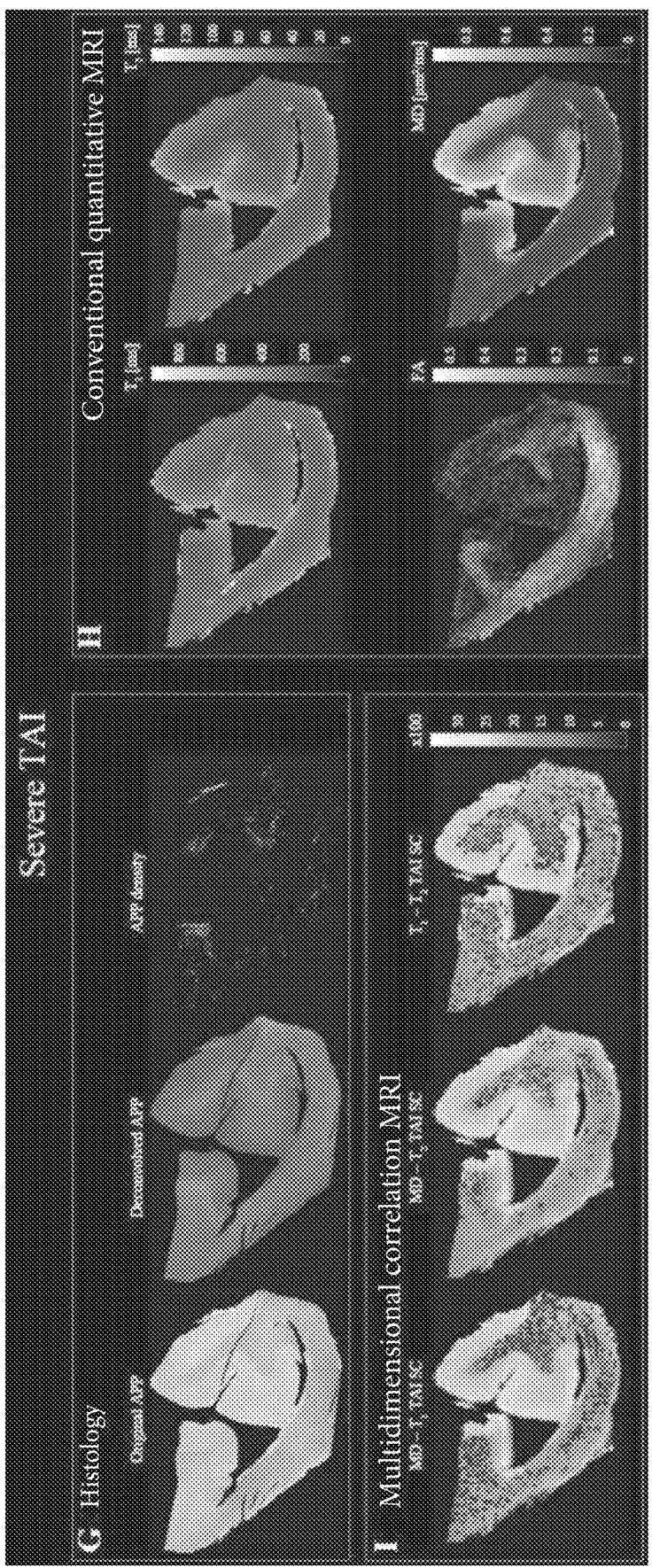
Figure 6A:
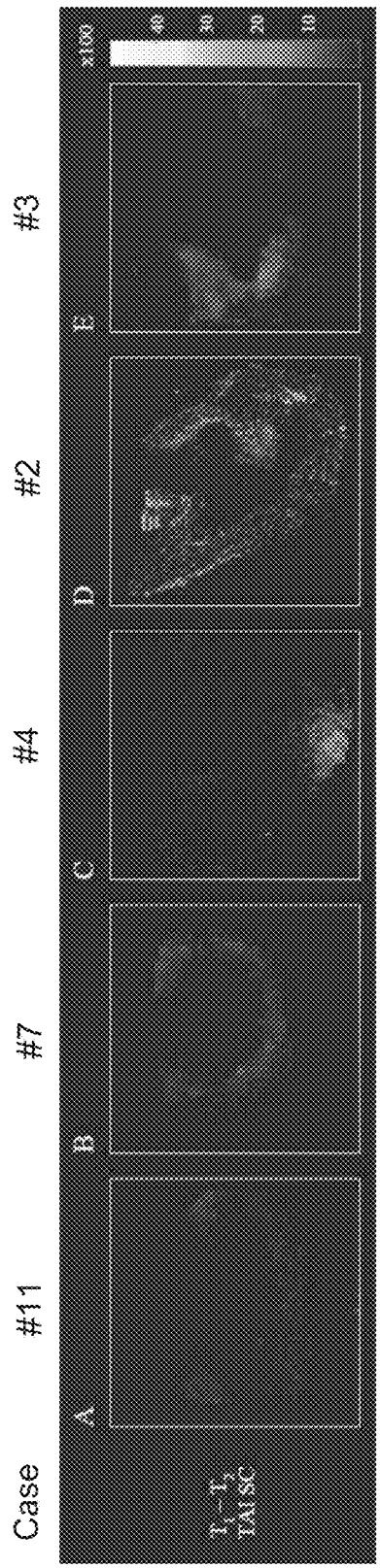
FIGS. 6A-6C include additional multidimensional TAI SC images without proton density images.
Figure 6B:
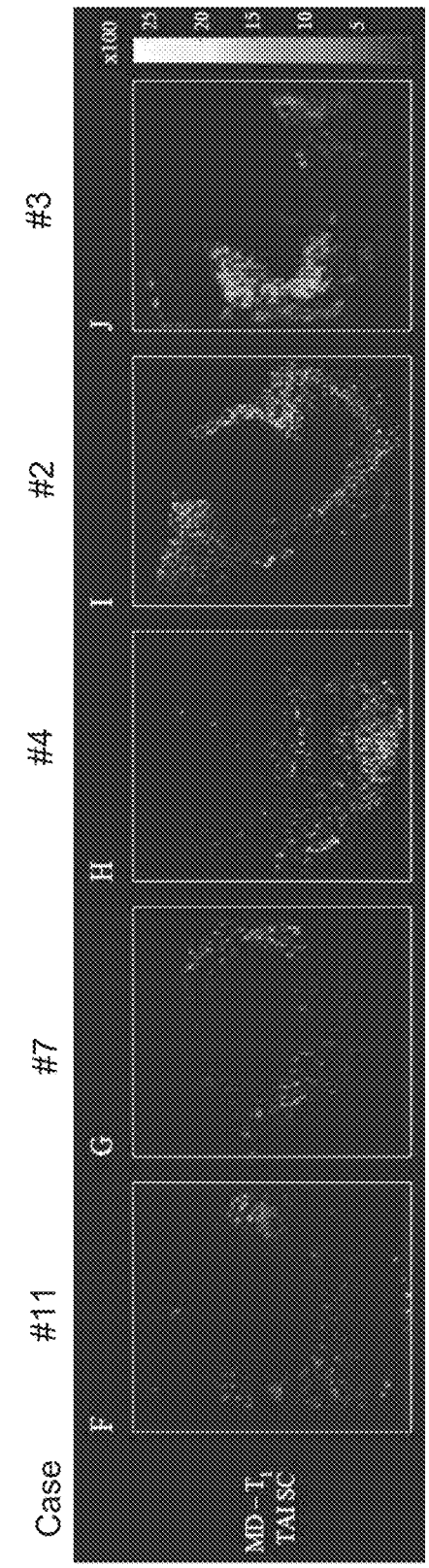
Figure 6C:
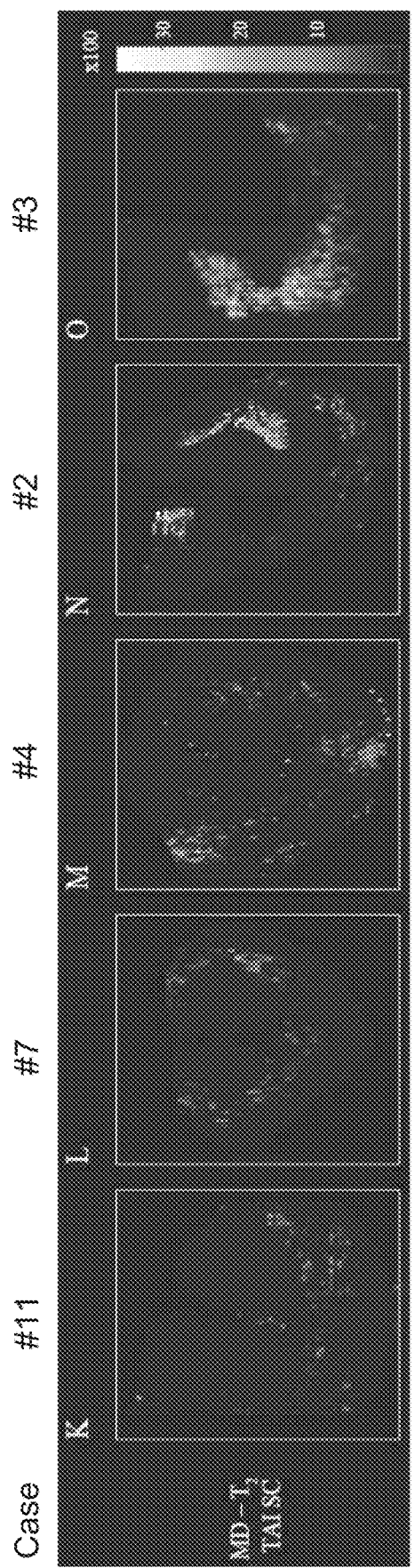
Figure 7A:
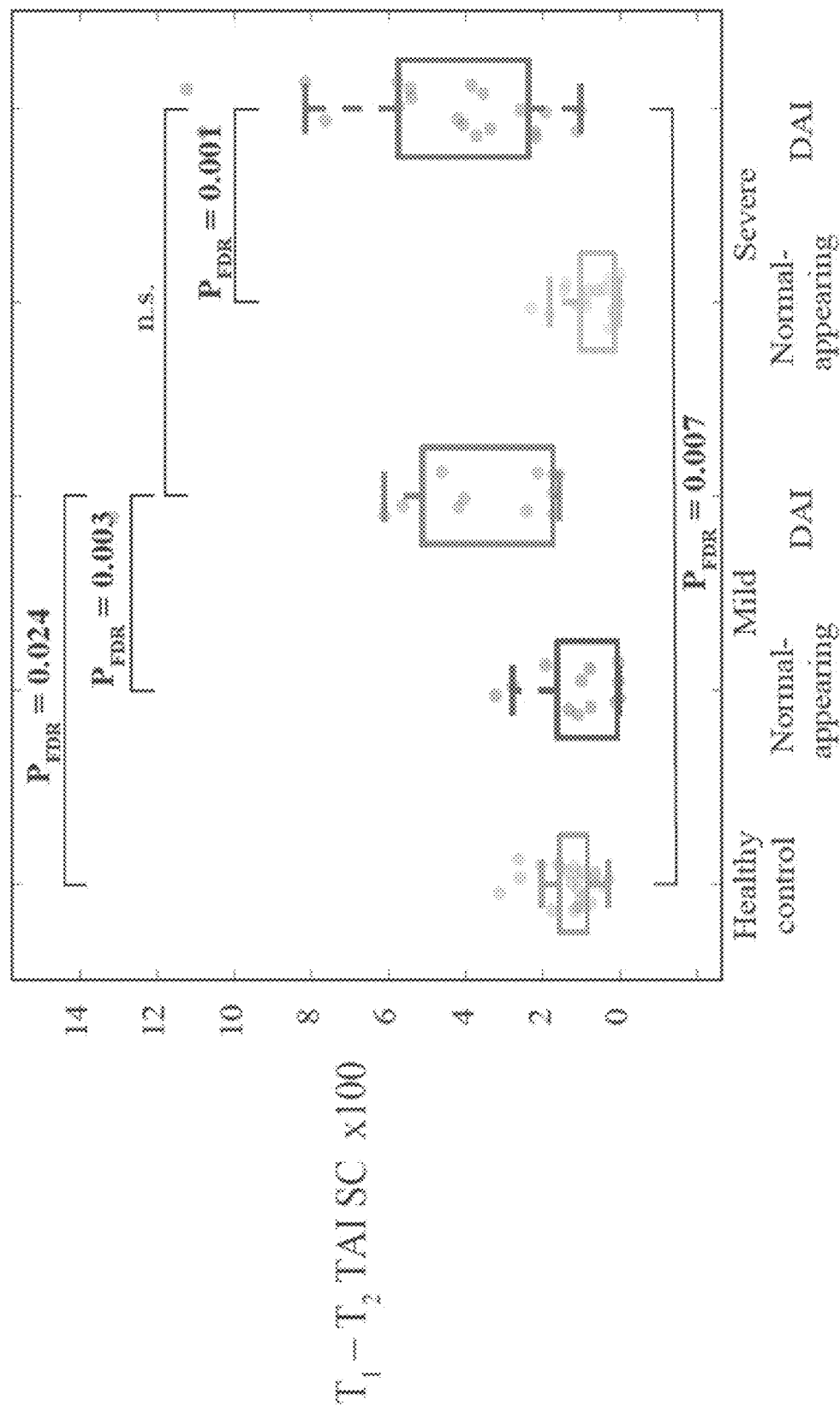
FIGS. 7A-7F contain between-group comparisons of voxel-averaged and multidimensional biomarkers and histopathological measures. Box plots showing between-group differences among healthy control CC, normal-appearing mTAI CC, mTAI lesions, normal-appearing sTAI CC, and sTAI lesions. (A) T1-T2 TAI SC; (B) MD-T2 TAI SC; (C) APP density; (D) voxel-averaged MD; (E) voxel-averaged T1; and (F) voxel-averaged T2.
Figure 7B:
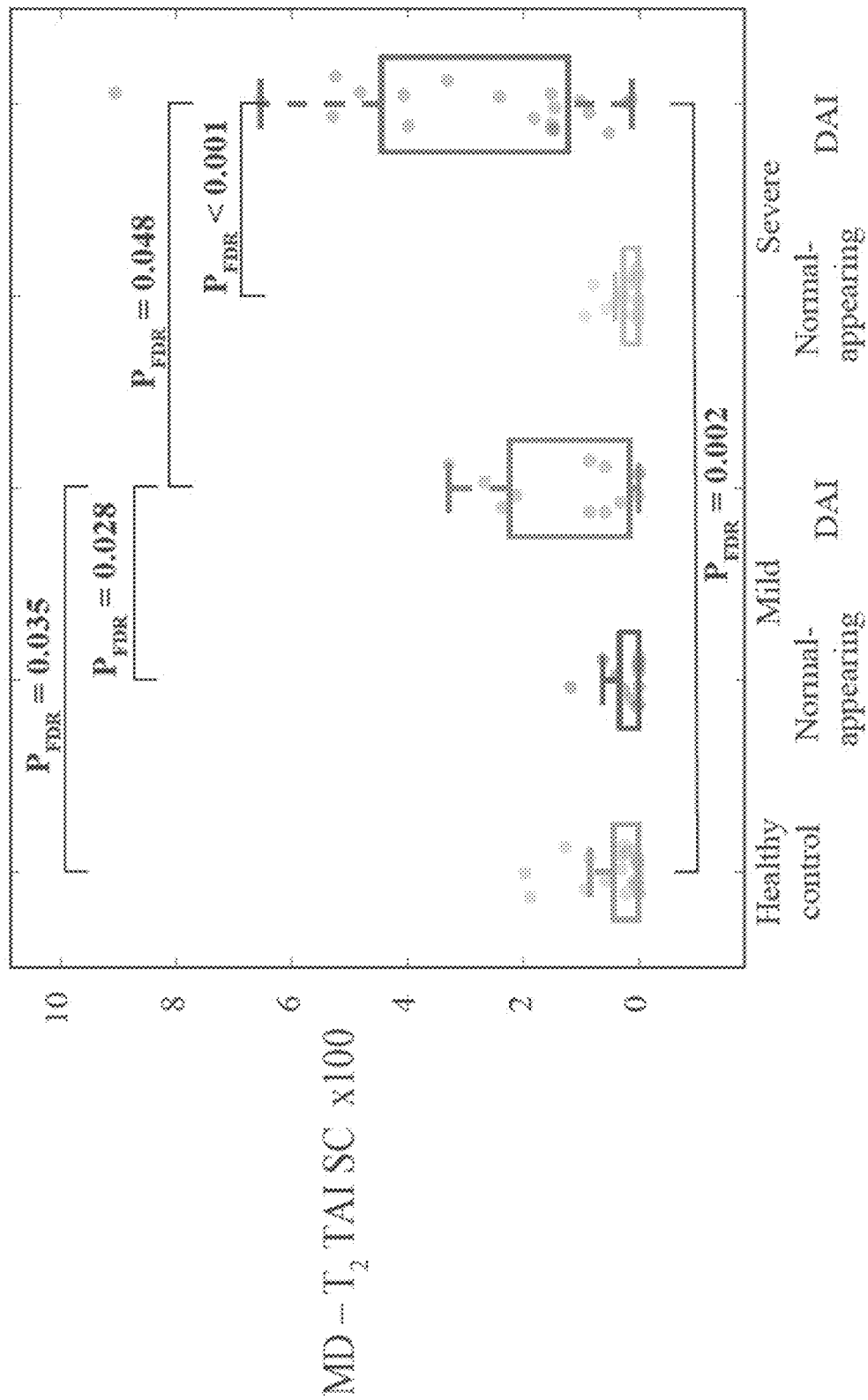
Figure 7C:
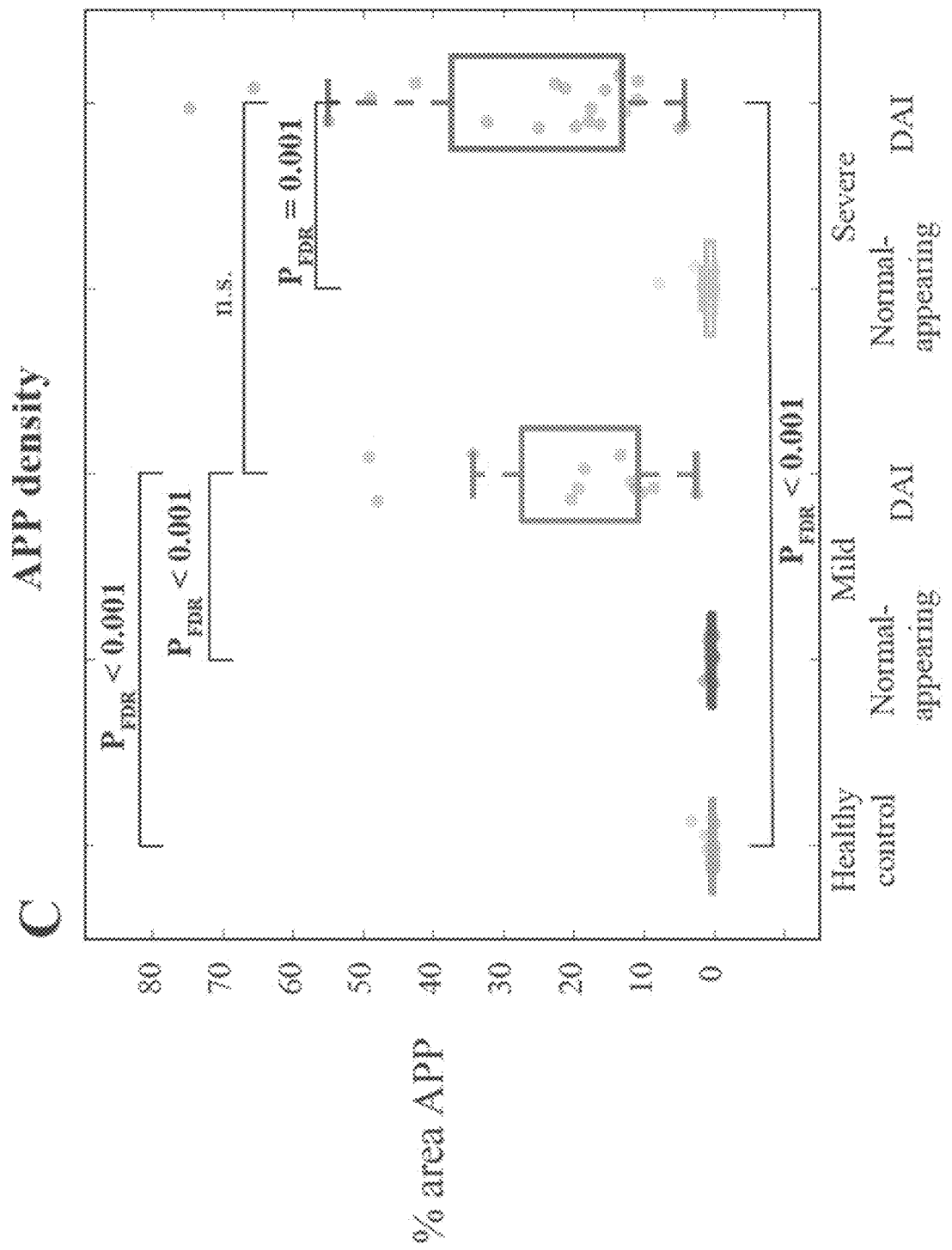
Figure 7D:
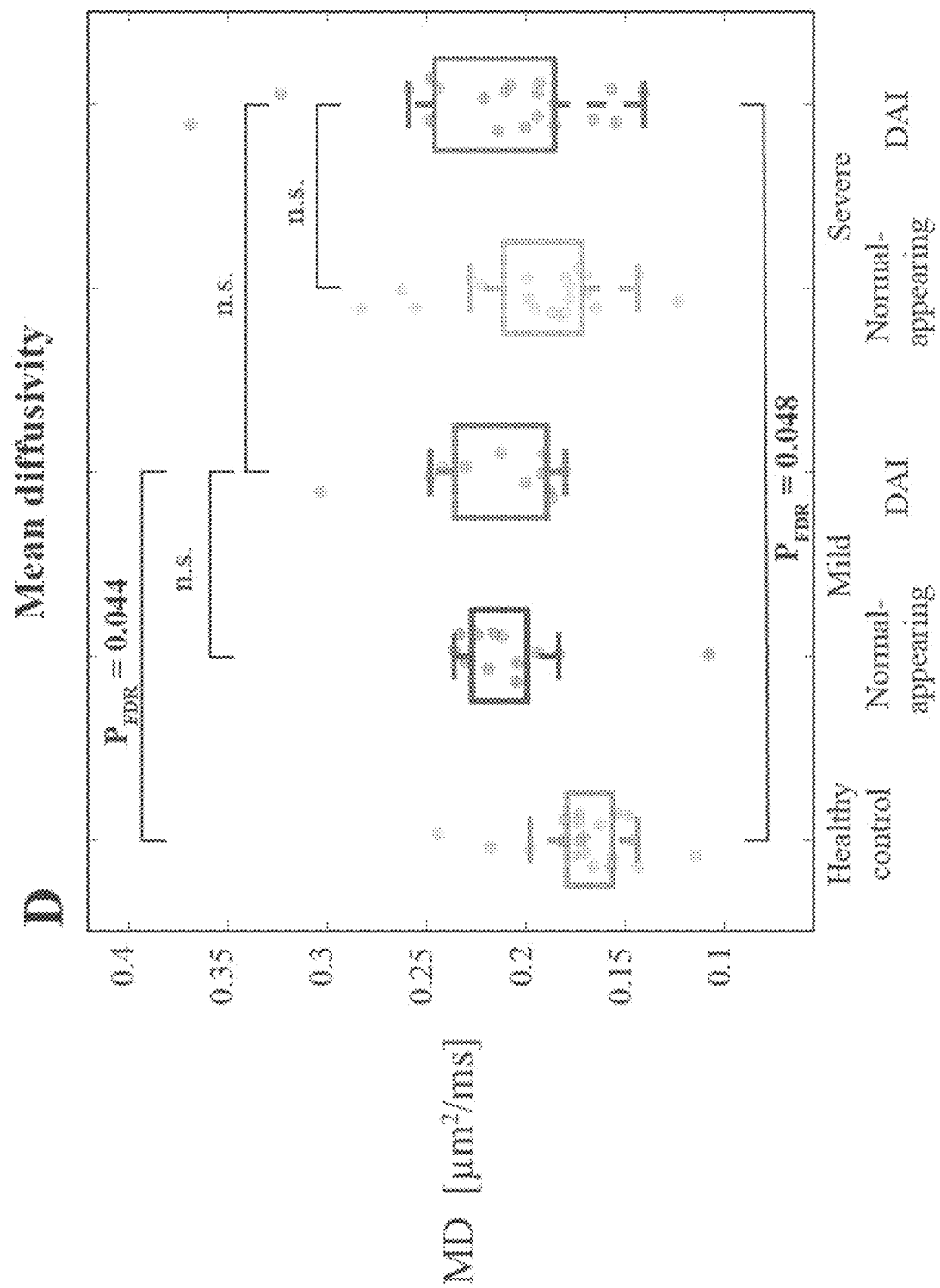
Figure 7E:
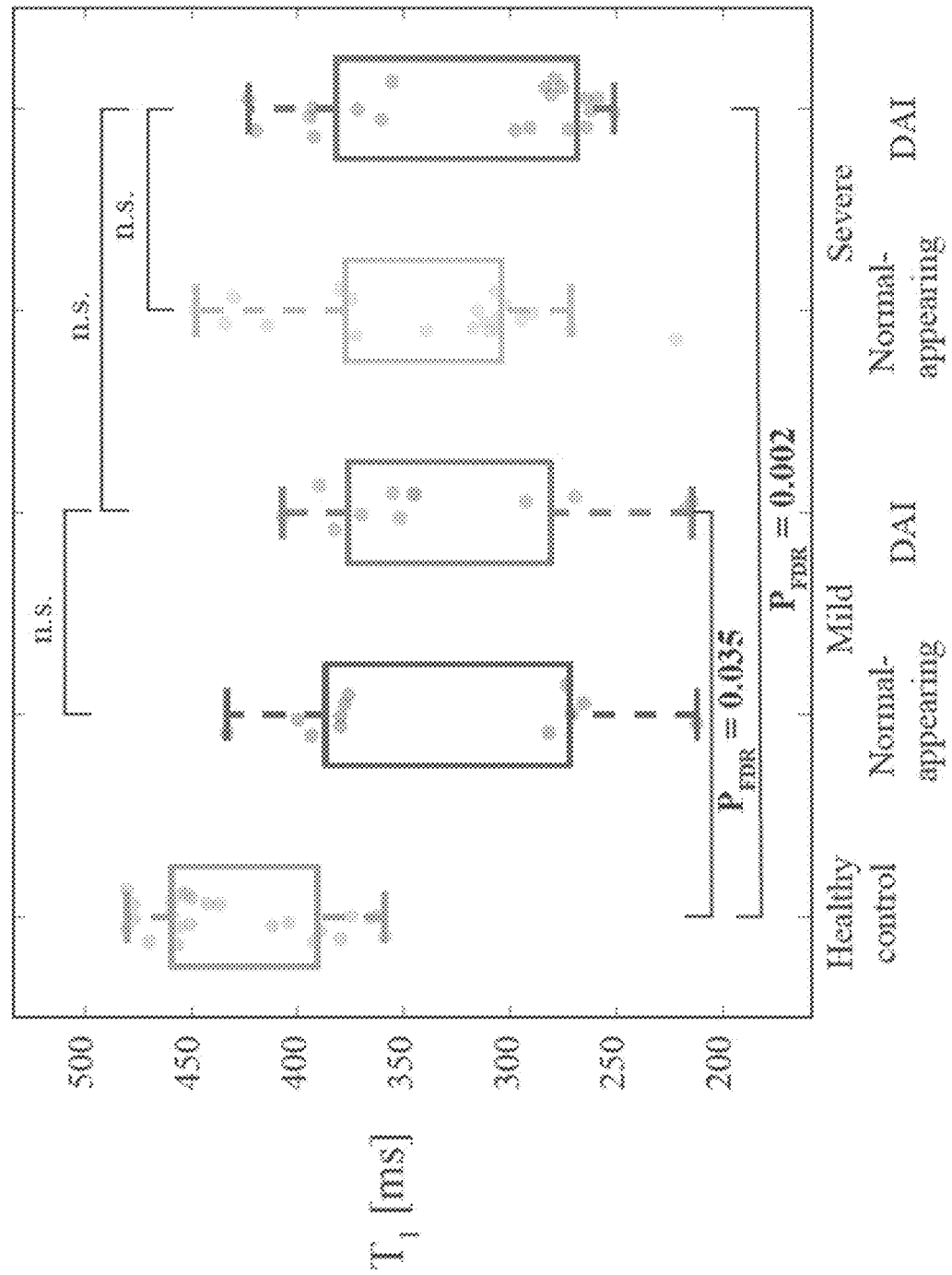
Figure 7F:
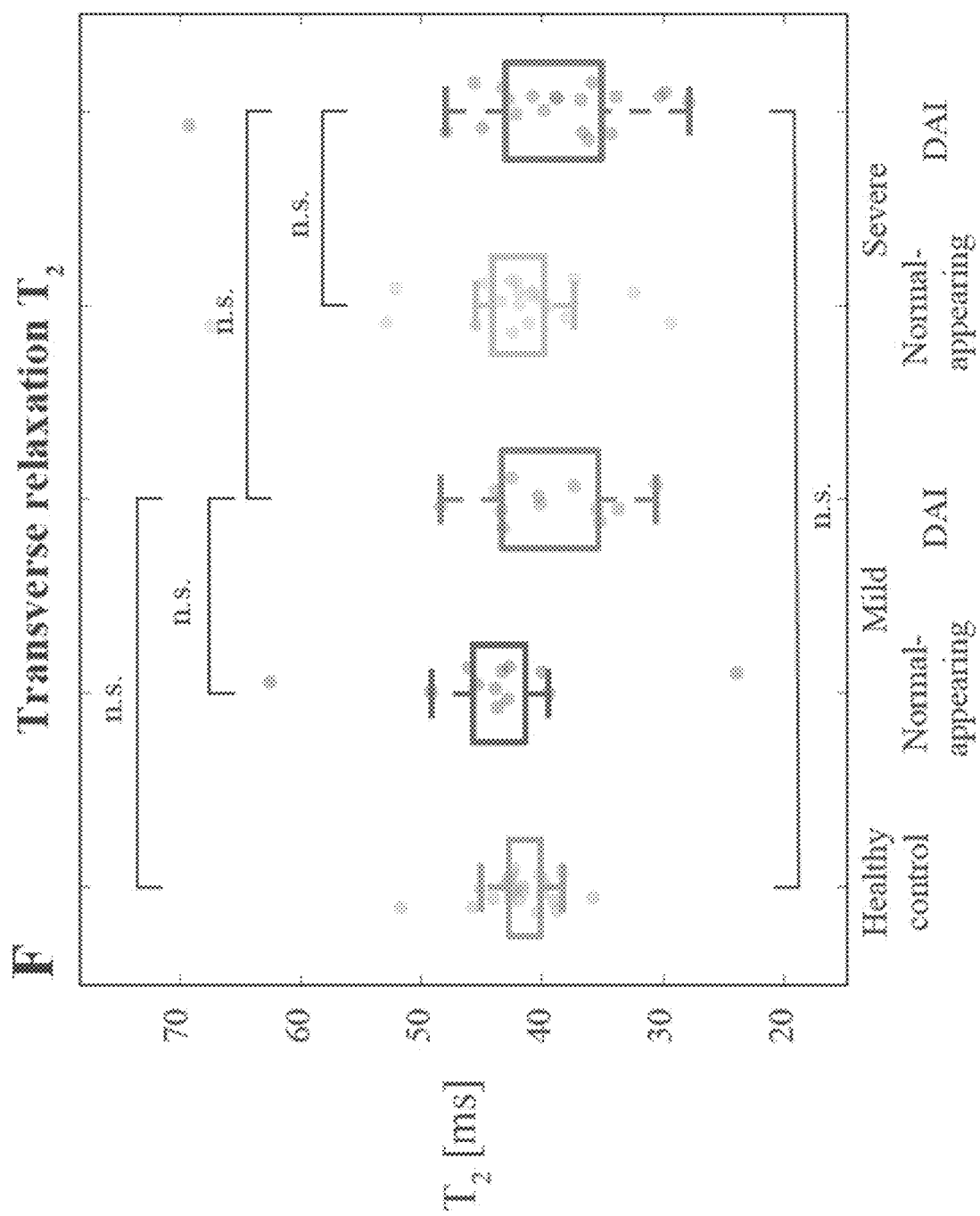
Figure 8A:
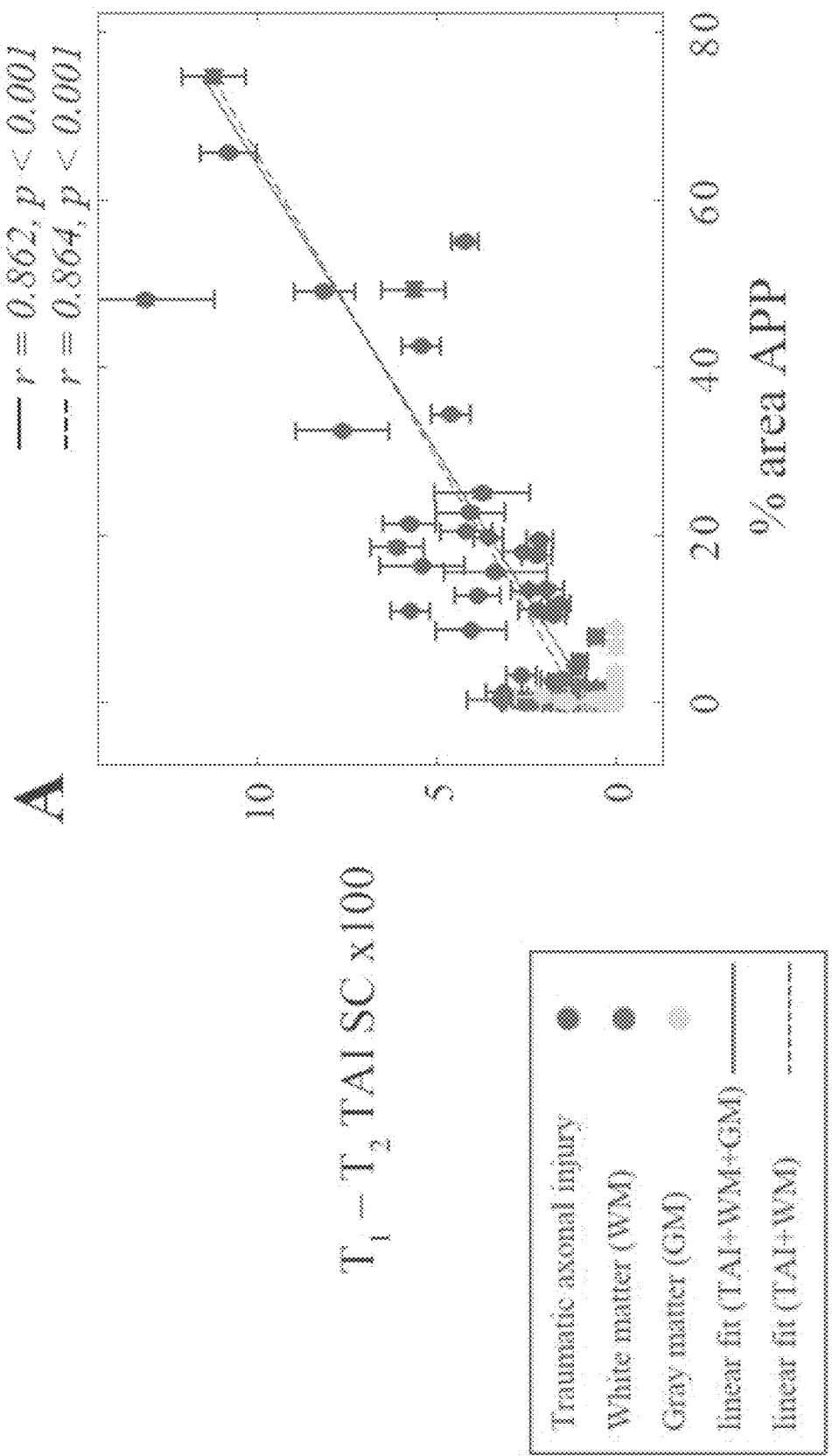
FIGS. 8A-8G show APP density (% area) from 132 tissue blocks, comprised of 4 APP-positive regions from each TAI case (total of 32, blue dots), 4 to 6 normal-appearing WM regions from all cases (total of 56, red dots), and 4 cortical GM regions from all cases (total of 44, yellow dots), and the corresponding MR parameter correlations. Individual data points represent the mean ROI value from each post-mortem tissue sample. Scatterplots of the mean (with standard error bars) % area APP and (A) T1-T2, (B) MD-T1, and (C) MD-T2 TAI SCs show positive and significant correlation with APP density. Both T1-T2 and MD-T2 TAI SCs demonstrated specificity exclusively towards TAI (all GM and normal-appearing WM had negligible intensities). The conventional MRI metrics (D)-(G) did not result in strong and significant correlations with % area APP.
Figure 8B:
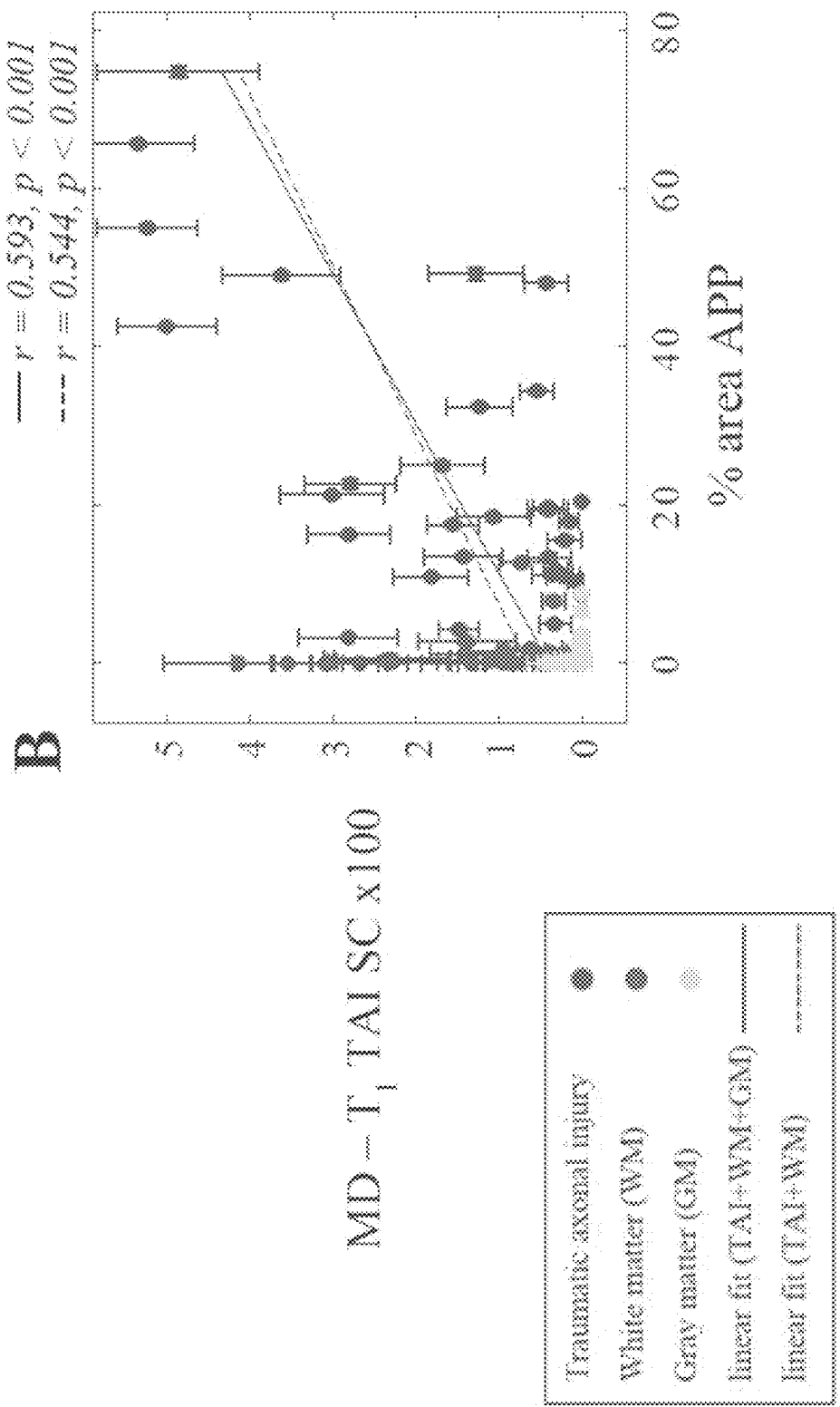
Figure 8C:
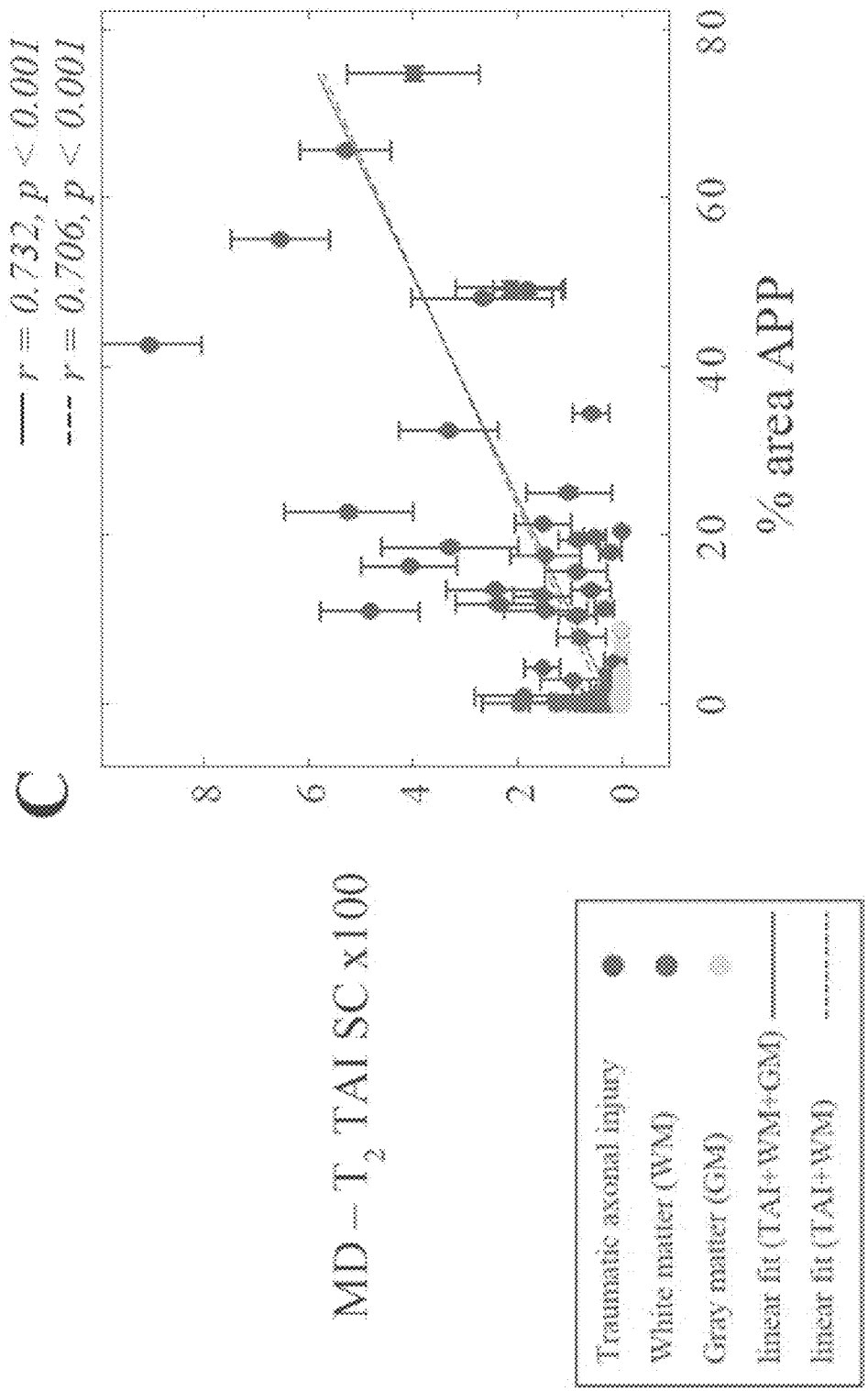
Figure 8D:
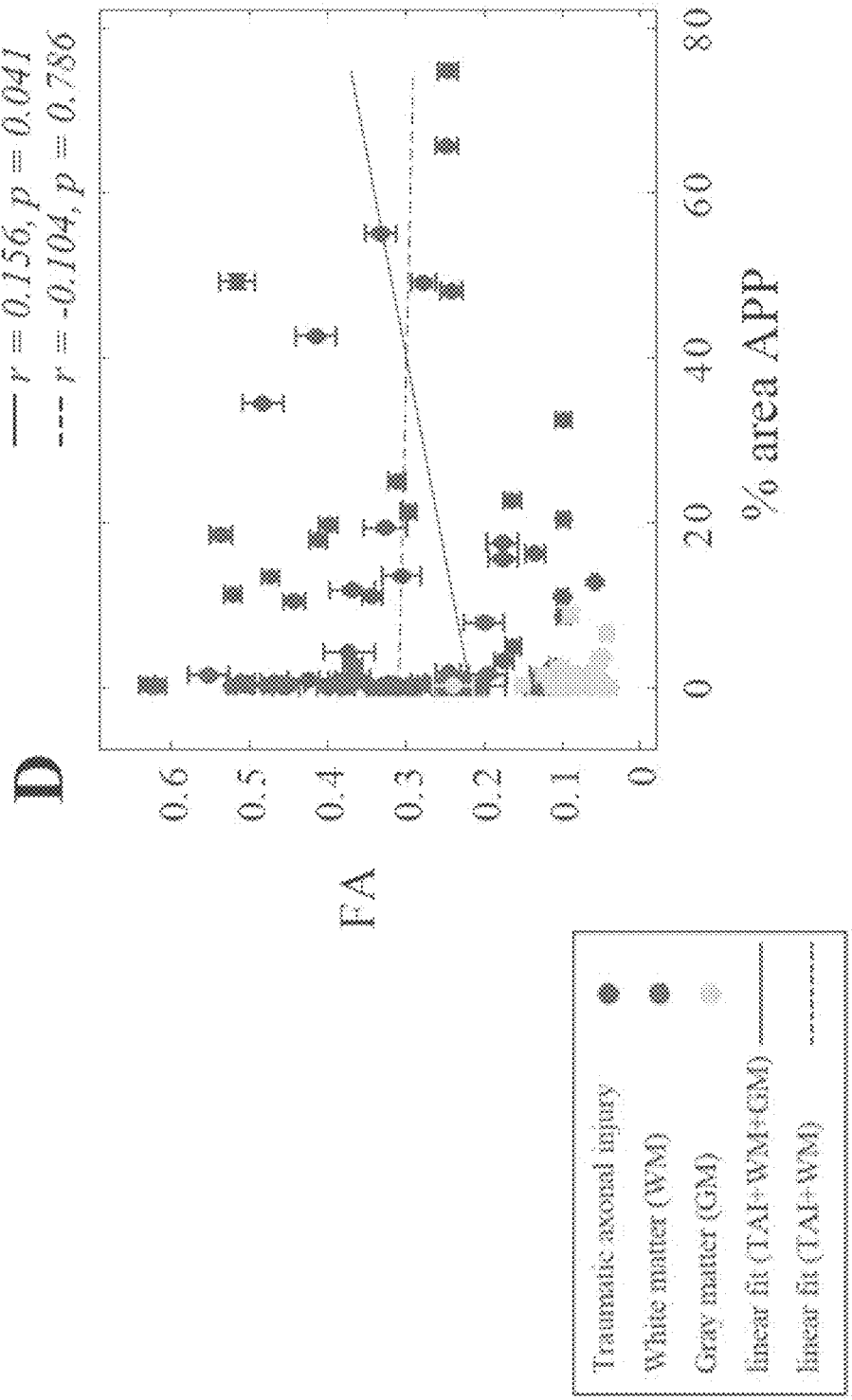
Figure 8E:
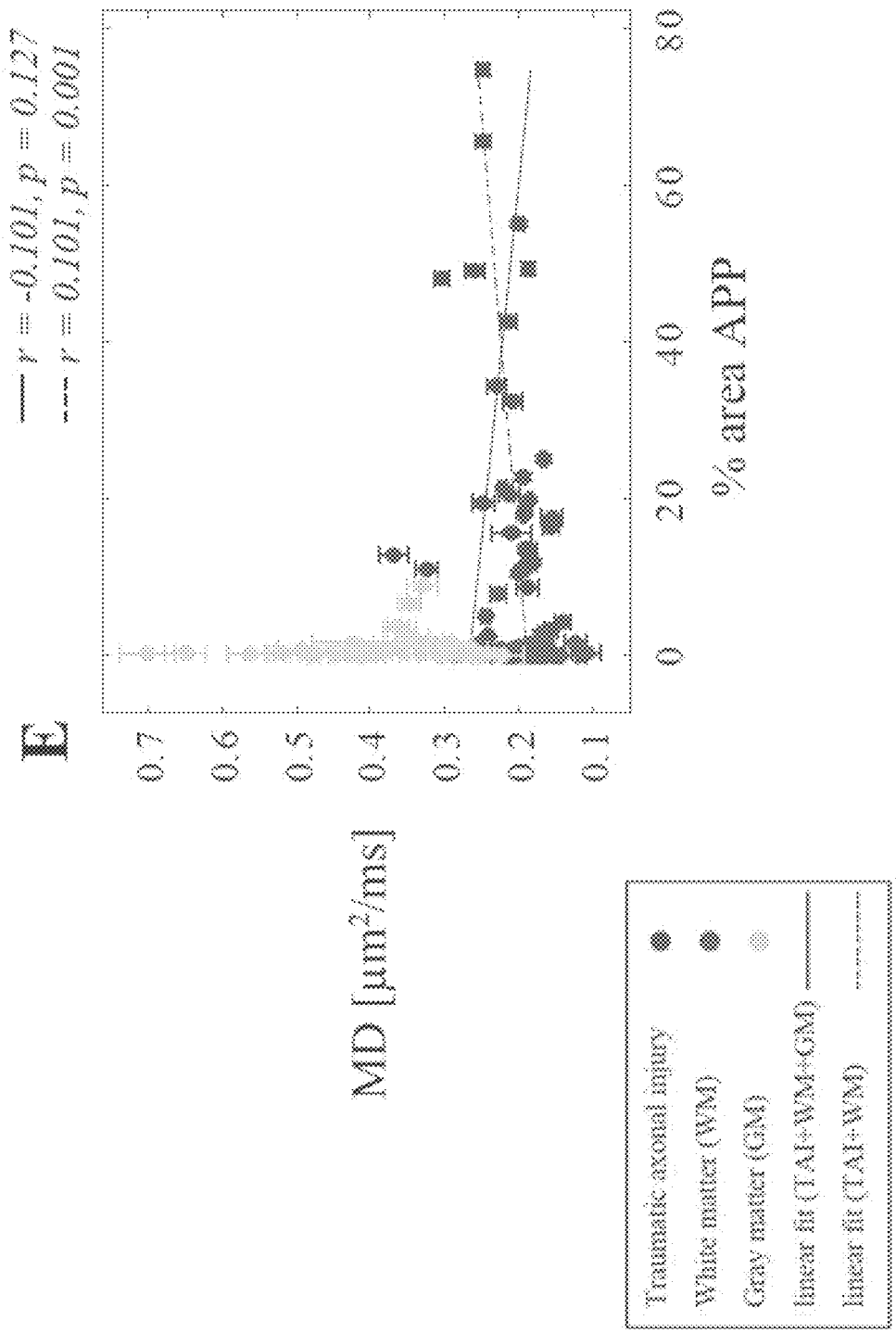
Figure 8F:
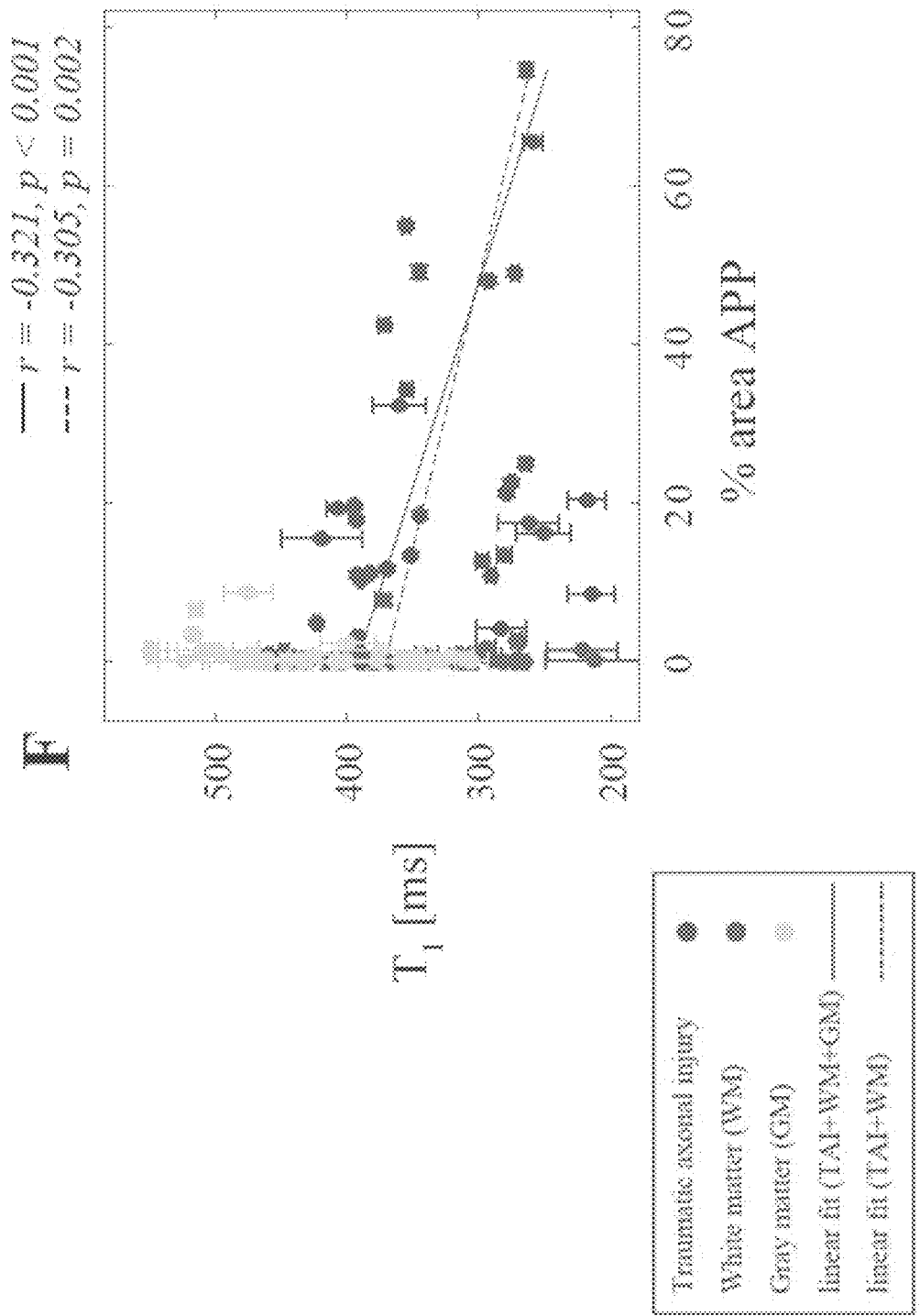
Figure 8G:
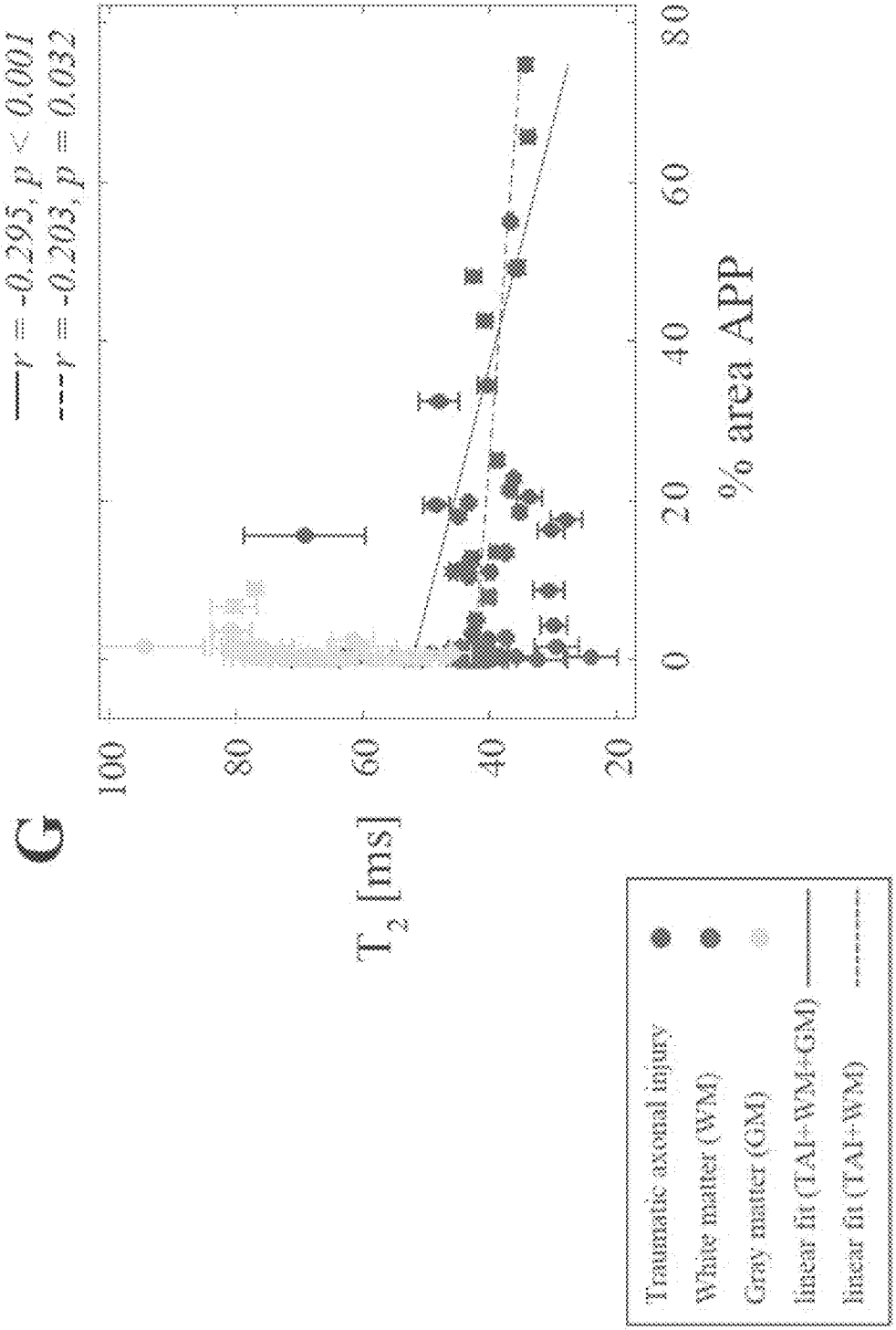

FIGS. 5A-5C shows conventional and multidimensional MR and histological images of three representative cases: healthy control, nonfatal and fatal TBI (cases 10, 6, and 2). Histological images of the control case show negative APP staining (A from FIG. 5A), compared with positive APP staining in the injured samples (D and G from FIGS. 5B and 5C). Conventional, voxel-averaged relaxation and diffusion images of the control, nonfatal and fatal cases, are shown in B, E, and H from FIGS. 5A-5C, respectively. Lastly, the multidimensional TAI SC images of the control, nonfatal and fatal cases, are shown in C, F, and I from FIGS. 5A-5C, respectively. Note that to facilitate visualization, the TAI SC images were overlaid on grayscale proton density images. More multidimensional TAI SC images are shown in FIGS. 6A-6C but without grayscale proton density images.

Histopathological, Multidimensional and Conventional MRI Findings

The 132 tissue blocks were grouped into healthy controls, normal-appearing WM in TBI patients, and DAI regions in TBI patients and the TBI patients were portioned into mild and severe DAI (s- and mDAI) according to the APP staining-based severity in Tables 1A-1B (see FIGS. 17A-17D) to assess whether the examined MRI metrics are able to specifically identify TAI with different degrees of severity (cases 1-4 and 6 were grouped as sDAI and cases 5, 7, and 8 as mDAI). Compared to healthy controls, mTAI brains showed increased T1-T2 TAI SC (FDR-corrected P-value, PFDR=0.024), increased MD-T2 TAI SC (PFDR=0.035), increased MD (PFDR=0.044), decreased T1 (PFDR=0.035), and increased % area APP (PFDR<0.001). This is shown in Table 3 (FIG. 18C) and FIGS. 7A-7F.

Compared to healthy controls, sTAI brains showed increased T1-T2 TAI SC (PFDR=0.007), increased MD-T2 TAI SC (PFDR=0.002), increased MD (PFDR=0.048), decreased T1 (PFDR=0.002), and increased % area APP (PFDR<0.00).

Compared to normal-appearing WM tissue blocks in mTBI brains, mTAI regions showed increased T1-T2 TAI SC (PFDR=0.003), increased MD-T2 TAI SC (PFDR=0.028), and increased % area APP (PFDR<0.00).

Compared to normal-appearing WM tissue blocks in sTBI brains, sTAI regions showed increased T1-T2 TAI SC (PFDR=0.001), increased MD-T1 TAI SC (PFDR=0.042), increased MD-T2 TAI SC (PFDR<0.00), and increased % area APP (PFDR=0.001).

The MD-T2 TAI SC parameter was the only one that was able to distinguish between injury sites in mTBI and sTBI brains (PFDR=0.048), shown in Table 4 (FIGS. 18D-18E).

None of the other MRI metrics showed significant between-group differences as shown in Tables 3-4 (FIGS. 18C-18E) and FIGS. 7A-7F).

Correlation Between MRI Measures and APP Density

To determine whether MRI could potentially detect DAI in TBI brains, radiological-pathological correlation analyses was performed with histological APP density and the investigated MRI parameters. FIGS. 8A-8G summarize the association between the MR metrics—conventional voxel-averaged and multidimensional SCs—and the pathological findings in normal WM, cortical GM, and TAI tissue blocks.

To assess the specificity of the MRI parameters, all tissue types were grouped together and correlated with the APP density (solid lines in FIGS. 8A-8G). As shown in the multidimensional images, APP density had the strongest and most significant correlation with T1-T2 TAI SC (r=0.862, P<0.001) and the MD-T2 TAI SC (r=0.732, P<0.001), and had a moderate correlation with the MD-T1 TAI SC (r=0.593, P<0.001). These results indicated that higher intensity of the multidimensional TAI SCs is associated with increased DAI, regardless of the tissue type.

From the conventional voxel-averaged images, APP density had a weak yet significant correlations with T1 (r=−0.321, P<0.001) and with T2 (r=−0.295, P<0.001). The DTI parameters did not have a significant correlation with APP density, as shown in FIGS. 8A-8G. These results indicated that shorter T1 and T2 are associated with increased DAI.

To assess the capability of the MRI parameters to differentiate between normal and injured WM with respect to APP density, normal white matter and TAI tissue blocks were grouped together (dashed lines in FIGS. 8A-8G). From the multidimensional images, correlations with APP density have barely changed by excluding the cortical GM tissue blocks. Similarly, grouping WM only tissue blocks did not significantly affect the correlation of APP density and the conventional voxel-averaged parameters with the exception of T2, which was slightly reduced (r=−0.203, P=0.032).

Example Summary

By combining a wide array of conventional voxel-averaged and multidimensional post-mortem ex vivo MRI and histopathological markers, the pathological elements of T1-T2-MD multidimensional MRI in TAI corpora callosal have been identified. Using multidimensional MRI, the ability to selectively image a specific range of relaxation times allows capture of the strong association of T1 and T2 shortening with the severity of TAI. According to one view, proteins, which have very short T2 values, interact with free and partially bound water, reducing both T1 and T2. Axonal injury causes microtubule disruption that leads to accumulation of APP and other proteins, and to the formation of axonal varicosities. While direct detection of proteins may not be visible with MRI, these protein aggregates may act as relaxation enhancers for the surrounding water, which is captured by shortened T1-T2 (FIGS. 6A-6C).

The T1-T2 MRI sequence used herein permits migration towards clinical applications. T1-T2-weighted acquisition is clinically feasible especially considering the relatively small number of data points that are required.

As shown herein, the CC was consistently affected by DAI following trauma. Apart from Case 1, none of the CCs evaluated showed macroscopic damage, cytotoxic edema, or large (>1 mm) lesions. No myelin loss was observed in any of the examined cases, and glia cells reactivity varied greatly between cases, most likely due to variability in the survival time. These histopathological findings suggest that the damage from TAI in these was microscopically limited, and in most cases did not result in macroscopic loss.

Robust quantitative radiological-pathological correlation allows determination of regions with substantial DAI and regions that unaffected by trauma. While voxel-averaged MRI approaches, primarily voxel-averaged MD and T1, are able to detect differences between healthy controls and TBI CC, they are completely insensitive to differences between normal-appearing WM and DAI sites in the TBI brains. Conversely, multidimensional MRI parameters, primarily T1-T2 and MD-T2, are able to distinguish between injury and normal-appearing regions within TBI brains. The most obvious strength of a multidimensional MRI approach is that it allows for a distribution of parameters to reside within a single voxel, thus potentially significantly increasing the sensitivity to detect more subtle and minor changes. Although shown to be highly predictive of TAI, the T1-T2 SC that contained the injury information ranged, on average, between a few percentage points to 13% of the entire signal, depending on the severity of the injury. In most cases, a simple average would simply mask out the relatively small fraction of affected tissue within a voxel. The multidimensional MRI TAI biomarkers disclosed herein can be used as an independent, stand-alone, neuroimaging tool to provide injury-only images.

By evaluating voxel-averaged and multidimensional relaxation-based MRI approaches, the postmortem ex vivo assessment showed that a significant shortening in both T1 and T2 and a corresponding increase in the TAI SCs occurred in DAI regions in the corpus callosum, compared to both normal-appearing regions within the group and healthy controls. Although a significant drop in the voxel-averaged T1 and T2 values compared with healthy controls was observed in some of the cases (Table 2 in FIGS. 18A-18B), only the voxel-averaged T1 survived the group comparison (Table 3 in FIG. 18C). These voxel-averaged relaxation parameters were not significantly reduced when compared with normal-appearing WM in mild- and severe TAI CCs (Table 4 in FIGS. 18D-18E).

Relaxation is a process of molecular motion, interaction and energy exchange and as such T1 and T2 are directly influenced by local biophysical structure and biochemical environment. In particular, macromolecules such as proteins, are generally known to shorten T1 and T2. Consistent with the findings disclosed herein, it is known that impaired axonal transport due to trauma induces long-term pathological co-accumulation of APP and other intra-axonal proteins. It is possible that pathologically accumulated APP (and possibly other proteins) acts as a relaxation enhancer to its water microenvironment and is therefore the reason for the strong correlation observed here between the short T1-short T2 components and the APP density.

The findings of decreased T1 and T2 are in contrast with previous animal models studies that reported an increase in T2 following TBI. The increase in T2 in other studies has been associated with edema and hemorrhage. In animal models of TBI, where moderate to severe injury is prevalent, macroscopic damage that causes edema and hemorrhage may dominate the MRI signal. Most of the cases described herein are associated with survival times greater than 14 days in which edema generally resolved. Of the three acute cases with survival time under 7 days (Cases 1, 4, and 5), edema and loss of tissue were observed only in Case 1 (care was taken such that none of the analyzed tissue blocks were taken from that area).

DTI metrics are considered to be sensitive to microstructural alterations due to TBI but such metrics can inconsistent in their observed response. As with relaxation-based MRI methods, DTI findings may be affected by cellular edema. While in many cases, the FA has been reported to decrease, a meta-analysis study of hundreds of patients showed elevated FA in participants with history of TBI and highlighted the heterogeneity of these injuries. The non-specificity of FA can be attributed to the heterogeneity of TBI, and to the complexity of WM both in terms of molecular composition and neuro-architectural structure. Complex WM architecture can introduce greater variation of orientation dispersion, consequently resulting in decreased FA, regardless of the underlying injury. Reflecting this inconsistency, FA presented a large variability in all groups that had led to insignificant changes due to injury.

Common to all ex vivo human MRI studies, the data include the effects of post-mortem degeneration, fixation and resulting dehydration. First, the fixation process by itself changes the tissue properties, such that a direct comparison with in vivo data is not possible. In the case of human tissue, the delayed fixation (i.e., post-mortem interval) affects the measured MRI parameters as well which further complicates comparison with in vivo human results. The PMI in the disclosed example was reasonably homogenous, with 7 out of the 11 cases under or equal to 12 hours, and the rest under or equal to 30 hours. Moreover, histopathology results indicate preservation of APP and other immunostains in all samples regardless of PMI. Although both fatal and nonfatal TBI outcomes were included, this design results in inherently heterogenous survival time, which presents a limitation. Glia reactivity, which is highly dependent on the time from injury, cannot be controlled for and cannot be ruled out as a contributing factor to the disclosed MRI findings.

This example of the disclosed approaches demonstrates noninvasive detection of mTBI related pathology with high specificity. TAI has a unique multidimensional spectral signature, which can be used to generate TAI biomarker images that closely follow APP histopathology: APP-positive areas scale with multidimensional TAI biomarker intensity, and negative APP corresponds to complete lack of MRI signal. This specificity of the multidimensional TAI biomarkers allows neuroimaging to serve as a "noninvasive histology." The T1-T2-MD range identified is specifically linked to TAI microscopic tissue alterations, information that will help clinical investigators in their search for DAI lesions in the brain. However, because T1, T2, and diffusion dynamics are different in fixed tissue compared with living systems, the range of TAI-specific multidimensional MR parameters to be used in detection may be different in in vivo.

Characteristic Multidimensional MRI Signature for Diffuse Axonal Injury

MRI Acquisition

The acquisition of multidimensional data was done using echo planar imaging (EPI) readout according to the MADCO framework encoding scheme and by varying the following three experimental parameters: the inversion time, $\tau_1$, the echo time, $\tau_2$, and the diffusion weighting, b, providing T1-, T2-, and diffusion-weighting, respectively.

The minimal values of the two timing parameters, $\tau_1$ and $\tau_2$, depend on the sample physical dimensions because of the varying imaging matrix size that is intended to keep the spatial resolution constant at 300 μm isotropic. The minimal $\tau_1$ and $\tau_2$ were kept relatively constant across the samples at $\tau1=12:0\pm1:5$ ms and $\tau2=10:5\pm0:8$ ms, by adjusting the number of EPI segments as necessary (<8).

The three 1D distributions of T1, T2, and MD, were estimated, respectively, with the following data acquisition protocols: A 1D T1-weighted data set (b=0, $\tau2=10:5$ ms) with 20 logarithmically sampled $\tau1$ values ranging from 12 to 980 ms by using an IR-DWI-EPI sequence; a 1D T2-weighted data set (b=0) with 20 logarithmically sampled $\tau2$ values ranging from 10.5 to 125 ms by using a DWI-EPI sequence. For diffusion encoding, we used the isotropic generalized diffusion tensor MRI (IGDTI) acquisition protocol to achieve an efficient orientationally averaged DW signal with the following parameters: 16 linearly sampled b-values ranging from 2,540 to 14,700 s/mm² in 3 directions, 14 linearly sampled b-values ranging from 4,140 to 14,700 s/mm² in 4 directions, and 9 linearly sampled b-values ranging from 8,260 to 14,700 s/mm² in 6 directions, using the efficient gradient sampling schemes in Table 2 in Avram et al., "Efficient experimental designs for isotropic generalized diffusion tensor MRI (IGDTI)," *Magn. Res. Med.* 271:40-45 (2018) which is incorporated herein by reference. This type of diffusion encoding increases the contrast given by local anisotropy and is not intended to measure the isotropic diffusion in the system. Additional diffusion parameters were gradient duration of $\delta=4$ ms and diffusion time of $\Delta=15$ ms.

The three 2D distributions of MD-T1, MD-T2, and T1-T2, were estimated, respectively, with the following data acquisition protocols (in conjunction with the a priori obtained 1D distributions as constraints): A 2D diffusion-T1-weighted data set with 16 sampled combinations of inversion times and b-values within the aforementioned 1D acquisition range; a 2D D-T2-weighted data set with 16 sampled combinations of echo times and b-values within the aforementioned 1D acquisition range; and a 2D T1-T2-weighted data set with 16 sampled combinations of inversion and echo times within the aforementioned 1D acquisition range. The data were averaged 4 times to maintain high signal-to-noise ratio (SNR), which was always maintained above 100 (defined as the ratio between the average unattenuated signal intensity within a tissue region of interest, and the standard deviation of the signal intensity within the background). The sample temperature was set at 16.8° C.

Multidimensional MRI Processing

The 2D T1-T2, MD-T1, and MD-T2 distributions were evaluated on logarithmically sampled grids. The range for T1 was 1 10,000 ms, the range for T2 was 1 500 ms, and the range for MD was 0.0001 5 μm²/ms.

Two factors guided the search for injury-associated spectral ROIs: (1) the injury is primarily a WM injury, and (2) the T1-T2-MD range of what is deemed as normal WM. It was to be shown that microscopic WM injury would affect the normal WM spectral component, and that the axonal injury spectral information would be found in the vicinity of the normal WM component. Based on this notion, a T1-T2-MD range, T1=[91.03, 339.32] ms, T2=[6.70, 34.85] ms, and MD=[0.004, 0.146]μm²/ms has been identified in which the presence of injury-associated spectral information is observed. Because of normal biological variability and also potential fixation variability effects (i.e., PMI), different cases presented slightly different multidimensional distributions. Therefore a further per-case adjustment was performed to locate the most relevant portion of the spectra within the pre-selected T1-T2-MD range.

Figure 12A:
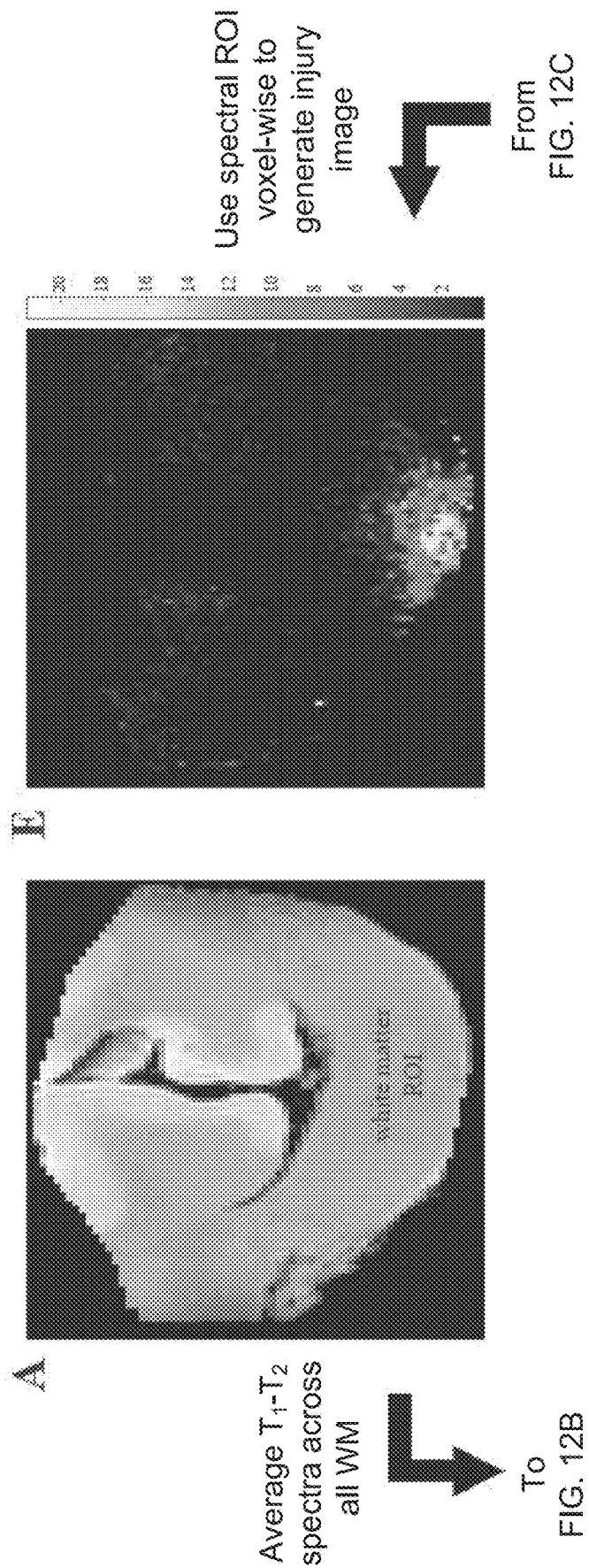
FIGS. 12A-12C illustrate the spectral ROI definition process, shown on the T1-T2 data set of Case 4. (A) White matter segmented based on the FA, and all T1-T2 distributions are averaged across the WM ROI, yielding (B) an WM-average T1-T2 spectrum. (C) A magnification of the pre-selected T1-T2 range. (D) An edge detection procedure (using a standard adaptive threshold algorithm) in the spectral domain is performed to identify the edge of the normal-appearing WM spectral component. Once that edge is found, the spectral ROI is defined such that it would exclude the normal WM spectral information and include the rest of the T1-T2 range, based on our hypothesis that the injury-associated spectral information would be found in the vicinity of the normal WM component. (E) The spectral ROI is then applied voxel-wise on the T1-T2 distributions data set, which yields an image of the axonal injury spectral component.
Figure 12B:
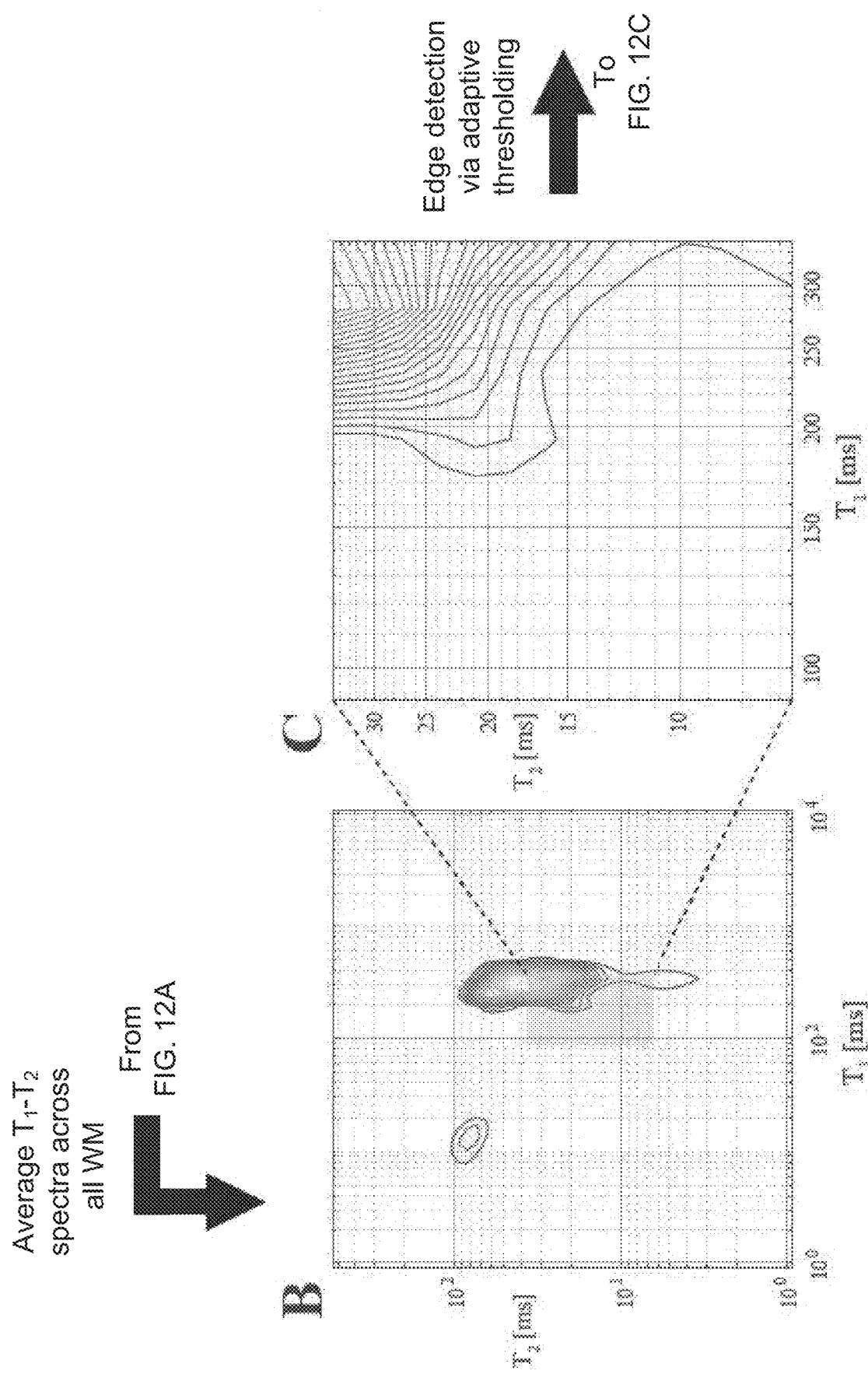
Figure 12C:
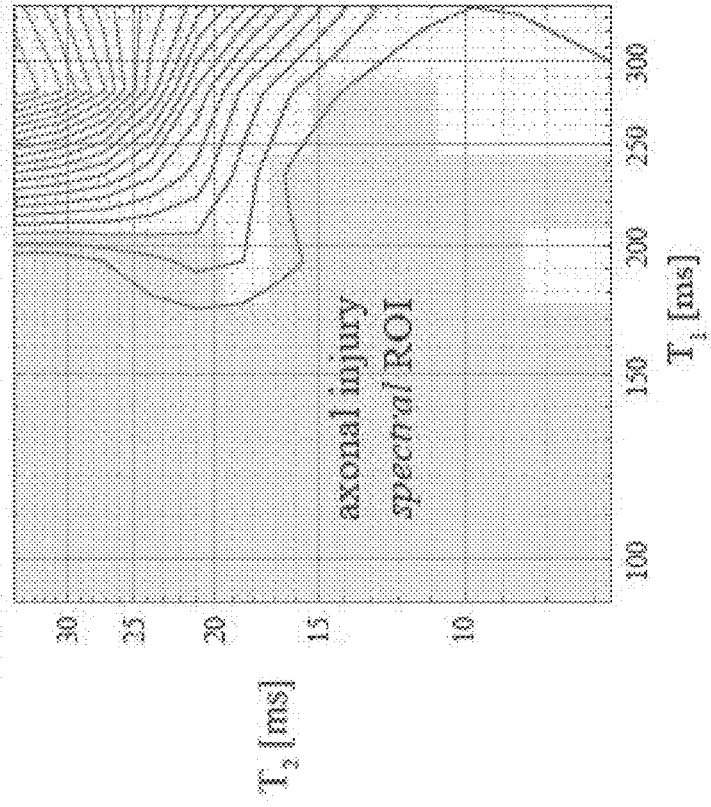

Because of the sparsity of TAI lesions in the CC, the injury-indicative spectral information is undetectable when looking at the multidimensional distributions averaged over the entire CC. However, those averaged distributions can be used to identify the border between normal and abnormal tissue within the aforementioned T1-T2-MD range. An adaptive threshold was applied to find the edge of the spectral peak that resides within the pre-defined T1-T2-MD range. That spectral peak is mostly normal WM tissue, and anything outside of that peak, as defined by the detected edges, was considered related to the axonal injury, and was defined as the spectral ROI. A schematic illustration of the process can be found in A-E from FIGS. 12A-12C.

Repeatability and Reproducibility Assessment of Multidimensional MRI

Figure 13A:
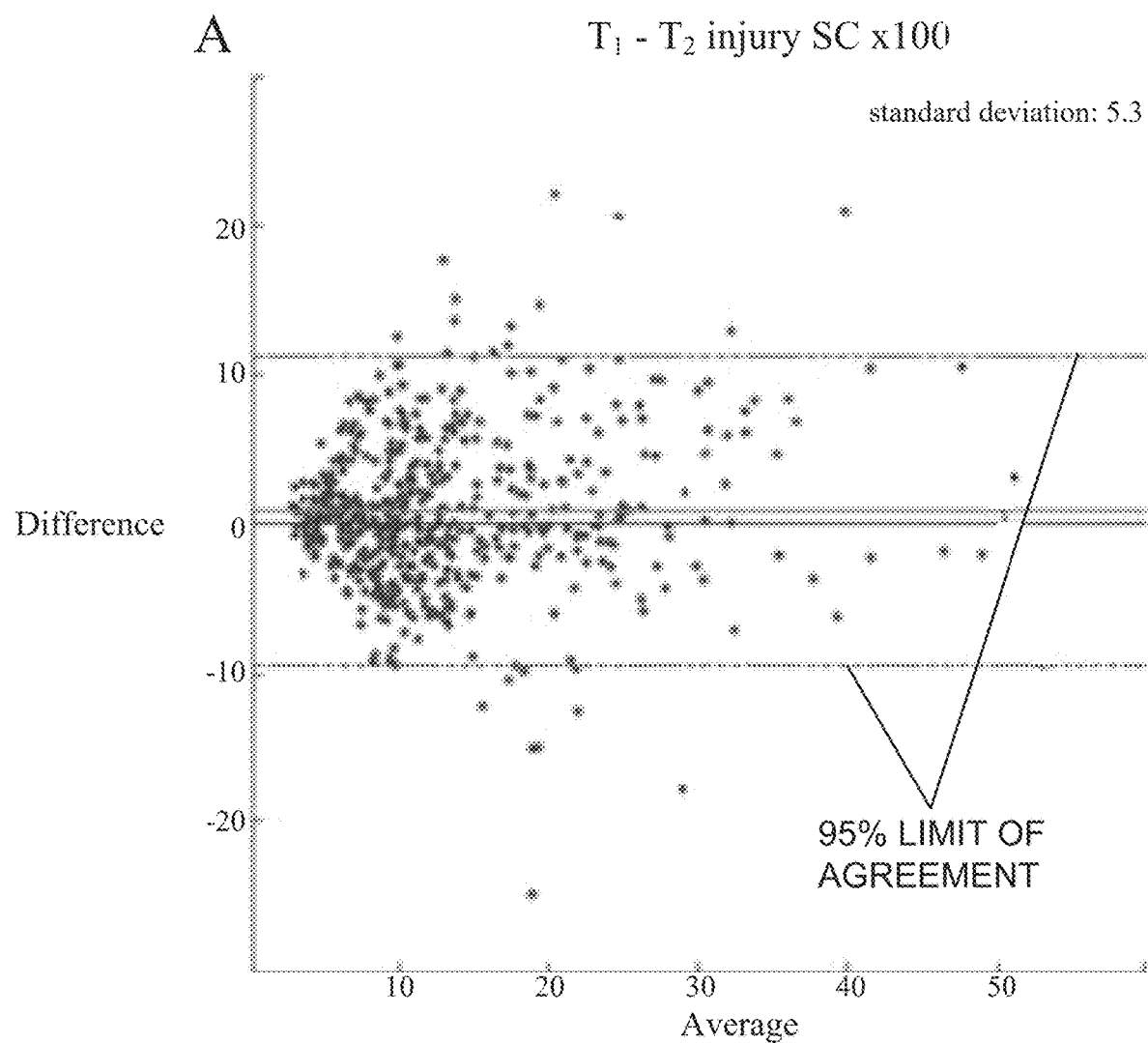
FIGS. 13A-13C illustrate repeatability of the multidimensional MRI pipeline. Two separate multidimensional datasets were acquired from the same ex vivo tissue block (Case 1) using identical acquisition parameters.
Figure 13B:
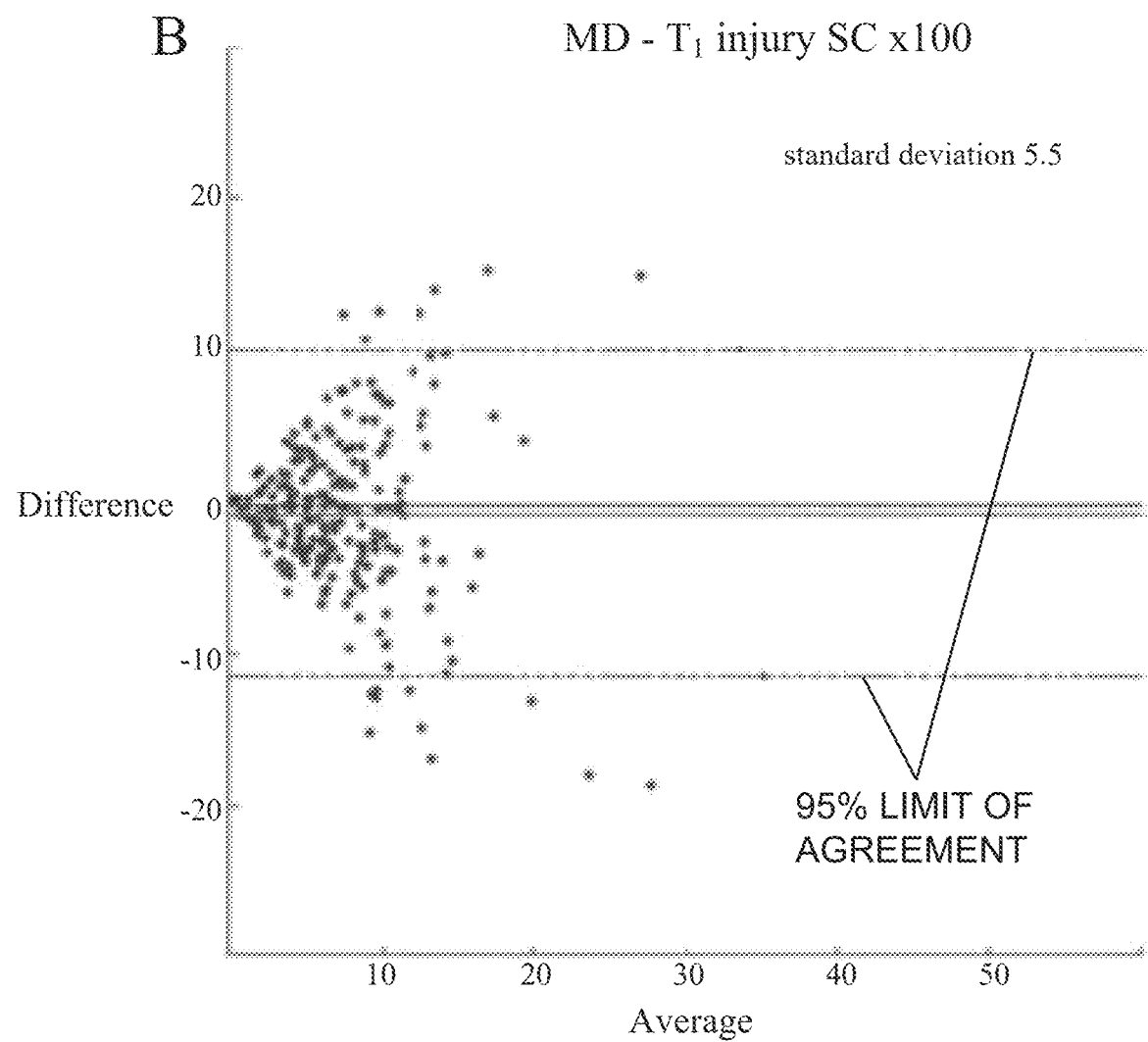
Figure 13C:
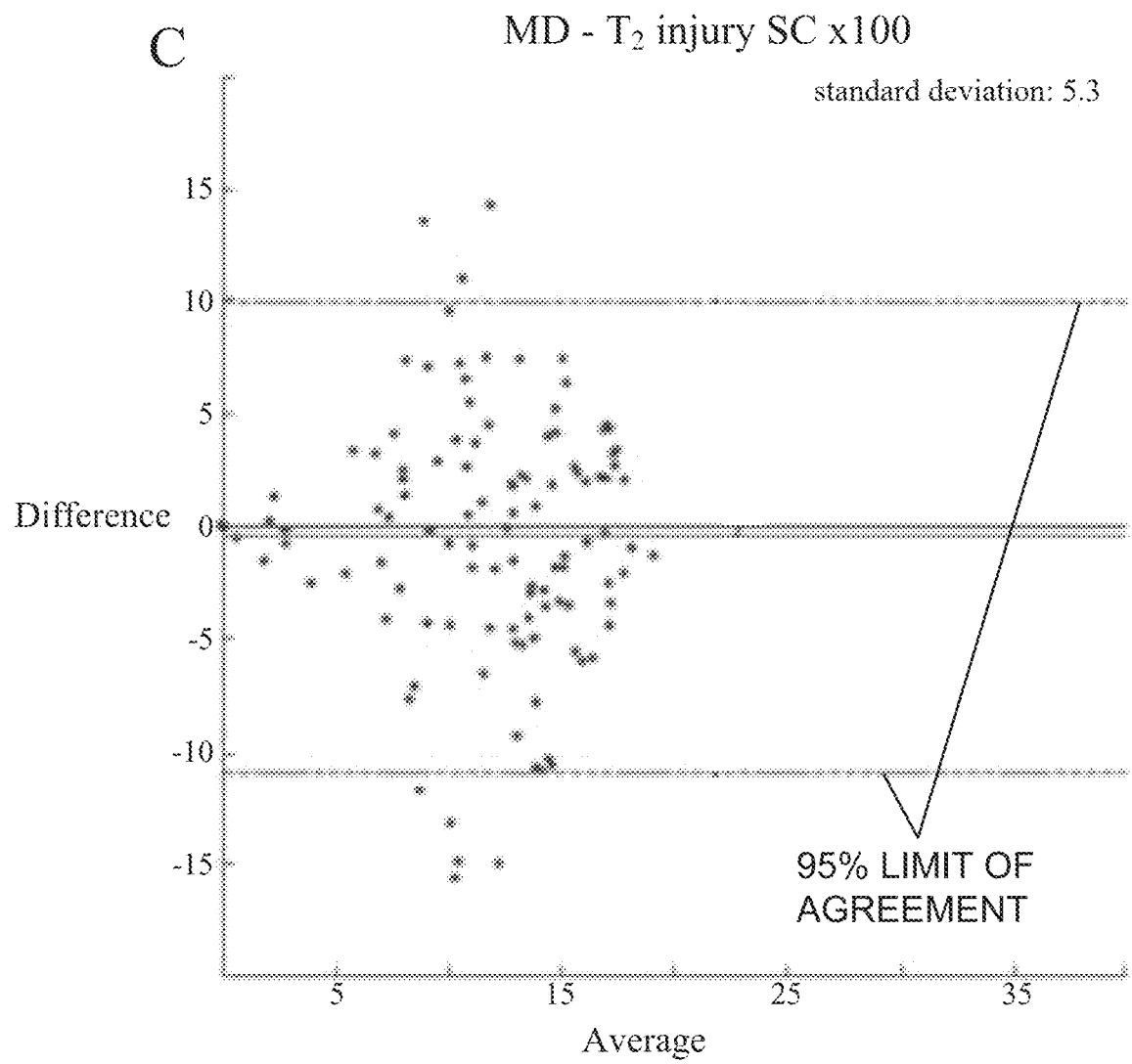
Figure 14A:
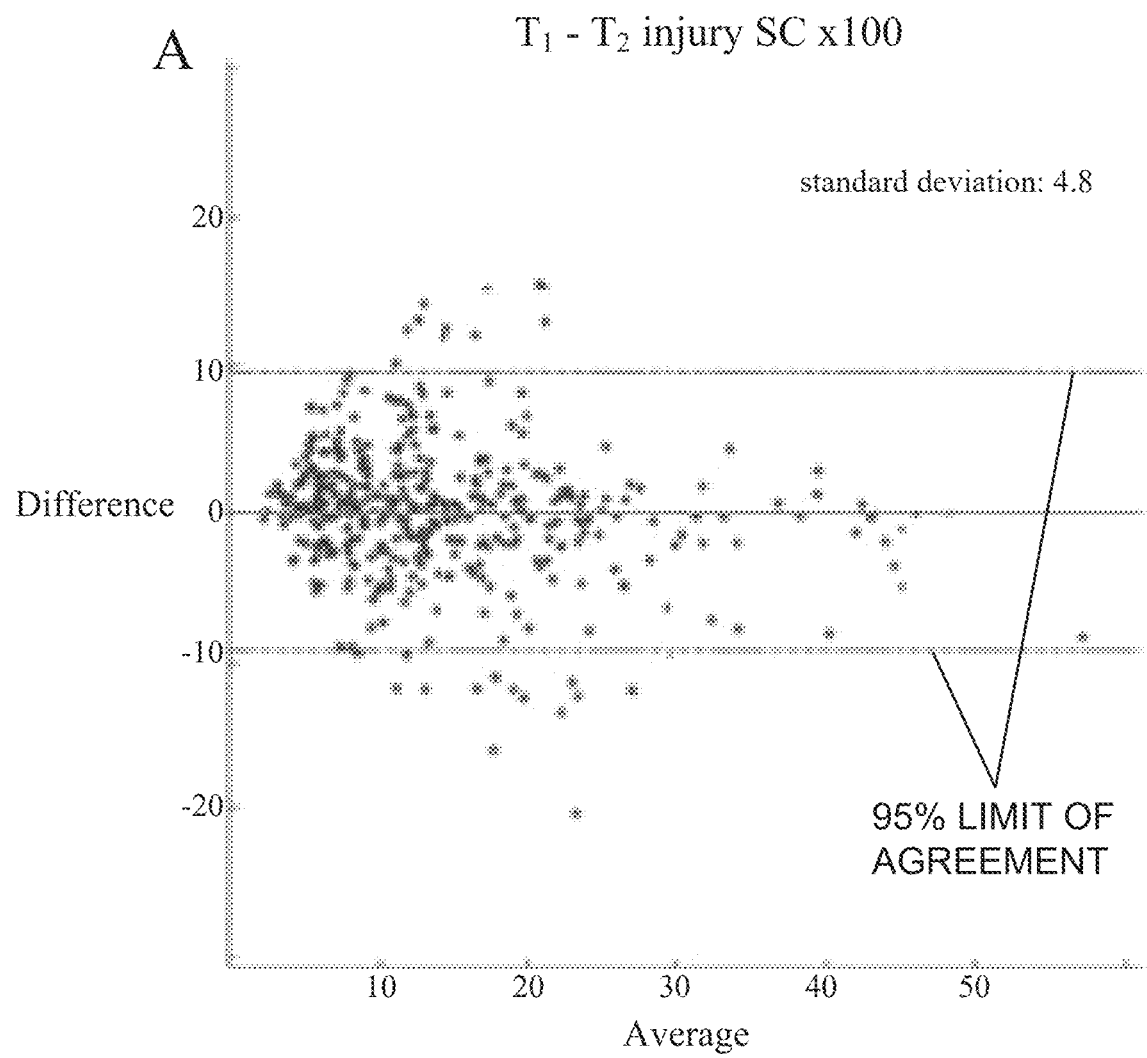
FIGS. 14A-14C illustrate repeatability of the multidimensional MRI pipeline. Two separate multidimensional datasets were acquired from the same ex vivo tissue block (Case 2) using identical acquisition parameters. The (A) T1-T2, (B) MD-T1, and (C) MD-T2 TAI SCs were then calculated in each voxel for each dataset and compared using Bland-Altman plots. High agreement between the two repeated acquisitions was observed for T1-T2, MD-T1, and MD-T2.
Figure 14B:
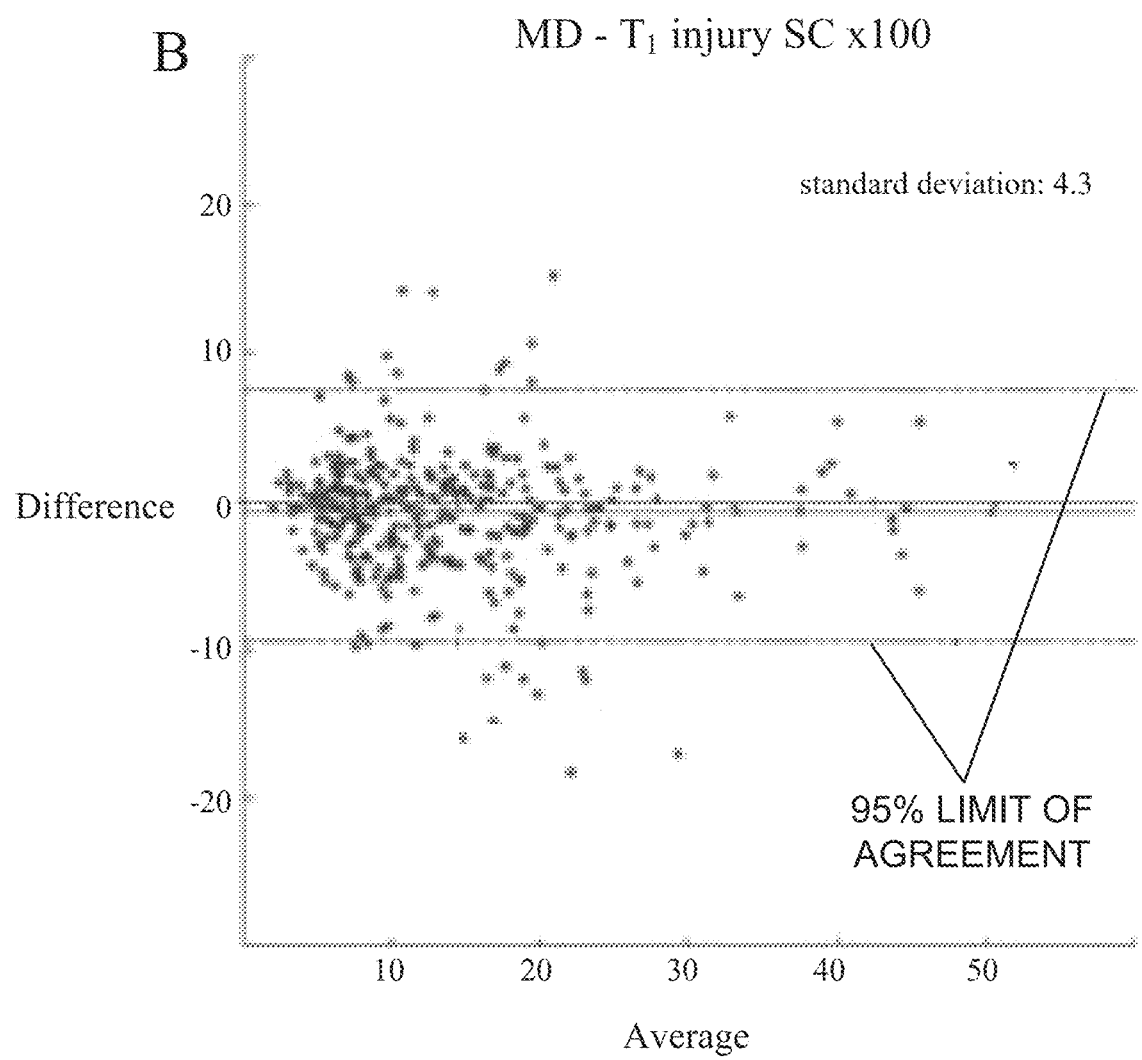
Figure 14C:
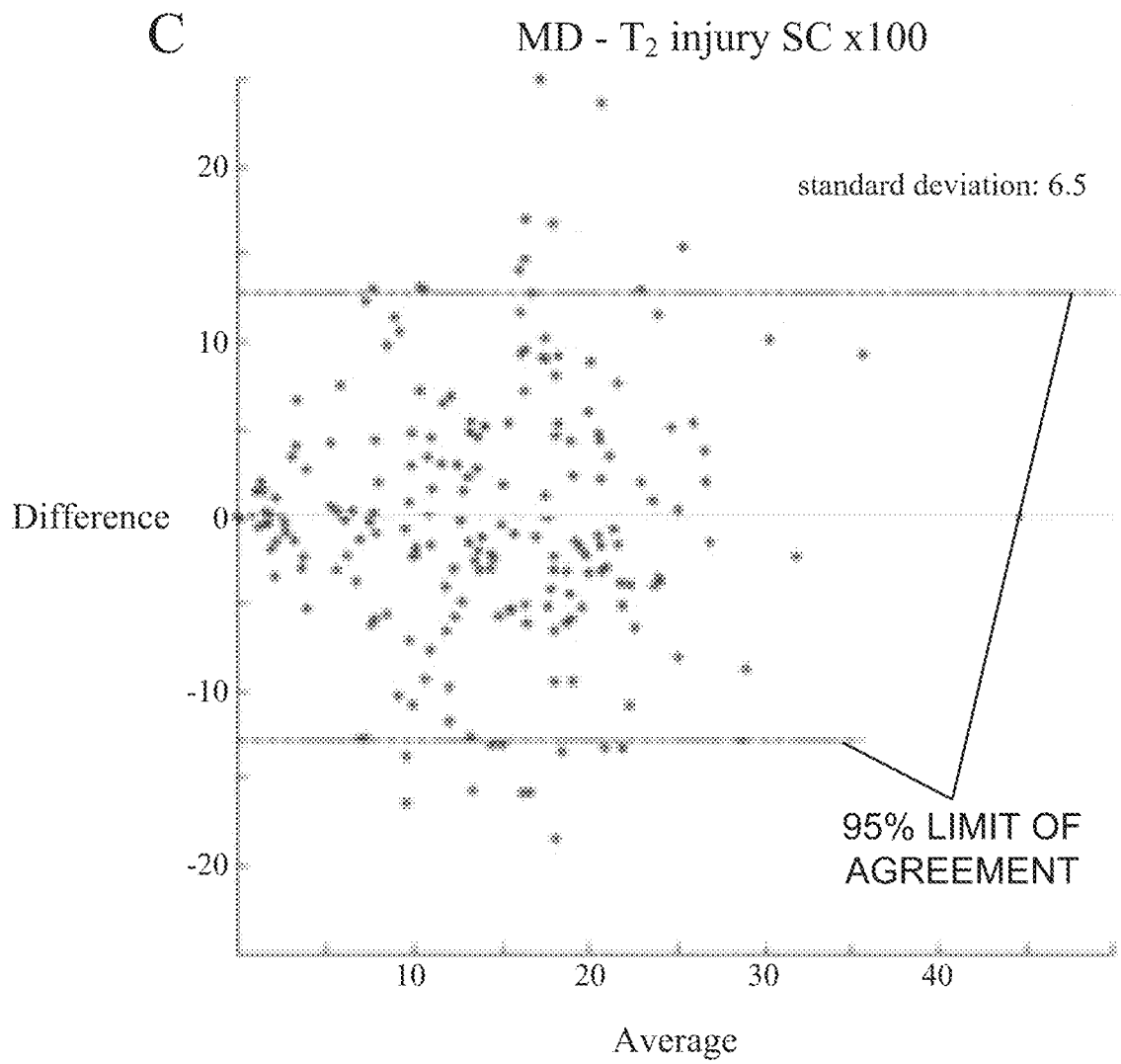

Repeatability and reproducibility of the T1-T2, MD-T1, and MD-T2 TAI SC images were evaluated by repeating the multidimensional MRI acquisitions for Cases 1 and 2. For each of these subjects, the duplicate data sets were processed using the same pipeline and then compared. The TAI SC images of each of these cases were estimated twice, using the two independently acquired data sets. The resulting images were then compared using Bland-Altman plots to quantify the degree of repeatability and reproducibility. Specifically, to avoid including insignificant voxels, all voxels that had very small intensity values (<0:0001) were eliminated first. If one considered the duplicate acquisitions of each of the cases as paired measurements, the Bland-Altman plot display the difference of the two paired measurements against the mean of the two measurements. The standard deviation of the measurement error in Case 1 was 5.3 for T1-T2 injury SC, 5.5 for MD-T1 injury SC, and 5.3 for MD-T2 injury SC (FIGS. 13A-13C), and in Case 2 it was 4.8 for T1-T2 injury SC, 4.3 for MD-T1 injury SC, and 6.5 for MD-T2 injury SC (FIGS. 14A-14C).

Additional Results

Figure 15A:
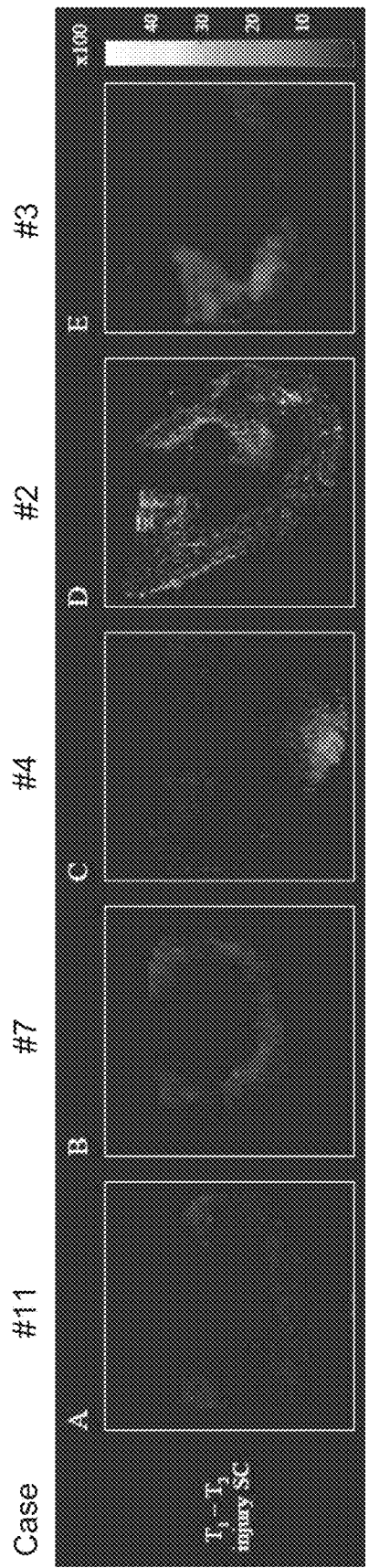
FIGS. 15A-15C contain multidimensional injury images of several examined cases with increased severity.
Figure 15B:
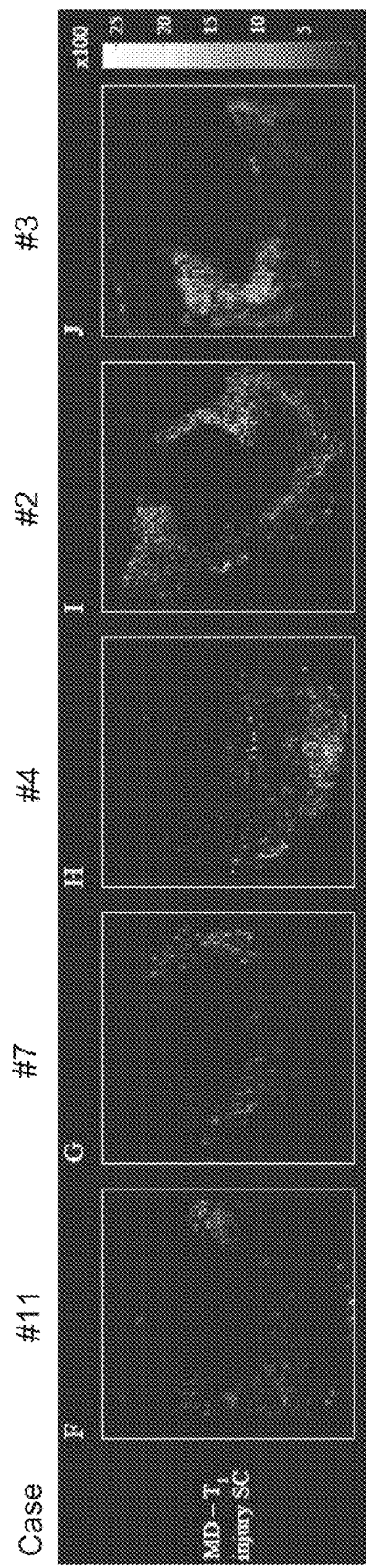
Figure 15C:
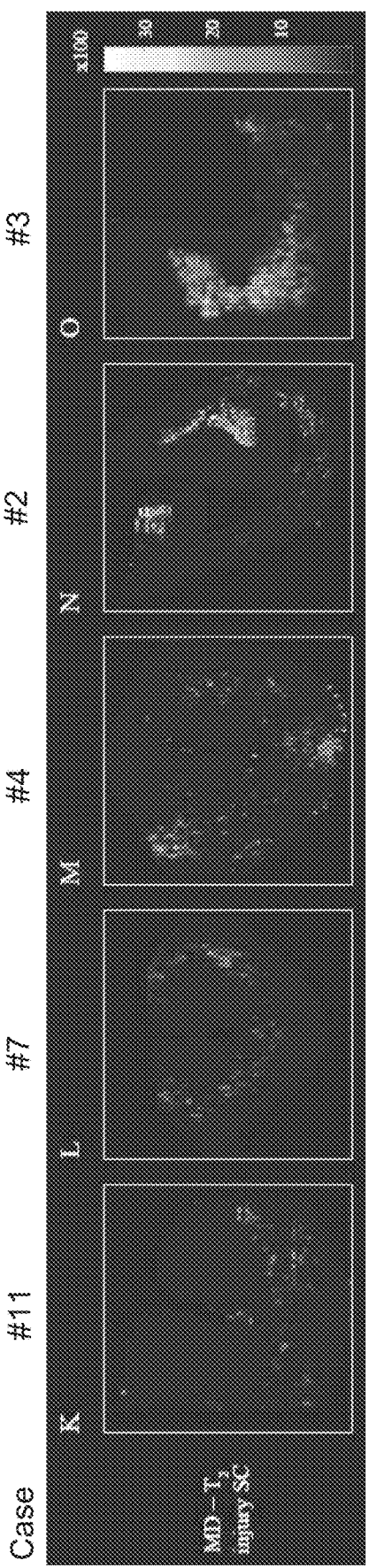
Figure 16A:
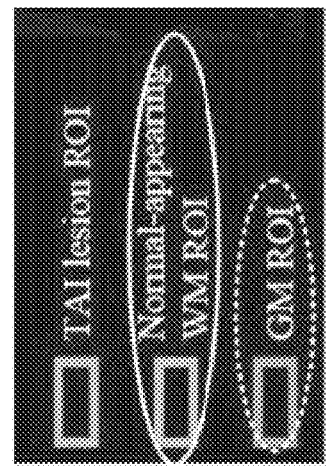
Figure 16A:
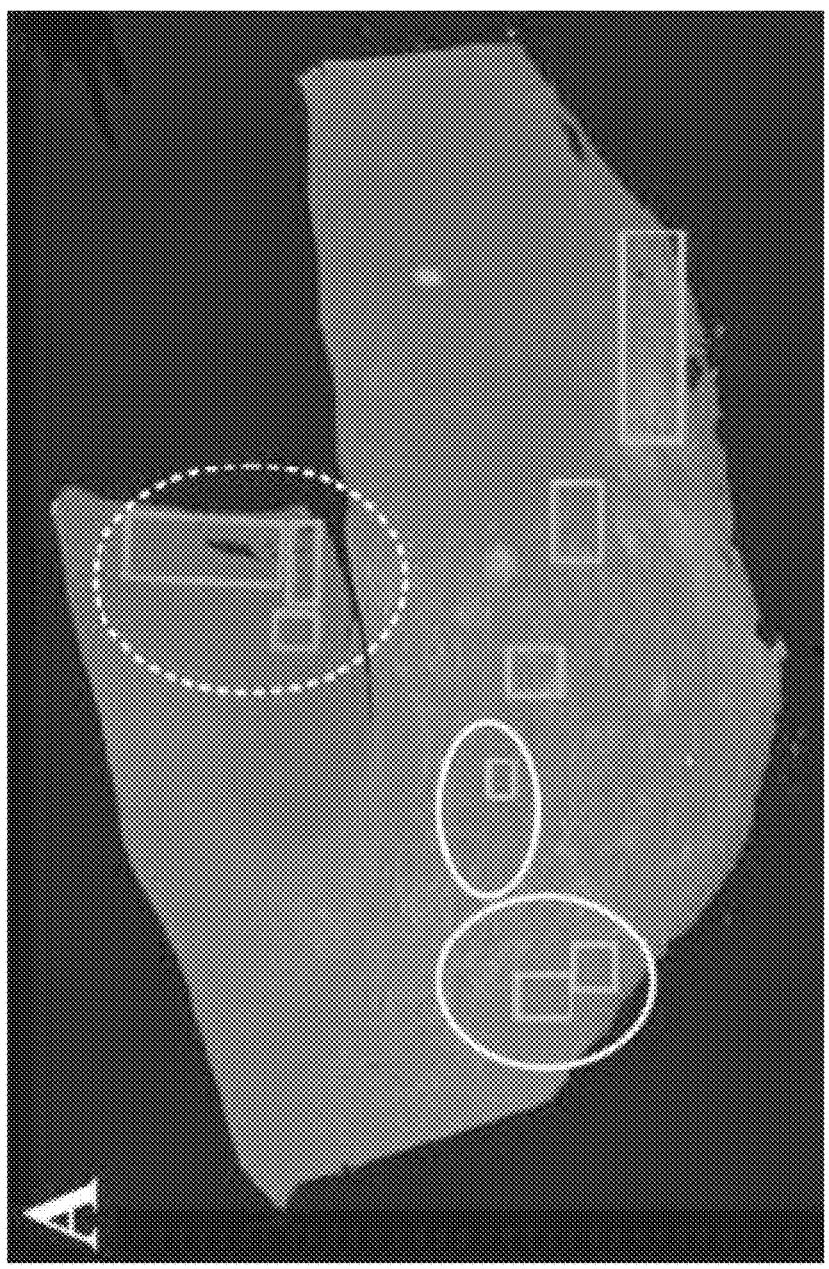
Figure 16B:
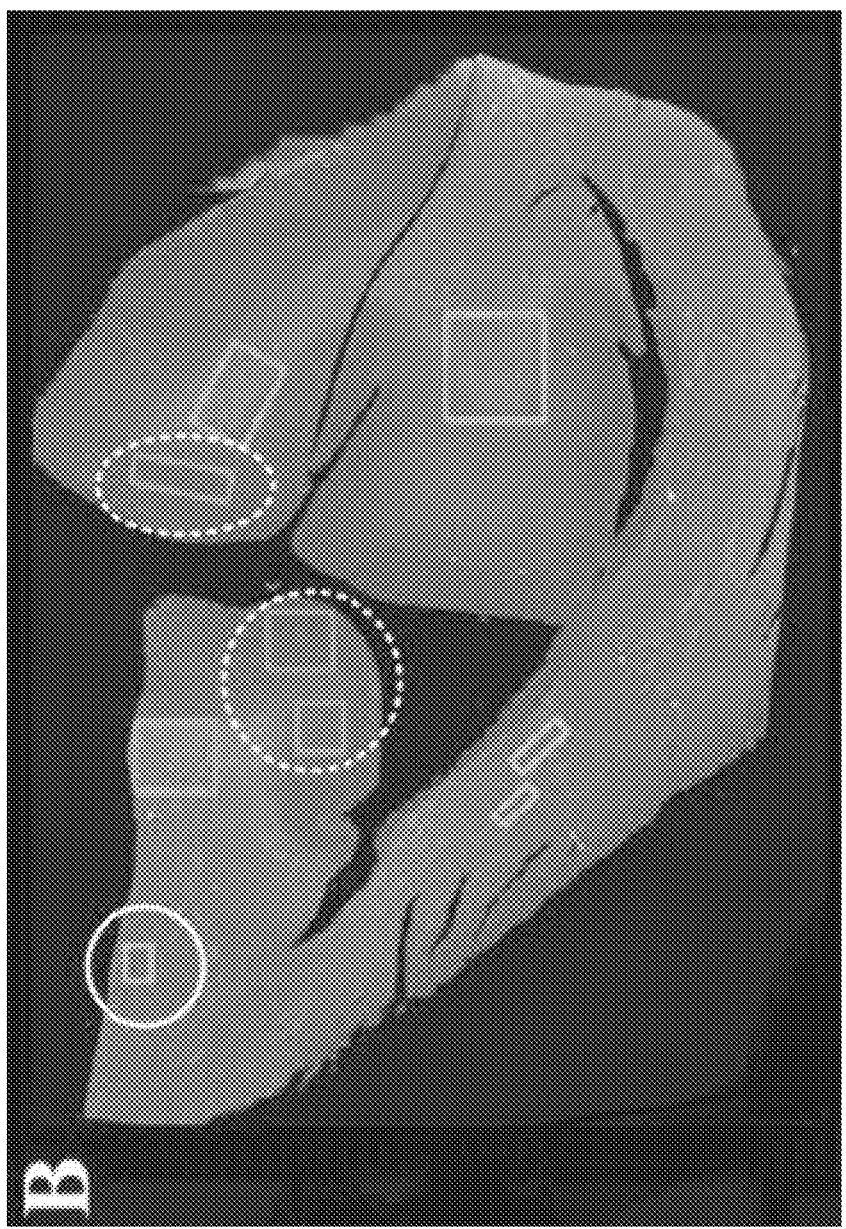
Figure 16B:
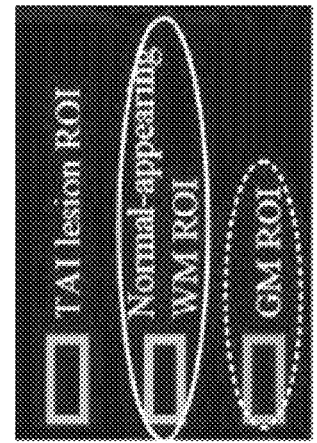
Figure 16D:
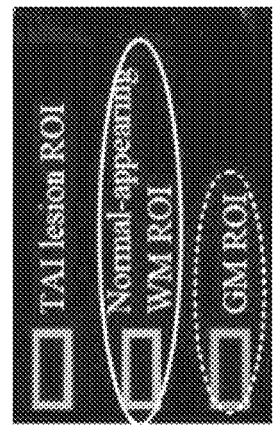
Figure 16D:
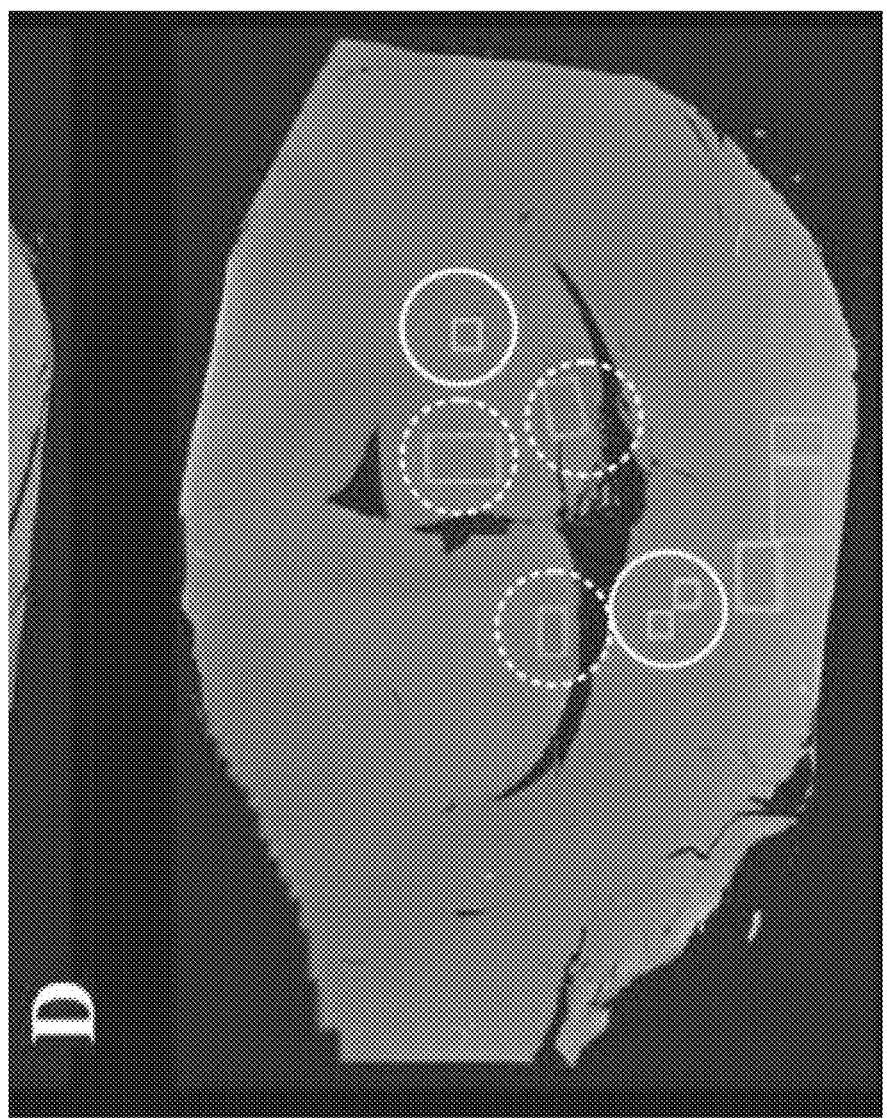

FIGS. 15A-15C contain multidimensional injury images of several examined cases with increased severity. (A) $T_1$-$T_2$, (F) MD-$T_1$, and (K) MD-$T_2$ injury images of control CC (Case 11) show negligible image intensities. (B) $T_1$-$T_2$, (G) MD-$T_1$, and (L) MD-$T_2$ TAI images of nonfatal TBI with mild APP staining CC (Case 7) show slightly increased image intensities, compared to Case 11. (C) $T_1$-$T_2$, (H) MD-$T_1$, and (M) MD-$T_2$ injury images of fatal TBI with severe APP staining CC (Case 4) show clear localization of extensive WM damage. (D) $T_1$-$T_2$, (I) MD-$T_1$, and (N) MD-$T_2$ injury images of fatal TBI with severe APP staining CC (Case 2) show damage mostly at the GM-WM interface. (E) $T_1$-$T_2$, (J) MD-$T_1$, and (O) MD-$T_2$ injury images of fatal TBI bilateral damage with strong presence in the left side of the CC.

FIGS. 16A-16D show deconvolved histological images of (A) Case 1, (B) Case 2, (C) Case 6, and (D) Case 4, with their defined regions of interest. Normal appearing WM ROIs are shown circled with solid lines, GM ROIs are shown circled with dotted lines, and the remaining ROIs are associated with TAI lesions.

FIGS. 19A-19B are tables of comparisons of MRI parameters and pathological measures among control WM, mild TAI (mTAI), severe TAI (sTAI), normal-appearing WM in mTAI and sTAI tissue regions.

Representative Data Acquisition and Control Apparatus

Figure 9:
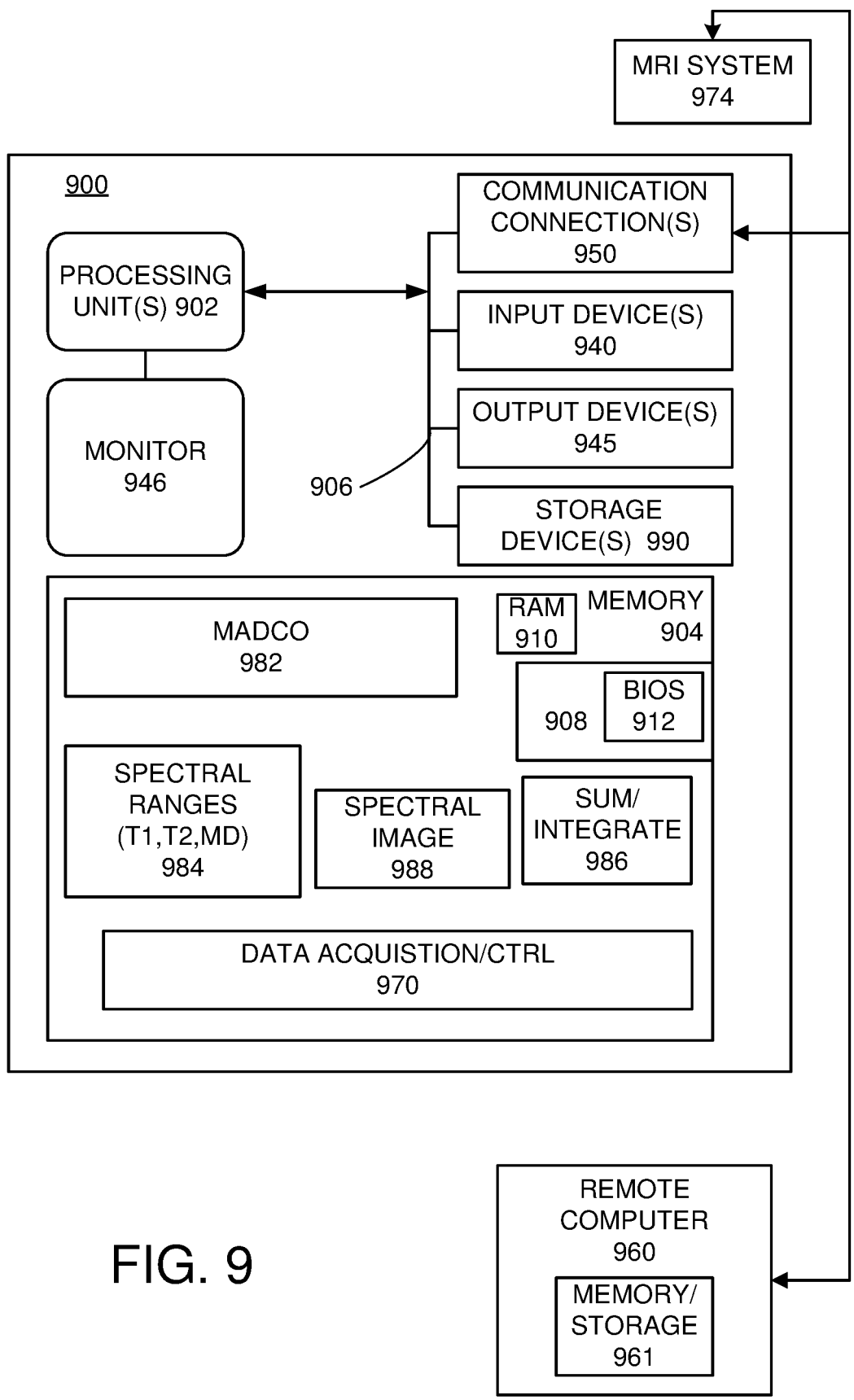
FIG. 9 illustrates a representative computing and control environment for any of the disclosed methods.

FIG. 9 and the following discussion are intended to provide a brief, general description of an exemplary computing/data acquisition environment in which the disclosed technology may be implemented. Although not required, the disclosed technology is described in the general context of computer executable instructions, such as program modules, being executed by a personal computer (PC), a mobile computing device, tablet computer, or other computational and/or control device. Generally, program modules include routines, programs, objects, components, data structures, etc., that perform particular tasks or implement particular abstract data types. Moreover, the disclosed technology may be implemented with other computer system configurations, including hand held devices, multiprocessor systems, microprocessor-based or programmable consumer electronics, network PCs, minicomputers, mainframe computers, and the like. The disclosed technology may also be practiced in distributed computing environments where tasks are performed by remote processing devices that are linked through a communications network. In a distributed computing environment, program modules may be located in both local and remote memory storage devices.

With reference to FIG. 9, an exemplary system for implementing the disclosed technology includes a general purpose computing device in the form of an exemplary conventional PC 900, including one or more processing units 902, a system memory 904, and a system bus 906 that couples various system components including the system memory 904 to the one or more processing units 902. The system bus 906 may be any of several types of bus structures including a memory bus or memory controller, a peripheral bus, and a local bus using any of a variety of bus architectures. The exemplary system memory 904 includes read only memory (ROM) 908 and random access memory (RAM) 910. A basic input/output system (BIOS) 912, containing the basic routines that help with the transfer of information between elements within the PC 900, is stored in ROM 908.

The exemplary PC 900 further includes one or more storage devices 990 such as a hard disk drive for reading from and writing to a hard disk, a magnetic disk drive for reading from or writing to a removable magnetic disk, an optical disk drive for reading from or writing to a removable optical disk (such as a CD-ROM or other optical media), and a solid state drive. Such storage devices can be connected to the system bus 906 by a hard disk drive interface, a magnetic disk drive interface, an optical drive interface, or a solid state drive interface, respectively. The drives and their associated computer readable media provide nonvolatile storage of computer-readable instructions, data structures, program modules, and other data for the PC 900. Other types of computer-readable media which can store data that is accessible by a PC, such as magnetic cassettes, flash memory cards, digital video disks, CDs, DVDs, RAMs, ROMs, and the like, may also be used in the exemplary operating environment.

A number of program modules may be stored in the storage devices 990 including an operating system, one or more application programs, other program modules, and program data. A user may enter commands and information into the PC 900 through one or more input devices 940 such as a keyboard and a pointing device such as a mouse. Other input devices may include a digital camera, microphone, joystick, game pad, satellite dish, scanner, or the like. These and other input devices are often connected to the one or more processing units 902 through a serial port interface that is coupled to the system bus 906, but may be connected by other interfaces such as a parallel port, game port, or universal serial bus (USB). A monitor 946 or other type of display device is also connected to the system bus 906 via an interface, such as a video adapter. Other peripheral output devices, such as speakers and printers (not shown), may be included.

The PC 900 may operate in a networked environment using logical connections to one or more remote computers, such as a remote computer 960. In some examples, one or more network or communication connections 950 are included. The remote computer 960 may be another PC, a server, a router, a network PC, or a peer device or other common network node, and typically includes many or all of the elements described above relative to the PC 900, although only a memory storage device 961 has been illustrated in FIG. 9. The personal computer 900 and/or the remote computer 960 can be connected to a logical a local area network (LAN) and a wide area network (WAN). Such networking environments are commonplace in offices, enterprise wide computer networks, intranets, and the Internet.

When used in a LAN networking environment, the PC 900 is connected to the LAN through a network interface. When used in a WAN networking environment, the PC 900 typically includes a modem or other means for establishing communications over the WAN, such as the Internet. In a networked environment, program modules depicted relative to the personal computer 900, or portions thereof, may be stored in the remote memory storage device or other locations on the LAN or WAN. The network connections shown are exemplary, and other means of establishing a communications link between the computers may be used.

The memory 904 generally includes computer-executable instructions for selecting gradient fields G1, G2, averaging acquired signals, and any calculations based in acquired signals. For example, memory portion 982 can store computer-executable instructions for MADCO procedures discussed above and identified spectral ranges associated with injury can be stored in a memory portion 984. Computer-executable instructions for summing or integrating or otherwise processing spectral values within an identified spectral window can be stored at 986 and spectral images based on this processing and exhibiting injury or other specimen characteristic can be stored at 988. Computer-executable instructions for data acquisition and control are stored in a memory portion 970. Acquired and processed data (e.g., images based on mean diffusion tensor images) can be displayed using computer-executable instructions stored as well. As noted above, data acquisition, processing, and instrument control can be provided at an MRI system 974, or distributed at one or more processing devices using a LAN or WAN.

Additional Representative Diffusion-Based Signatures

The examples disclosed above use TBI signatures associated with T1, T2, and MD. However, other diffusion-based schemes can be used. For example, any or all of the diffusion-encoded acquisitions based on the trace of b (size), the normalized anisotropy of b (shape), and the orientation of an axisymmetric encoding tensor b can be used. Generally, these four acquisition dimensions can be used to probe the four dimensions of microscopic axisymmetric diffusion tensors. This tensor-valued diffusion encoding can replace orientationally averaged diffusion acquisition. In such cases, instead of the mean diffusivity (MD), the probed diffusion dimensions could be the isotropic diffusion, the diffusion shape, and diffusion orientation. For example, instead of the distribution of MD-T$_2$, a tensor-valued diffusion encoding would result in estimation of the distribution of D$_{iso}$-D$_A$-θ-φ-T$_2$, where D$_{iso}$ is the isotropic diffusivity (average rate of water diffusion), the diffusion anisotropy D$_A$ (tendency for diffusion to occur along a specific orientation (θ,)) and the diffusion orientation (θ,). Any multidimensional combination of D$_{iso}$, D$_A$, θ-φ, T$_1$, and T$_2$ can be used.

Figure 10:
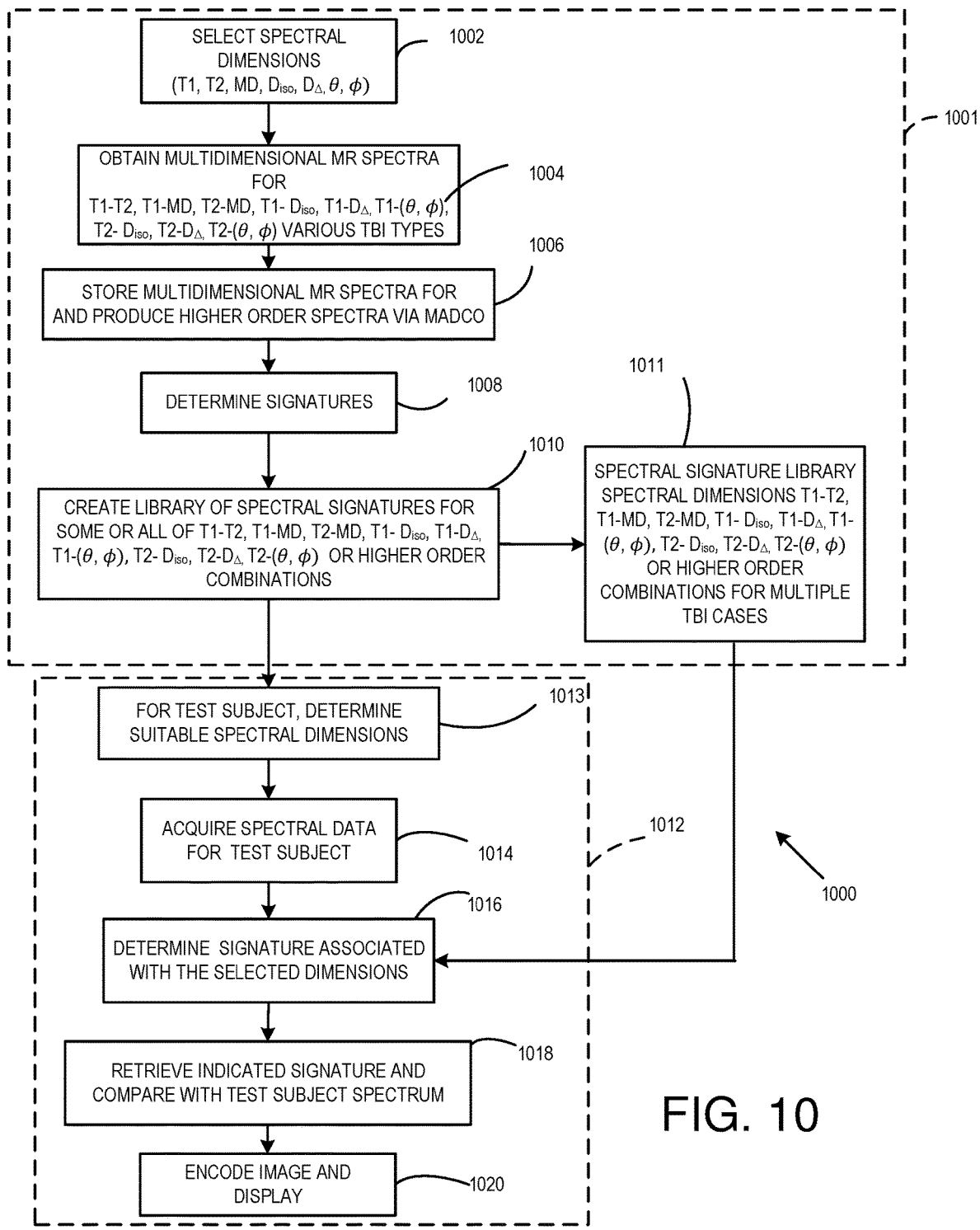
FIG. 10 illustrates a representative method of obtaining spectral signatures and assessing a sample or subject with the spectral signatures.

Referring to FIG. 10, a method 1000 includes a signature acquisition method 1001 associated with signature determination and a subject measurement method 1012 associated with sample or subject evaluation based on the determined signatures. At 1002, spectral dimensions such as D$_{iso}$, D$_A$, θ-φ, T$_1$, and T$_2$ can be selected and at 1004 corresponding multidimensional spectra are obtained for various types of TBI such as TAI, DAI, sTAI, mTAI, and any others. As shown in FIG. 10, two dimensional spectra are obtained and processed at 1006 to produce higher order spectra using the MADCO approach but such spectra can be obtained in other ways. These spectra are stored, and at 1008, signatures are obtained that can be associated with some or all selected types of TBI. At 1010, a library of spectral signatures is created that includes sROIs appropriate for selected types of TBI along with weights obtained from spectral magnitudes in the sROI such as sums of all spectral magnitudes in the sROI. This library is stored at 1011 in one or more local or remote computer readable media. Various combinations of spectral parameters can be selected and a particular type and degree of TBI can be associated with multiple sROIs and weights.

At 1012, for a particular test subject (a lab specimen or a patient), some or all sROIs are selected for determination based on a type and degree of TBI of interest. At 1014, spectral data is acquired that can be used to span the selected sROI(s). At 1016 the spectral signature(s) associated with the sROI(s) are identified. At 1018, the signatures are retrieved from the library 1011 and compared with test subject spectra to assess the test subject. At 1020, an test subject image can be encoded based on the assessments to provide a visual map of TBI.

Representative Diffusion-Based Signature Library

Figure 11:
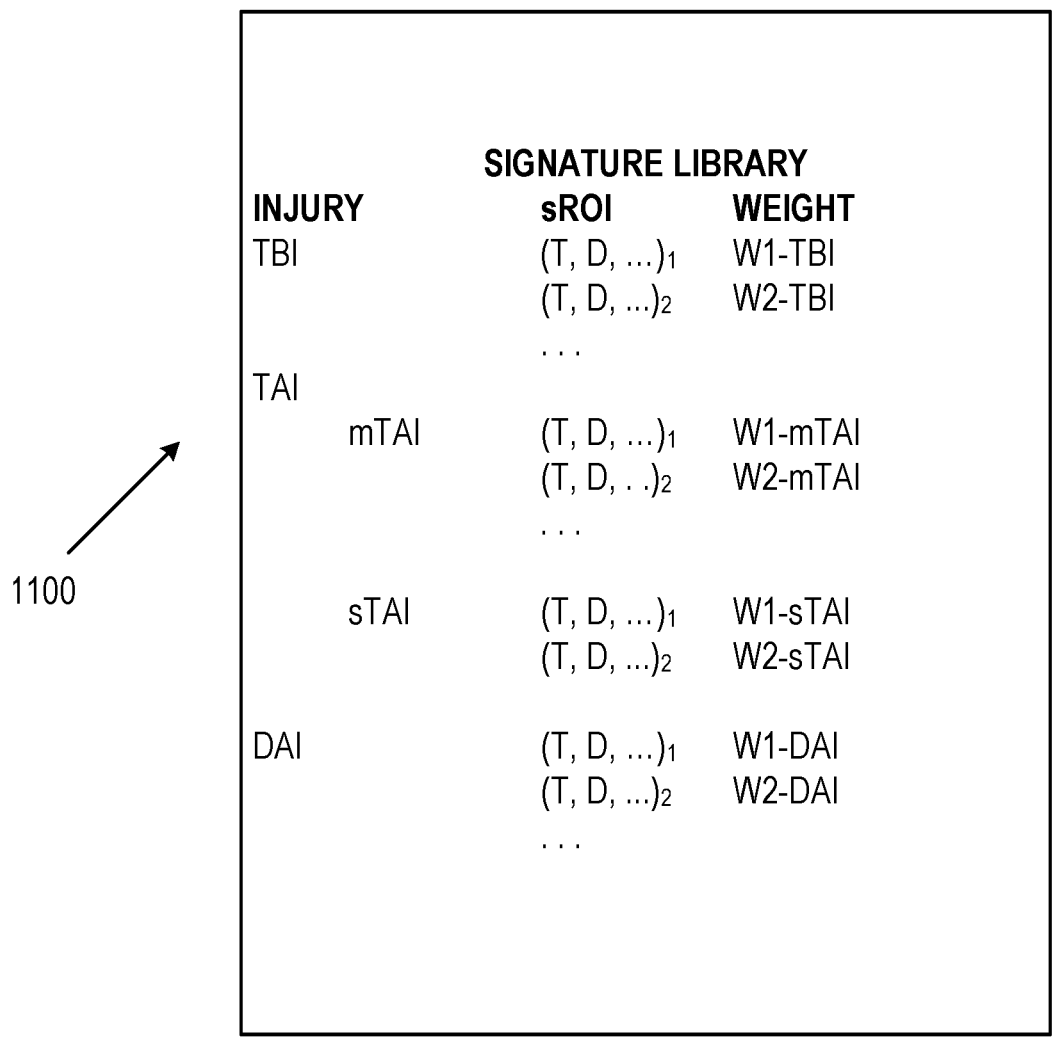
FIG. 11 illustrates a representative MR signature database.

A representative signature library 1100 is illustrated in FIG. 11. In this examples, one or more signatures are provided for various types/degrees of TBI. For example, the library entries noted as associated with TBI include sROIs (T, D, . . . )$_1$, (T, D, . . . )$_2$, . . . and the associated weights W1-TBI, W2-TBI, . . . The sROIs are specified generically in FIG. 11 as including a spectral parameters "T" and "D" which refer to neither, one, or both of T1 and T2 and one or more (or no) diffusion parameters such as MD, D$_{iso}$ and others. The sROIs can be defined by two, three, or more spectral parameters and multiple sROIs can be selected having the same or different spectral dimensions. The weights in the sROIs are assigned as averages, sums, peak values, or other functions of the spectral magnitudes in the sROIs.

In view of the many possible embodiments to which the principles of the disclosure may be applied, it should be recognized that illustrated embodiments are only examples and should not be considered a limitation.

We claim:
1. A method, comprising:
   obtaining specimen data comprising a specimen image, wherein the specimen image comprises a plurality of voxels and at least one specimen multi-dimensional magnetic resonance (MR) spectrum;
   identifying at least one specimen spectral region of interest (sROI) within the at least one specimen multi-dimensional MR spectrum;
   determining a specimen signature corresponding to each of the at least one specimen sROI;
   comparing each specimen signature to a library of reference signatures, wherein each reference signature is associated with a different type of traumatic brain injury (TBI), wherein each reference signature comprises a reference sROI and a corresponding weight; and
   categorizing the plurality of voxels of the specimen image based on the comparison to form a categorized image.

2. The method of claim 1, further comprising assigning at least a first data value to the at least one specimen sROI based on the categorization.

3. The method of claim 2, wherein the first data value is assigned based on the comparison.

4. The method of claim 1, further comprising displaying the categorized image.

5. The method of claim 1, wherein the at least one specimen multi-dimensional MR spectrum is based on a partial multi-dimensional MR spectra of lower dimension.

6. The method of claim 1, wherein the specimen image includes a portion of a brain and the categorization is based on an indication of brain injury.

7. The method of claim 1, wherein the at least one specimen multi-dimensional MR spectrum is a T1-T2 spectrum, wherein the method further comprises:
   categorizing locations associated with each of the plurality of voxels based on a combination of spectral values associated with the at least one specimen sROI of the at least one specimen multi-dimensional MR spectrum; and
   displaying the specimen image based on the categorization.

8. The method of claim 1, wherein the at least one specimen multi-dimensional MR spectrum is a T1-MD spectrum, wherein the method further comprises:
   categorizing locations associated with each of the plurality of voxels based on a combination of spectral values associated with the at least one specimen sROI of the at least one multi-dimensional MR spectrum; and
   displaying the specimen image based on the categorization.

9. The method of claim 1, wherein the at least one specimen multi-dimensional MR spectrum is a T2-MD spectrum, wherein the method further comprises:
   categorizing locations associated with each of the plurality of voxels based on a combination of spectral values associated with the at least one specimen sROI of the at least one multi-dimensional MR spectrum; and
   displaying the specimen image based on the categorization.

10. The method of claim 1, wherein the at least one specimen multi-dimensional MR spectrum is a T1-T2-MD spectrum, wherein the method further comprises:
    categorizing locations associated with each of the plurality of voxels based on a combination of spectral values associated with the at least one specimen sROI of the at least one multi-dimensional MR spectrum; and displaying the specimen image based on the categorization.

11. The method of claim 1, wherein the at least one specimen multidimensional MR spectra are one or more of T1-T2, T1-MD, T2-MD spectra, or spectra corresponding to any combination of two or more of T1, T2, MD, $D_{iso}$, $D_\Delta$, and $(\theta, \phi)$.

12. The method of claim 1, wherein the reference sROI indicates a reference multidimensional MR spectrum that is defined by a T1 range, a T2 range, and a MD range.

13. The method of claim 12, wherein the T1 range is about 90 ms to 350 ms, the T2 range is about 6 to 40 ms, and the MD range is about 0.004 to 0.150 μm²/ms.

14. A system, comprising:
a magnetic resonance imaging (MRI) apparatus operable to obtain specimen data comprising a specimen image, wherein the specimen image comprises a plurality of voxels and at least one specimen multi-dimensional magnetic resonance (MR) spectrum;
a memory storing a library of reference signatures, wherein each reference signature is associated with a different type of traumatic brain injury (TBI), wherein each reference signature comprises a reference spectral region of interest (sROI) and a corresponding weight; and
a processor coupled to the MRI apparatus and configured to:
identify at least one specimen sROI within the at least one specimen multi-dimensional MR spectrum;
determine a specimen signature corresponding to each of the at least one specimen sROI;
compare each specimen signature to the library of reference signatures; and
categorize the plurality of voxels of the specimen image based on the comparison to form a categorized image.

15. The system of claim 14, wherein the at least one specimen multidimensional MR spectral range is defined by T1, T2, and/or MD ranges.

16. The system of claim 15, wherein the T1, T2, and MD ranges are T1=[91.03, 339.32] ms, T2=[6.70, 34.85] ms, and MD=[0.004, 0.146]m²/ms.

17. A non-transitory computer-readable medium having processor-executable instructions stored thereon, wherein the processor-executable instructions, when executed, perform:
obtaining specimen data comprising a specimen image, wherein the specimen image comprises a plurality of voxels and at least one specimen multi-dimensional magnetic resonance (MR) spectrum;
identifying at least one specimen spectral region of interest (sROI) within the at least one specimen multi-dimensional MR spectrum;
determining a specimen signature corresponding to each of the at least one specimen sROI;
comparing each specimen signature to a library of reference signatures, wherein each reference signature is associated with a different type of traumatic brain injury (TBI), wherein each reference signature comprises a reference sROI and a corresponding weight; and
categorizing the plurality of voxels of the specimen image based on the comparison to form a categorized image.

* * * * *